US008221819B2

(12) United States Patent
Ursin et al.

(10) Patent No.: US 8,221,819 B2
(45) Date of Patent: Jul. 17, 2012

(54) FATTY ACID DESATURASES FROM PRIMULA

(75) Inventors: Virginia Ursin, Pawcatuck, CT (US); Byron Froman, Davis, CA (US); Jennifer Simmons, Woodland, CA (US); Thomas J. LaRosa, Fenton, MO (US); Fenggao Dong, Chesterfield, MO (US); Steven Screen, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 618 days.

(21) Appl. No.: 11/891,426

(22) Filed: Jun. 12, 2008

(65) Prior Publication Data
US 2009/0176879 A1 Jul. 9, 2009

Related U.S. Application Data

(63) Continuation of application No. 10/569,387, filed as application No. PCT/US2004/026944 on Aug. 20, 2004.

(60) Provisional application No. 60/496,751, filed on Aug. 21, 2003.

(51) Int. Cl.
*A23K 1/00* (2006.01)
*A23K 1/14* (2006.01)

(52) U.S. Cl. ........................................ 426/623; 426/630

(58) Field of Classification Search ........................ None
See application file for complete search history.

(56) References Cited

U.S. PATENT DOCUMENTS

| 3,488,198 A | 1/1970 | Bundus |
| 3,676,157 A | 7/1972 | Wintersdorff et al. |
| 4,273,790 A | 6/1981 | Bosco et al. |
| 4,757,011 A | 7/1988 | Minekus et al. |
| 4,776,984 A | 10/1988 | Traitler et al. ............ 260/412.2 |
| 4,910,141 A | 3/1990 | Wong et al. ................ 536/23.1 |
| 4,913,921 A | 4/1990 | Schroeder et al. |
| 4,940,835 A | 7/1990 | Shah et al. |
| 5,057,419 A | 10/1991 | Martin et al. |
| 5,097,093 A | 3/1992 | Vandeventer et al. |
| 5,130,449 A | 7/1992 | Lagarde et al. ................ 554/186 |
| 5,340,594 A | 8/1994 | Barclay |
| 5,349,123 A | 9/1994 | Shewmaker et al. |
| 5,376,541 A | 12/1994 | Kawashima et al. |
| 5,405,765 A | 4/1995 | Vasil et al. |
| 5,443,974 A | 8/1995 | Hitz et al. |
| 5,484,956 A | 1/1996 | Lundquist |
| 5,498,830 A | 3/1996 | Barry et al. |
| 5,552,306 A | 9/1996 | Thomas et al. |
| 5,591,616 A | 1/1997 | Hiei et al. |
| 5,614,393 A | 3/1997 | Thomas et al. |
| 5,614,400 A | 3/1997 | Cahoon et al. |
| 5,656,319 A | 8/1997 | Barclay |
| 5,668,292 A | 9/1997 | Somerville et al. |
| 5,668,299 A | 9/1997 | Debonte ........................ 800/230 |
| 5,763,745 A | 6/1998 | Fehr et al. |
| 5,795,614 A | 8/1998 | Krishnamurthy et al. |
| 5,880,275 A | 3/1999 | Fischhoff et al. |
| 5,886,244 A | 3/1999 | Tomes et al. |
| 5,952,544 A | 9/1999 | Browse et al. ................ 800/295 |
| 5,959,175 A | 9/1999 | Thomas et al. ............... 800/287 |
| 5,968,809 A | 10/1999 | Knutzon et al. |
| 5,972,664 A | 10/1999 | Knutzon et al. |
| 5,977,436 A | 11/1999 | Thomas et al. ............... 800/281 |
| 5,985,348 A | 11/1999 | Barclay |
| 6,051,754 A | 4/2000 | Knutzon |
| 6,075,183 A | 6/2000 | Knutzon |
| 6,117,677 A | 9/2000 | Thompson et al. |
| 6,123,978 A | 9/2000 | Dartey et al. |
| 6,136,574 A | 10/2000 | Knutzon et al. |
| 6,355,861 B1 | 3/2002 | Thomas |
| 6,384,301 B1 | 5/2002 | Martinell et al. ............ 800/294 |
| 6,387,883 B1 | 5/2002 | Abbruzzese et al. |
| 6,399,137 B1 | 6/2002 | Dartey et al. |
| 6,459,018 B1 | 10/2002 | Knutzon .................... 800/320.3 |
| 6,506,965 B1 | 1/2003 | Carolo |
| 6,603,061 B1 | 8/2003 | Armstrong et al. ........... 800/294 |
| 6,803,499 B1 | 10/2004 | Anderson et al. |
| 7,037,547 B2 | 5/2006 | Akashe et al. |
| 7,037,692 B1 | 5/2006 | Thompson et al. ........... 435/134 |
| 7,041,324 B2 | 5/2006 | Myhre |
| 7,087,432 B2 | 8/2006 | Qui et al. |

(Continued)

FOREIGN PATENT DOCUMENTS
AU 2003206846 2/2003
(Continued)

OTHER PUBLICATIONS

Kinney A.J. et al. Manipulating desaturase activities in transgenic crop plants. Biochem Soc Trans. Nov. 2002;30(Pt 6):1099-103.*
Amendment and Response to Office Action regarding U.S. Appl. No. 10/569,387, dated Jan. 26, 2011.
Alonso and Garcia-Maroto, "Plants as 'chemical factories' for the production of polyunsaturated fatty acids," *Biotechnology Advances*, 18(6):481-497, 2000.
Conti et al., "γ-linolenic acid production by solid-state fermentation of mucorales strains on cereals," *Bioresource Technology*, 76:283-286, 2001.
EBI Accession No. AEE85555, dated Feb. 23, 2006.
EBI Accession No. AEE85556, dated Feb. 23, 2006.
Garcia-Maroto et al., "Cloning and molecular characterization of the delta6-desaturase from two echium plant species: production of GLA by heterologous expression in yeast and tobacco," *Lipids*, 37(4):417-26, 2002.

(Continued)

*Primary Examiner* — Cynthia Collins
(74) *Attorney, Agent, or Firm* — SNR Denton US LLP; Byron V. Olsen Esq.

(57) ABSTRACT

The invention relates generally to methods and compositions concerning desaturase enzymes that modulate the number and location of double bonds in long chain poly-unsaturated fatty acids (LC-PUFA's). In particular, the invention relates to methods and compositions for improving omega-3 fatty acid profiles in plant products and parts using desaturase enzymes and nucleic acids encoding for such enzymes. In particular embodiments, the desaturase enzymes are *Primula* Δ6-desaturases. Also provided are improved soybean oil compositions having SDA and a beneficial overall content of omega-3 fatty acids relative to omega-6 fatty acids.

31 Claims, 14 Drawing Sheets

U.S. PATENT DOCUMENTS

| | | | |
|---|---|---|---|
| 7,344,747 B2 | 3/2008 | Perlman | |
| 7,550,170 B2 | 6/2009 | Shiiba et al. | |
| 7,554,008 B2 | 6/2009 | Napier et al. | |
| 7,622,632 B2 * | 11/2009 | Ursin et al. | 800/281 |
| RE41,139 E | 2/2010 | Knutzon | 800/281 |
| 7,659,120 B2 | 2/2010 | Yadav et al. | |
| 7,705,215 B1 | 4/2010 | Adams et al. | 800/320.1 |
| 7,741,500 B2 | 6/2010 | Arhancet et al. | |
| 7,785,645 B2 | 8/2010 | Siew et al. | |
| 2002/0156254 A1 | 10/2002 | Qiu et al. | |
| 2003/0082275 A1 | 5/2003 | Myhre | |
| 2004/0107460 A1 | 6/2004 | Fillatti et al. | |
| 2004/0172682 A1 | 9/2004 | Kinney et al. | |
| 2004/0224071 A1 | 11/2004 | Siew et al. | |
| 2005/0132441 A1 | 6/2005 | Damude et al. | |
| 2005/0132442 A1 | 6/2005 | Yadav et al. | |
| 2005/0181019 A1 | 8/2005 | Palmer et al. | |
| 2005/0244564 A1 | 11/2005 | Perlman | |
| 2006/0062888 A1 | 3/2006 | Shiiba et al. | |
| 2006/0111254 A1 | 5/2006 | Makadia et al. | |
| 2006/0111578 A1 | 5/2006 | Arhancet et al. | |
| 2006/0156435 A1 | 7/2006 | Ursin et al. | 800/281 |
| 2008/0063691 A1 | 3/2008 | Ursin et al. | 800/281 |
| 2008/0155705 A1 | 6/2008 | Zack et al. | 800/281 |
| 2008/0260929 A1 | 10/2008 | Ursin et al. | |
| 2009/0110800 A1 | 4/2009 | Wilkes | |
| 2010/0212045 A1 | 8/2010 | Ursin et al. | 800/281 |

FOREIGN PATENT DOCUMENTS

| | | |
|---|---|---|
| EP | 0 537 178 B1 | 8/1994 |
| EP | 1 086 236 | 6/1999 |
| EP | 0 936 266 B1 | 8/1999 |
| EP | 0 550 162 A1 | 3/2001 |
| EP | 0 644 263 B1 | 12/2002 |
| EP | 0 561 569 A2 | 6/2003 |
| EP | 0 616 644 B1 | 7/2003 |
| EP | 0 736 598 B1 | 8/2004 |
| WO | WO 91/10725 A1 | 7/1991 |
| WO | WO 91/13972 A1 | 9/1991 |
| WO | WO 93/06712 | 4/1993 |
| WO | WO 93/11245 A1 | 6/1993 |
| WO | WO 94/11516 A1 | 5/1994 |
| WO | WO 94/18337 A1 | 8/1994 |
| WO | WO 96/10086 A1 | 4/1996 |
| WO | WO 96/21022 | 7/1996 |
| WO | WO 97/21340 A1 | 6/1997 |
| WO | WO 97/30582 A1 | 8/1997 |
| WO | WO 97/46219 A1 | 12/1997 |
| WO | WO 97/46220 A1 | 12/1997 |
| WO | WO 97/46649 A1 | 12/1997 |
| WO | WO 98/45460 A1 | 10/1998 |
| WO | WO 98/46763 | 10/1998 |
| WO | WO 98/46764 A1 | 10/1998 |
| WO | WO 99/64614 * | 12/1999 |
| WO | WO 02/011550 A2 | 2/2002 |
| WO | WO 02/092073 | 11/2002 |
| WO | WO 03/075670 | 3/2003 |
| WO | WO 03/072784 | 9/2003 |
| WO | WO 03/099216 | 12/2003 |
| WO | WO 2005/012316 | 2/2005 |
| WO | WO 2005/021761 A1 | 3/2005 |
| WO | WO 2005/118814 | 12/2005 |

OTHER PUBLICATIONS

GenBank Accession No. AX577009, dated Jan. 8, 2003.
GenBank Accession No. AY234125, May 4, 2003.
GenPept Accession No. AAF08685, dated Nov. 18, 1999.
James and Cleland, "Dietary n-3 fatty acids and therapy for reumatoid arthritis," *Semin Arthritis Rheum*, 27(2):85-97, 1997.
Libisch et al., "Chimeras of Delta6-fatty acid and Delta8-sphingolipid desaturases," *Biochem Biophys Res Commun*, 279(3):779-85, 2000.
Meesapyodsuk et al., "Characterization of the regiochemistry and cryptoregiochemistry of a *Caenorhabditis elegans* fatty acid desaturase (FAT-1) expressed in *Saccharomyces cerevisiae*," *Biochemistry*, 39(39):11948-54, 2000.
Michaelson et al., "Functional identification of a fatty acid delta5 desaturase gene from *Caenorhabditis elegans*," *FEBS Lett*, 439(3):215-8, 1998.
Michaelson et al., "Isolation and characterization of a cDNA encoding a Delta8 sphingolipid desaturase from *Aquilegia vulgaris*," *Biochem Soc Trans*, 30(Pt 6):1073-5, 2002.
Napier et al., "A new class of cytochrome b5 fusion proteins," *Biochem J*, 328:717-720, 1997.
Napier et al., "Identification of a *Caenorhabditis elegans* Delta6-fatty-acid-desaturase by heterologous expression in *Saccharomyces cerevisiae*," *Biochem J*, 330(Pt 2):611-4, 1998.
Napier et al., "The role of cytochrome b5 fusion desaturases in the synthesis of polyunsaturated fatty acids," *Prostaglandins Leukot Essent Fatty Acids*, 68(2):135-43, 2003.
Sayanova et al., "Histidine-41 of the cytochrome b5 domain of the borage delta6 fatty acid desaturase is essential for enzyme activity," *Plant Physiol*, 121:641-646, 1999.
Sayanova et al., "Identification of primula fatty acid delta 6-desaturases with n-3 substrate preferences," *FEBS Letters*, 542:100-104, 2003.
Sayanova et al., "$\Delta^6$-unsaturated fatty acids in the species and tissues of the primulaceae," *Phytochemistry*, 52:419-422, 1999.
Shanklin et al., "Eight histidine residues are catalytically essential in a membrane-associated iron enzyme, stearoyl-CoA desaturase, and are conserved in alkane hydroxylase and xylene monooxygenase," *Biochemistry*, 33:12787-12794, 1994.
Sperling and Heinz, "Desaturases fused to their electron donor," *Eur J Lipid Sci Technolo*, 103:158-180, 2001.
Sperling et al., "Functional identification of a delta8-sphingolipid desaturase from *Borago officinalis*," *Arch Biochem Biophys*, 388(2):293-8, 2001.
Whitney et al., "Functional characterisation of two cytochrome b5-fusion desaturases from *Anemone leveillei*: the unexpected identification of a fatty acid Delta6-desaturase," *Planta*, 217(6):983-92, 2003.
U.S. Appl. No. 60/089,043, filed Mar. 26, 2007, Knutzon.
Bhella et al., "Nucleotide sequence of a cDNA from *Limnanthes douglasii* L. encoding a delta-15 linoleic acid desaturase," *Plant Physiol.*, 108:861, 1995.
File Wrapper for U.S. Appl. No. 11/445,506, dated May 31, 2006.
Griffiths et al., "Distribution and Biosynthesis of stearidonic acid in leaves of *Borago officinalis*," *Phytochemistry*, 43(2):381-386, 1996.
Gryson et al., "Detection of DNA during the refining of soybean oil," *JAOCS*, 79(2):171-174, 2002.
Katavic et al., "Alteration of seed fatty acid compositions by an ethyl methanesulfonate-induced mutation in *Arabidopsis thaliana* affecting diacylglycerol acyltransferase activity," *Plant Physiol.*, 108:399-409, 1995.
Kunst et al., "Fatty acid elongation in developing seeds of *Arabidopsis thaliana*," *Plant Physiol. Biochem.*, 30(4):425-434, 1992.
Reddy et al., "Expression of a cyanobacterial delta6—desaturase gene results in gamma-linolenic acid production in transgenic plants," *Nature Biotech.*, 14:639-642, 1996.
Sayanova et al., "Expression of a borage desaturase cDNA containing an N-terminal cytochrome b5 domain results in the accumulation of high levels of delta6—desaturated fatty acids in transgenic tobacco," *Proc. Natl. Acad. Sci. USA*, 94:4211-4216, 1997.
Tsevegsuren et al., "Gamma-linolenic and stearidonic acid in mongolian boraginaceae seed oils," *J. Amer. Oil Chem. Soc.*, 73:1681-1684, 1996.
Ucciani et al., "Fatty acid composition of oils of saxifragaceae," *Fiche Technique*, 2(6):491-493, 1995.
Ucciani et al., "Composition en acides gras d'huiles de saxifragaceae," *Fiche Technique*, 2(6):491-493, 1995.
Ursin et al., "Modification of plant lipids for human health: development of functional land-based omega-3 fatty acids," *J. of Nutrition*, 133(12):4271-4274, 2003.
Office Action regarding U.S. Appl. No. 08/113,561, dated May 13, 2004.
Amendment and Response to Office Action regarding U.S. Appl. No. 08/113,561, dated Oct. 18, 2004.

Final Office Action regarding U.S. Appl. No. 08/113,561, dated Jan. 26, 2005.
Brief on Appeal regarding U.S. Appl. No. 08/113,561, dated Jul. 1, 2005.
Examiner's Answer to Appeal Brief regarding U.S. Appl. No. 08/113,561, dated Sep. 23, 2005.
Reply Brief regarding U.S. Appl. No. 08/113,561, dated Nov. 28, 2005.
Notification of Non-Compliant Appeal Brief regarding U.S. Appl. No. 08/113,561, dated Jun. 26, 2006.
Response to Notification of Non-Compliant Appeal Brief and Supplemental Brief on Appeal regarding U.S. Appl. No. 08/113,561, dated Jul. 24, 2006.
Examiner's Answer to Appeal Brief regarding U.S. Appl. No. 08/113,561, dated Sep. 13, 2006.
Reply Brief regarding U.S. Appl. No. 08/113,561, dated Nov. 13, 2006.
Board of Patent Appeals and Interferences Decision on Appeal regarding U.S. Appl. No. 08/113,561, decided Feb. 20, 2008, dated Feb. 20, 2008.
Transcript of Oral Hearing held Feb. 12, 2008 regarding U.S. Appl. No. 08/113,561, dated Mar. 13, 2008.
Office Action regarding U.S. Appl. No. 08/113,561, dated Mar. 24, 2008.
Response to Office Action regarding U S. Appl. No. 08/113,561, dated Aug. 25, 2008.
Office Action regarding U.S. Appl. No. 08/113,561, dated Dec. 5, 2008.
Response to Office Action regarding U.S. Appl. No. 08/113,561, dated Mar. 3, 2009.
Final Office Action regarding U.S. Appl. No. 08/113,561, dated Jun. 17, 2009.
Telephonic Interview Summary and Response to Office Action regarding U.S. Appl. No. 08/113,561, dated Sep. 10, 2009.
Office Action regarding U.S. Appl. No. 10/569,387, dated Sep. 20, 2011.
"Fats and Oils Formulation," In: Fats and Oils—Formulating and Processing for Applications, O'Brien (Ed.), CRC Press, $2^{nd}$ Edition, pp. 235-240, 2003.
"Monsanto launches vistive low-linolenic soybeans," *Inform*, 15(11):752 Processing, 2004.
ACS Symposium Series 788, In: Omega-3 Fatty Acids—Chemistry, Nutrition, and Health, Shahidi et al. (Eds.), American Chemical Society, Washington, D.C., pp. 57-3-57-24, 2001.
Arondel et al., "Map-based cloning of a gene controlling omega-3 fatty acid desaturation in arabidopsis," *Science*, 258:1353-1355, 1992. (Abstract).
Aïtzetmüeller et al., "Stearidonic acid (18:4[omega]3) in primula florindae," *Phytochemistry*, 30:4011-4013, 1991.
Casas et al., "Transgenic sorghum plants via microprojectile bombardment," *PNAS USA*, 90:11212-11216, 1993.
Covello et al., "Functional expression of the extraplastidial *Arabidopsis thaliana* oleate desaturase gene (FAD2) in *Saccharomyces cerevisiae*," *Plant Physiology*, 111:223-226, 1996.
Fourgoux et al., "Isolation of rapeseed genes expressed early and specifically during development of the male gametophyte," *Plant Mol. Biol.*, 40:857-872, 1999.
Fox et al., "Stearoyl-acyl carrier protein delta$^9$ desaturase from ricinus communis is a diironoxo protein," *Proc. Natl. Acad. Sci.*, 90:2486-2490, 1993.
Guichardant et al., "Stearidonic acid, and inhibitor of the 5-lipoxygenase pathway. A comparison with timnodonic and dihomogammalinolenic acid," *Lipids*, 28(4):321-24, 1993.
Heppard et al., "Developmental and growth temperature regulation of two different microsomal omega-6 desaturase genes in soybeans," *Plant Physiol.*, 110:311-319, 1996.
Horrobin, "Fatty acid metabolism in health and disease: the role of delta 6-desaturase," *Am. J. Clin. Nutr.*, 57(Supp.):732S-737S, 1993.
James et al., "Metabolism of stearidonic acid in human subjects: comparison with the metabolism of other n-3 fatty acids," *Amer. J. Clin. Nutr.*, 77:1140-1145, 2003.
Kindle et al., "High-frequency nuclear transformation of *Chlamydomonas reinhardtii*," *PNAS USA*, 87:1228-1232, 1990.

Kitamura et al., "Breeding trials for improving the food-processing quality of soybeans," *Trends in Food Sci & Technol.*, 4:64-67, 1993.
Kossmann et al., "Transgenic plants as a tool to understand starch biosynthesis," In: Carbohydrate Bioengineering, Peterson et al., (Eds.), Elsevier Science B.V., Amsterdam, 1995.
La Guardia et al., "Omega 3 fatty acids: biological activity and effects on human health," *Panminerva Med*, 47(4):245-257, 2005.
McDonough et al., "Specificity of unsaturated fatty acid-regulated expression of the *Saccharomyces cerevisiae* OLE1 gene," *J. of Biological Chemistry*, 267(9):5931-5936,1992.
Okuley et al., "*Arabidopsis* FAD2 gene encodes the enzyme that is essential for polyunsaturated lipid synthesis," *Plant Cell*, 6:147-158, 1994.
Post-Beittenmiller et al., "Expression of holo and apo forms of spinach acyl carrier protein-I in leaves of transgenic tobacco plants," *The Plant Cell*, 1:889-899, 1989.
Potrykus, "Gene transfer to plants: assessment of published approaches and results," *Ann. Rev. Plant Physiol. Plant Mol. Biology*, 42:205-225, 1991.
Reddy et al., "Isolation of a delta 6-desaturase gene from the *Cyanobacterium synechocystis* sp. strain PCC 6803 by gain-of-function expression *Anabaena* sp. strain PCC 7120," *Plant Mol. Biol.*, 22(2):293-300, 1993, Abstract only.
RefSeq Accession No. XP_002166163, dated Jan. 21, 2009.
RefSeq Accession No. XP_374163, dated Aug. 19, 2004.
Rocha-Uribe, "Physical Oxidative stability of mayonnaise enriched with different levels of N-3 fatty acids and stored at different temperatures," IFT Annual Meeting, Las Vegas, NV, Jul. 12-16, 2004.
Sato et al., "Production of y-linolenic acid and stearidonic acid in seeds of marker -free transgenic soybean," *Crop Sci.*, 44:646-522, 2004.
Spychalla et al., "Identification of an animal omega-3 fatty acid desaturase by heterologous expression in arabidopsis," *PNAS USA*, 94:1142-1147, 1997.
Stephanopoulos et al., "Metabolic engineering—methodologies and future prospects," *Trends in Biotechnology*, 11:392-396. 1993.
Whelan et al., "Innovative dietary sources of N-3 fatty acids," *Annu. Rev. Nutr.*, 26:75-103, 2006.
Yadav et al., "Cloning of higher plant omega-3 fatty acid desaturases," *Plant Physiol.*, 103:467-476, 1993.
International Search Report and Written Opinion from PCT/US2008/000051, dated Jun. 11, 2008.
First Examination Report received in New Zealand Application No. 578165, dated Aug. 11, 2010.
Office Action regarding U.S. Appl. No. 10/569,387, dated Oct. 26, 2010.
Score Search Result from U.S. Appl. No. 10/569,387, dated Oct. 20, 2010.
Final Office Action regarding U.S. Appl. No. 10/569,387, dated Apr. 8, 2011.
Office Action regarding U.S. Appl. No. 11/578,447, dated Nov. 10, 2010.
Response to Office Action regarding U.S. Appl. No. 11/578,447, dated Apr. 11, 2011.
Office Action regarding U.S. Appl. No. 12/006,388, dated Apr. 27, 2010.
Amendment and Response to Office Action regarding U.S. Appl. No. 12/006,388, dated Jul. 26, 2010.
Final Office Action regarding U.S. Appl. No. 12/006,388, dated Oct. 27, 2010.
Response to Office Action regarding U.S. Appl. No. 12/006,388, dated Jan. 27, 2010.
Advisory Action regarding U.S. Appl. No. 12/006,388, dated Feb. 16, 2011.
Request for Continued Examination regarding U.S. Appl. No. 12/006,388, dated Mar. 18, 2011.
"Main World Source of Oils," www.cyberlipid.org, undated, retrieved Jul. 19, 2011.
"Silk Soymilk," www.silkissoy.com, Jun. 17, 2002.
Chu et al., "Factors affecting the content of tocopherol in soybean oil," *JAOCS*, 70(12):1993.

Galiano, "How to make simple southern vanilla ice cream," www.littlerock.about.com, Feb. 1, 2002.

The Merck Index—Alpha and Gamma Linolenic Acids, May 18, 2011.

Office Action regarding U.S. Appl. No. 12/006,388, dated Jun. 23, 2011.

\* cited by examiner

FATTY ACID DESATURASES FROM PRIMULA

CROSS-REFERENCE TO RELATED APPLICATIONS

This application is a continuation of co-pending U.S. patent application Ser. No. 10/569,387 filed on Oct. 24, 2007 which in turn claims priority from PCTUS2004026944 filed on Aug. 20, 2004, which itself claims priority under 35 U.S.C. §119(e) from provisional application No. 60/496,751 that was filed Aug. 21, 2003.

BACKGROUND OF THE INVENTION

1. Field of the Invention

The invention relates generally to desaturase enzymes that modulate the number and location of double bonds in long chain poly-unsaturated fatty acids (LC-PUFA's). In particular, the invention relates to improvement of fatty acid profiles using desaturase enzymes and nucleic acids encoding such desaturase enzymes.

2. Description of the Related Art

The primary products of fatty acid biosynthesis in most organisms are 16- and 18-carbon compounds. The relative ratio of chain lengths and degree of unsaturation of these fatty acids vary widely among species. Mammals, for example, produce primarily saturated and monounsaturated fatty acids, while most higher plants produce fatty acids with one, two, or three double bonds, the latter two comprising polyunsaturated fatty acids (PUFA's).

Two main families of PUFAs are the omega-3 fatty acids (also represented as "n-3" fatty acids), exemplified by eicosapentaenoic acid (EPA, 20:4, n-3), and the omega-6 fatty acids (also represented as "n-6" fatty acids), exemplified by arachidonic acid (ARA, 20:4, n-6). PUFAs are important components of the plasma membrane of the cell and adipose tissue, where they may be found in such forms as phospholipids and as triglycerides, respectively. PUFAs are necessary for proper development in mammals, particularly in the developing infant brain, and for tissue formation and repair.

Several disorders respond to treatment with fatty acids. Supplementation with PUFAs has been shown to reduce the rate of restenosis after angioplasty. The health benefits of certain dietary omega-3 fatty acids for cardiovascular disease and rheumatoid arthritis also have been well documented (Simopoulos, 1997; James et al., 2000). Further, PUFAs have been suggested for use in treatments for asthma and psoriasis. Evidence indicates that PUFAs may be involved in calcium metabolism, suggesting that PUFAs may be useful in the treatment or prevention of osteoporosis and of kidney or urinary tract stones. The majority of evidence for health benefits applies to the long chain omega-3 fats, EPA and docosahexanenoic acid (DHA, 22:6) which are in fish and fish oil. With this base of evidence, health authorities and nutritionists in Canada (Scientific Review Committee, 1990, Nutrition Recommendations, Minister of National Health and Welfare, Canada, Ottowa), Europe (de Deckerer et al., 1998), the United Kingdom (The British Nutrition Foundation, 1992, Unsaturated fatty-acids—nutritional and physiological significance: The report of the British Nutrition Foundation's Task Force, Chapman and Hall, London), and the United States (Simopoulos et al., 1999) have recommended increased dietary consumption of these PUFAs.

PUFAs also can be used to treat diabetes (U.S. Pat. No. 4,826,877; Horrobin et al., 1993). Altered fatty acid metabolism and composition have been demonstrated in diabetic animals. These alterations have been suggested to be involved in some of the long-term complications resulting from diabetes, including retinopathy, neuropathy, nephropathy and reproductive system damage. Primrose oil, which contains γ-linolenic acid (GLA, 18:3, Δ6, 9, 12), has been shown to prevent and reverse diabetic nerve damage.

PUFAs, such as linoleic acid (LA, 18:2, Δ9, 12) and α-linolenic acid (ALA, 18:3, Δ9, 12, 15), are regarded as essential fatty acids in the diet because mammals lack the ability to synthesize these acids. However, when ingested, mammals have the ability to metabolize LA and ALA to form the n-6 and n-3 families of long-chain polyunsaturated fatty acids (LC-PUFA). These LC-PUFA's are important cellular components conferring fluidity to membranes and functioning as precursors of biologically active eicosanoids such as prostaglandins, prostacyclins, and leukotrienes, which regulate normal physiological functions. Arachidonic acid is the principal precursor for the synthesis of eicosanoids, which include leukotrienes, prostaglandins, and thromboxanes, and which also play a role in the inflammation process. Administration of an omega-3 fatty acid, such as SDA, has been shown to inhibit biosynthesis of leukotrienes (U.S. Pat. No. 5,158,975). The consumption of SDA has been shown to lead to a decrease in blood levels of proinflammatory cytokines TNF-α and IL-1β (PCT US 0306870).

In mammals, the formation of LC-PUFA is rate-limited by the step of Δ6 desaturation, which converts LA to γ-linolenic acid (GLA, 18:3, Δ6, 9, 12) and ALA to SDA (18:4, Δ6, 9, 12, 15). Many physiological and pathological conditions have been shown to depress this metabolic step even further, and consequently, the production of LC-PUFA. To overcome the rate-limiting step and increase tissue levels of EPA, one could consume large amounts of ALA. However, consumption of just moderate amounts of SDA provides an efficient source of EPA, as SDA is about four times more efficient than ALA at elevating tissue EPA levels in humans (copending U.S. application Ser. No. 10/384,369). In the same studies, SDA administration was also able to increase the tissue levels of docosapentaenoic acid (DPA), which is an elongation product of EPA. Alternatively, bypassing the Δ6-desaturation via dietary supplementation with EPA or DHA can effectively alleviate many pathological diseases associated with low levels of PUFA. However, as set forth in more detail below, currently available sources of PUFA are not desirable for a multitude of reasons. The need for a reliable and economical source of PUFA's has spurred interest in alternative sources of PUFA's.

Major long chain PUFAs of importance include DHA and EPA, which are primarily found in different types of fish oil, and ARA, found in filamentous fungi such as *Mortierella*. For DHA, a number of sources exist for commercial production including a variety of marine organisms, oils obtained from cold water marine fish, and egg yolk fractions. Commercial sources of SDA include the plant genera *Trichodesma*, *Borago* (borage) and *Echium*. However, there are several disadvantages associated with commercial production of PUFAs from natural sources. Natural sources of PUFAs, such as animals and plants, tend to have highly heterogeneous oil compositions. The oils obtained from these sources therefore can require extensive purification to separate out one or more desired PUFAs or to produce an oil which is enriched in one or more PUFAs.

Natural sources of PUFAs also are subject to uncontrollable fluctuations in availability. Fish stocks may undergo natural variation or may be depleted by overfishing. In addition, even with overwhelming evidence of their therapeutic benefits, dietary recommendations regarding omega-3 fatty acids are not heeded. Fish oils have unpleasant tastes and odors, which may be impossible to economically separate from the desired product, and can render such products unacceptable as food supplements. Animal oils, and particularly fish oils, can accumulate environmental pollutants. Foods may be enriched with fish oils, but again, such enrichment is problematic because of cost and declining fish stocks worldwide. This problem is also an impediment to consumption and intake of whole fish. Nonetheless, if the health messages to increase fish intake were embraced by communities, there would likely be a problem in meeting demand for fish. Furthermore, there are problems with sustainability of this industry, which relies heavily on wild fish stocks for aquaculture feed (Naylor et al., 2000).

Other natural limitations favor a novel approach for the production of omega-3 fatty acids. Weather and disease can cause fluctuation in yields from both fish and plant sources. Cropland available for production of alternate oil-producing crops is subject to competition from the steady expansion of human populations and the associated increased need for food production on the remaining arable land. Crops that do produce PUFAs, such as borage, have not been adapted to commercial growth and may not perform well in monoculture. Growth of such crops is thus not economically competitive where more profitable and better-established crops can be grown. Large scale fermentation of organisms such as *Mortierella* is also expensive. Natural animal tissues contain low amounts of ARA and are difficult to process. Microorganisms such as *Porphyridium* and *Mortierella* are difficult to cultivate on a commercial scale.

A number of enzymes are involved in the biosynthesis of PUFAs. LA (18:2, $\Delta$9, 12) is produced from oleic acid (OA, 18:1, $\Delta$9) by a $\Delta$12-desaturase while ALA (18:3, $\Delta$9, 12, 15) is produced from LA by a $\Delta$15-desaturase. SDA (18:4, $\Delta$6, 9, 12, 15) and GLA (18:3, $\Delta$6, 9, 12) are produced from LA and ALA by a $\Delta$6-desaturase. However, as stated above, mammals cannot desaturate beyond the $\Delta$9 position and therefore cannot convert oleic acid into LA. Likewise, ALA cannot be synthesized by mammals. Other eukaryotes, including fungi and plants, have enzymes which desaturate at the carbon 12 and carbon 15 position. The major polyunsaturated fatty acids of animals therefore are derived from diet via the subsequent desaturation and elongation of dietary LA and ALA.

Various genes encoding desaturases have been described. For example, U.S. Pat. No. 5,952,544 describes nucleic acid fragments isolated and cloned from *Brassica napus* that encode fatty acid desaturase enzymes. Expression of the nucleic acid fragments of the '544 patent resulted in accumulation of ALA. However, in transgenic plants expressing the *B. napus* $\Delta$15-desaturase, substantial LA remains unconverted by the desaturase. More active enzymes that convert greater amounts of LA to ALA would be advantageous. Increased ALA levels allow a $\Delta$6-desaturase, when co-expressed with a nucleic acid encoding for the $\Delta$15-desaturase, to act upon the ALA, thereby producing greater levels of SDA. Because of the multitude of beneficial uses for SDA, there is a need to create a substantial increase in the yield of SDA.

Nucleic acids from a number of sources have been sought for use in increasing SDA yield. However, innovations that would allow for improved commercial production in land-based, crops are still needed (see, e.g., Reed et al., 2000). Furthermore, the use of desaturase polynucleotides derived from organisms such as *Caenorhabditis elegans* (Meesapyodsuk et al., 2000) is not ideal for the commercial production of enriched plant seed oils. Genes encoding $\Delta$6-desaturases have been isolated from two species of *Primula*, *P. farinosa* and *P. vialii*, and these found to be active in yeast, but the function in plants was not shown (Sayanova et al., 2003).

Therefore, it would be advantageous to obtain genetic material involved in PUFA biosynthesis and to express the isolated material in a plant system, in particular, a land-based terrestrial crop plant system, which can be manipulated to provide production of commercial quantities of one or more PUFA's. There is also a need to increase omega-3 fat intake in humans and animals. Thus there is a need to provide a wide range of omega-3 enriched foods and food supplements so that subjects can choose feed, feed ingredients, food and food ingredients which suit their usual dietary habits. Particularly advantageous would be seed oils with increased SDA.

Currently there is only one omega-3 fatty acid, ALA, available in vegetable oils. However, there is poor conversion of ingested ALA to the longer-chain omega-3 fatty acids such as EPA and DHA. It has been demonstrated in copending U.S. application Ser. No. 10/384,369 for "Treatment And Prevention Of Inflammatory Disorders," that elevating ALA intake from the community average of 1/g day to 14 g/day by use of flaxseed oil only modestly increased plasma phospholipid EPA levels. A 14-fold increase in ALA intake resulted in a 2-fold increase in plasma phospholipid EPA (Manzioris et al., 1994). Thus, to that end, there is a need for efficient and commercially viable production of PUFAs using fatty acid desaturases, genes encoding them, and recombinant methods of producing them. A need also exists for oils containing higher relative proportions of specific PUFAs, and food compositions and supplements containing them. A need also exists for reliable economical methods of producing specific PUFA's.

Despite inefficiencies and low yields as described above, the production of omega-3 fatty acids via the terrestrial food chain is an enterprise beneficial to public health and, in particular, the production of SDA. SDA is important because, as described above, there is low conversion of ALA to EPA. This is because the initial enzyme in the conversion, $\Delta$6-desaturase, has low activity in humans and is rate-limiting. Evidence that $\Delta$6-desaturase is rate-limiting is provided by studies which demonstrate that the conversion of its substrate, ALA, is less efficient than the conversion of its product, SDA to EPA in mice and rats (Yamazaki et al., 1992; Huang, 1991).

Based on such studies, it is seen that in commercial oilseed crops, such as canola, soybean, corn, sunflower, safflower, or flax, the conversion of some fraction of the mono and polyunsaturated fatty acids that typify their seed oil to SDA requires the seed-specific expression of multiple desaturase enzymes, that includes $\Delta$6-, $\Delta$12- and/or $\Delta$15-desaturases. Oils derived from plants expressing elevated levels of $\Delta$6, $\Delta$12, and $\Delta$15-desaturases are rich in SDA and other omega-3 fatty acids. Such oils can be utilized to produce foods and food supplements enriched in omega-3 fatty acids and consumption of such foods effectively increases tissue levels of EPA and DHA. Foods and foodstuffs, such as milk, margarine and sausages, all made or prepared with omega-3 enriched oils, will result in therapeutic benefits. It has been shown that subjects can have an omega-3 intake comparable to EPA and DHA of at least 1.8 g/day without altering their dietary habits by utilizing foods containing oils enriched with omega-3 fatty acids. Thus, there exists a strong need for novel nucleic acids of $\Delta$6-desaturases for use in transgenic crop plants with oils enriched in PUFAs, as well as the improved oils produced thereby.

SUMMARY OF THE INVENTION

In one aspect, the invention provides isolated nucleic acids encoding a polypeptide capable of desaturating a fatty acid molecule at carbon 6 (Δ6-desaturase). These may be used to transform cells or modify the fatty acid composition of a plant or the oil produced by a plant. One embodiment of the invention is an isolated polynucleotide sequence isolated from a *Primula* species having unique desaturase activity. In certain embodiments, the isolated polynucleotides are isolated, for example, from *Primula juliae, P. alpicola, P. waltonii, P. farinosa* or *P. florindae*. In certain further embodiments of the invention, the polynucleotides encode a polypeptide having at least 90% sequence identity to the polypeptide sequence of SEQ ID NO:4, SEQ ID NO:5, SEQ ID NO:22, SEQ ID NO:24, SEQ ID NO:26, SEQ ID NO:46 or SEQ ID NO:48, including at least about 92%, 95%, 98% and 99% homology to these sequences. Those of skill in the art will recognize that, as these sequences are related, a given polypeptide may simultaneously share 90% or greater homology to more than one of these polypeptide sequences. In certain embodiments, a sequence provided by the invention has a substrate selectivity for α-linolenic acid relative to linoleic acid, as described herein. In further embodiments, there is at least 2:1 substrate selectivity for α-linolenic acid relative to linoleic acid, including from about 2:1 to about 2.9:1.

In another aspect, the invention provides an isolated polynucleotide that encodes a polypeptide having desaturase activity that desaturates a fatty acid molecule at carbon 6, comprising a sequence selected from the group consisting of: (a) a polynucleotide encoding the polypeptide of SEQ ID NO:4, SEQ ID NO:5, SEQ ID NO:22, SEQ ID NO:24, SEQ ID NO:26, SEQ ID NO:46 or SEQ ID NO:48; (b) a polynucleotide comprising the nucleic acid sequence of SEQ ID NO:2, SEQ ID NO:3, SEQ ID NO:21, SEQ ID NO:23, SEQ ID NO:25, SEQ ID NO:45 or SEQ ID NO:47; (c) a polynucleotide hybridizing to SEQ ID NO:2, SEQ ID NO:3, SEQ ID NO:21, SEQ ID NO:23, SEQ ID NO:25, SEQ ID NO:45 or SEQ ID NO:47, or a complement thereof, under conditions of 5×SSC, 50% formamide and 42° C.; and (d) a polynucleotide encoding a polypeptide with at least 90% sequence identity to a polypeptide sequence of SEQ ID NO:4, SEQ ID NO:5, SEQ ID NO:22, SEQ ID NO:24, SEQ ID NO:26, SEQ ID NO:46 or SEQ ID NO:48.

In yet another aspect, the invention provides a recombinant vector comprising an isolated polynucleotide in accordance with the invention. The term "recombinant vector" as used herein, includes any recombinant segment of DNA that one desires to introduce into a host cell, tissue and/or organism, and specifically includes expression cassettes isolated from a starting polynucleotide. A recombinant vector may be linear or circular. In various aspects, a recombinant vector may comprise at least one additional sequence chosen from the group consisting of: regulatory sequences operatively coupled to the polynucleotide; selection markers operatively coupled to the polynucleotide; marker sequences operatively coupled to the polynucleotide; a purification moiety operatively coupled to the polynucleotide; and a targeting sequence operatively coupled to the polynucleotide.

In still yet another aspect, the invention provides cells, such as mammal, plant, insect, yeast and bacteria cells transformed with the polynucleotides of the instant invention. In a further embodiment, the cells are transformed with recombinant vectors containing constitutive and tissue-specific promoters in addition to the polynucleotides of the instant invention. In certain embodiments of the invention, such cells may be further defined as transformed with a nucleic acid sequence encoding a polypeptide having desaturase activity that desaturates a fatty acid molecule at carbon 12 and/or 15.

The invention also provides a polypeptide comprising the amino acid sequence of SEQ ID NO:4, SEQ ID NO:5, SEQ ID NO:22, SEQ ID NO:24, SEQ ID NO:26, SEQ ID NO:46 or SEQ ID NO:48; or a fragment thereof having desaturase activity that desaturates a fatty acid molecule at carbon 6.

Still yet another aspect of the invention provides a method of producing seed oil containing omega-3 fatty acids from plant seeds, comprising the steps of (a) obtaining seeds of a plant according to the invention; and (b) extracting the oil from said seeds. Examples of such a plant include canola, soy, soybeans, rapeseed, sunflower, cotton, cocoa, peanut, safflower, coconut, flax, oil palm, oilseed *Brassica napus*, and corn. Preferred methods of transforming such plant cells include the use of Ti and Ri plasmids of *Agrobacterium*, electroporation, and high-velocity ballistic bombardment.

In still yet another aspect, the invention provides a method of producing a plant comprising seed oil containing altered levels of omega-3 fatty acids comprising introducing a recombinant vector of the invention into an oil-producing plant. In the method, introducing the recombinant vector may comprise genetic transformation. In embodiment, transformation comprises the steps of: (a) transforming a plant cell with a recombinant vector of the invention; and (b) regenerating the plant from the plant cell, wherein the plant has altered levels of omega-3 fatty acids relative to a corresponding plant of the same genotype that was not transformed with the vector. In the method, the plant may, for example, be selected from the group consisting of *Arabidopsis thaliana*, oilseed *Brassica*, rapeseed, sunflower, safflower, canola, corn, soybean, cotton, flax, jojoba, Chinese tallow tree, tobacco, cocoa, peanut, fruit plants, citrus plants, and plants producing nuts and berries. The plant may be further defined as transformed with a nucleic acid sequence encoding a polypeptide having desaturase activity that desaturates a fatty acid molecule at carbon 12 and/or 15. The plant may comprise increased SDA. The method may further comprise introducing the recombinant vector into a plurality of oil-producing plants and screening the plants or progeny thereof having inherited the recombinant vector for a plant having a desired profile of omega-3 fatty acids.

In still yet another aspect, the invention provides an endogenous soybean seed oil having a SDA content of from about 5% to about 50% and a gamma-linoleic acid content of less than about 10%. The SDA content may, in certain embodiments, be further defined as from about 5% to about 32%, from about 5% to about 35%, from about 15% to about 30%, from about 22% to about 30%, and from about 22% to about 40%. The gamma-linoleic acid content may, in further embodiments, be defined as less than about 10, 8, 5 and/or about 3%. In particular embodiments, the stearidonic acid content may be from about 15% to about 35% and the gamma-linoleic acid content less than 5%. In still further embodiments, the seed may comprise a ratio of omega-3 to omega-6 fatty acids of from about 0.35:1 to about 3.5:1, including from about 1:1 to about 3.5:1 and from about 2:1 to about 3.5:1.

In still yet another aspect, the invention provides a method of increasing the nutritional value of an edible product for human or animal consumption, comprising adding a soybean seed oil provided by the invention to the edible product. In certain embodiments, the product is human and/or animal food. The edible product may also be animal feed and/or a food supplement. In the method, the soybean seed oil may increase the SDA content of the edible product and/or may increase the ratio of omega-3 to omega-6 fatty acids of the edible product. The edible product may lack SDA prior to adding the soybean seed oil.

In still yet another aspect, the invention provides a method of manufacturing food or feed, comprising adding a soybean seed oil provided by the invention to starting food or feed ingredients to produce the food or feed. In certain embodiments, the method is further defined as a method of manufacturing food and/or feed. The invention also provides food or feed made by the method.

In still yet another aspect, the invention comprises a method of providing SDA to a human or animal, comprising administering the soybean seed oil of claim 1 to said human or animal. In the method, the soybean seed oil may be administered in an edible composition, including food or feed. Examples of food include beverage's, infused foods, sauces, condiments, salad dressings, fruit juices, syrups, desserts, icings and fillings, soft frozen products, confections or intermediate food. The edible composition may be substantially a liquid or solid. The edible composition may also be a food supplement and/or nutraceutical. In the method, the soybean seed oil may be administered to a human and/or an animal. Examples of animals the oil may be administered to include livestock or poultry.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

Figure 1:
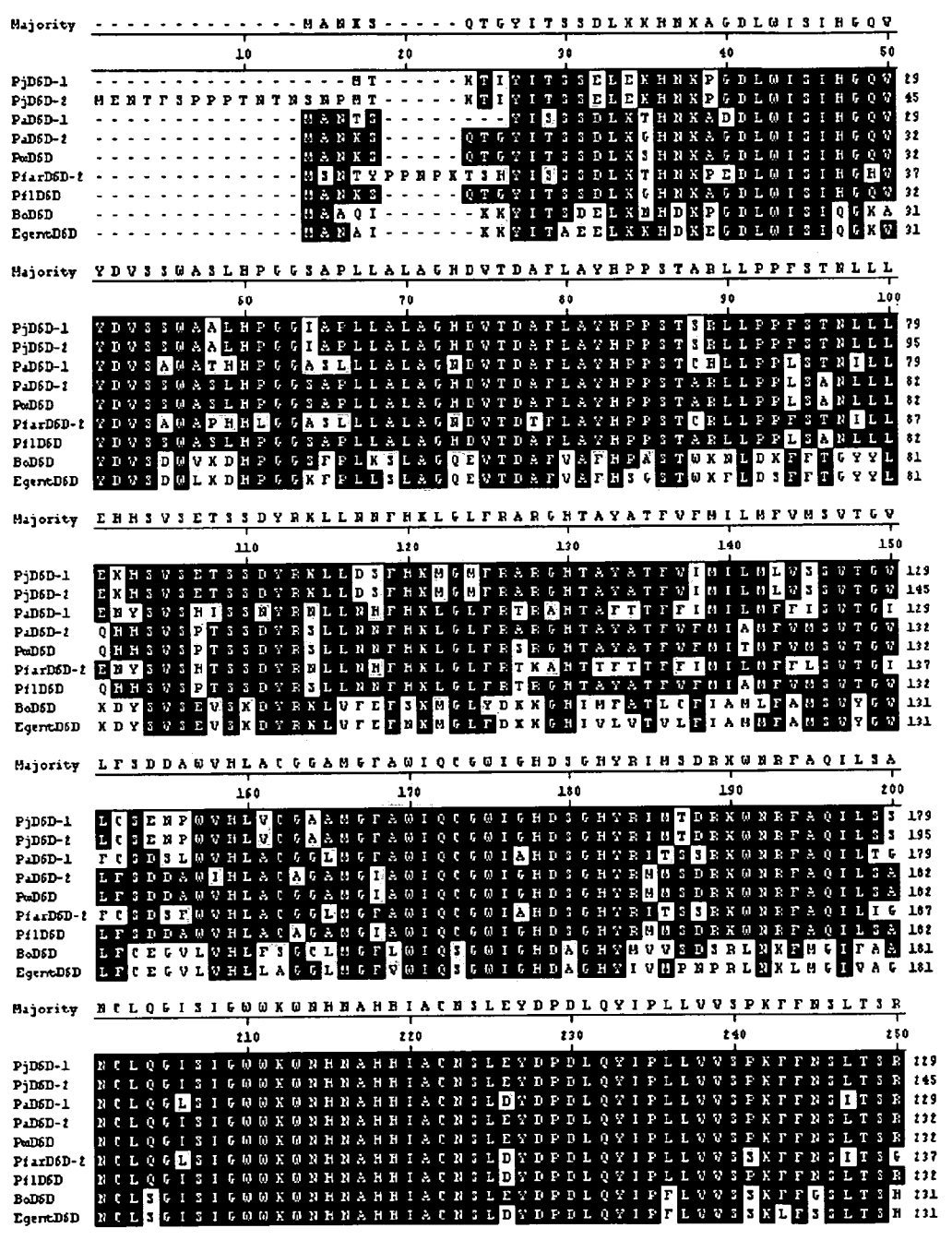
Figure 1:
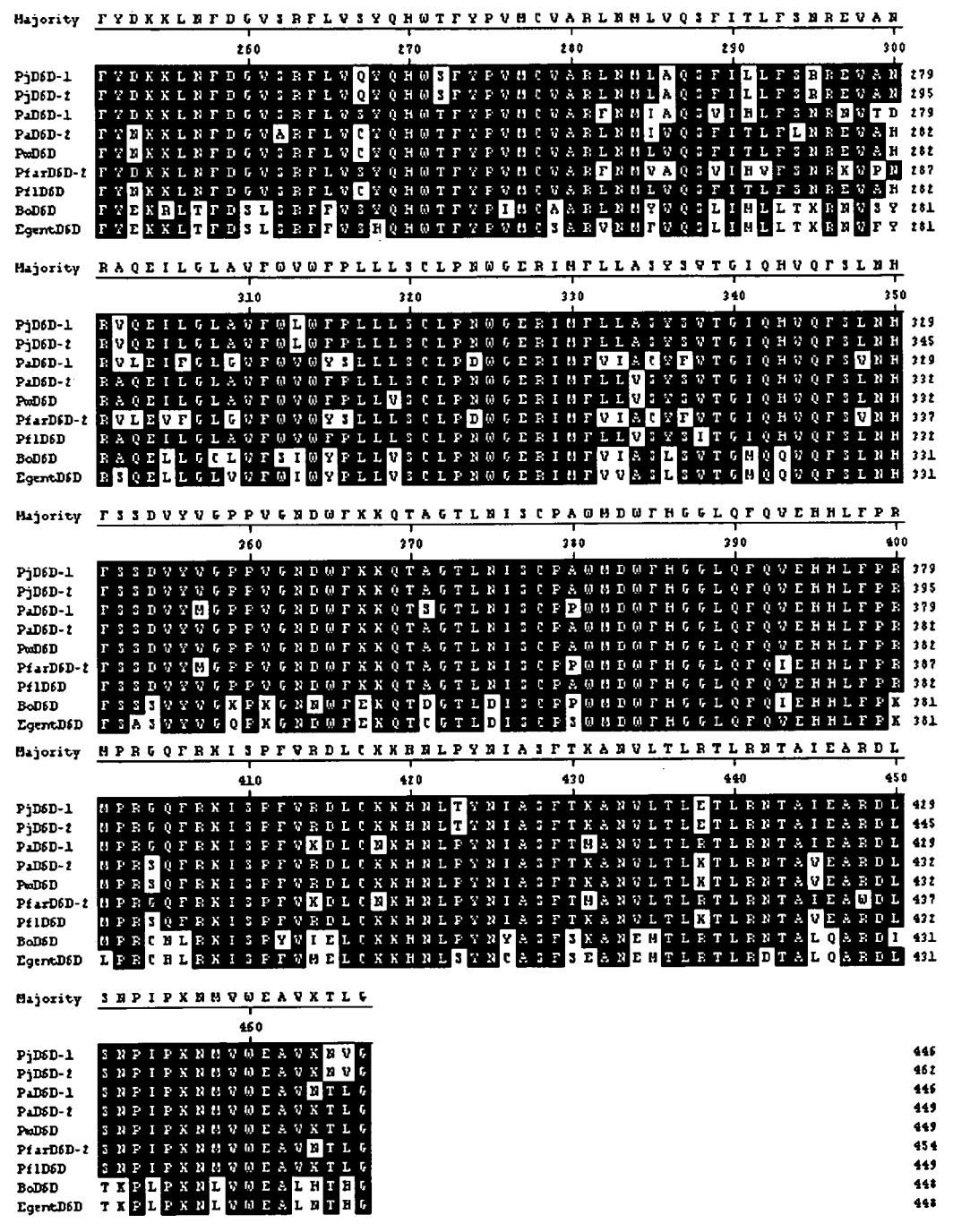

FIG. 1 shows alignment of *Primula juliae* Δ6 desaturases PjD6D-1 and PjD6D-2 (SEQ ID NOs:4 and 5), *Primula alpicola* Pa6D-1 and Pa6D-2 (SEQ ID NOs: 22 and 24), *Primula waltonii* PwD6D (SEQ ID NO:26), *Primula farinosa* D6D-2 (SEQ ID NO:46), *Primula florindae* D6D (SEQ ID NO:48), *Borago oficinalis* D6D (SEQ ID NO:59) and *Echium gentianoides* D6D (SEQ ID NO:60).

DETAILED DESCRIPTION OF THE INVENTION

Figure 2:
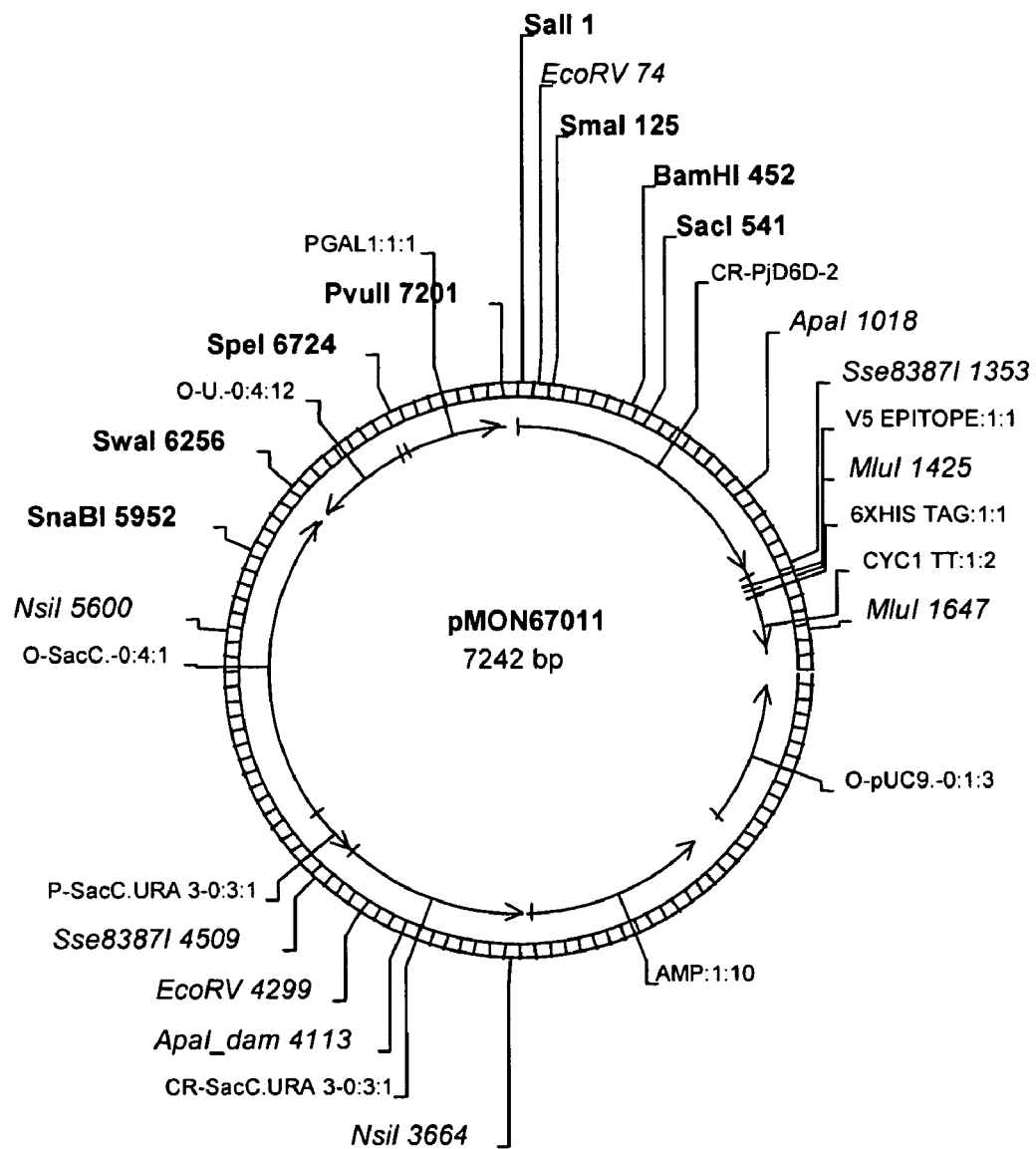
FIG. 2 shows map of vector pMON67011.

The invention overcomes the limitations of the prior art by providing methods and compositions for creation of plants with improved PUFA content. The modification of fatty acid content of an organism such as a plant presents many advantages, including improved nutrition and health benefits. Modification of fatty acid content can be used to achieve beneficial levels or profiles of desired PUFA's in plants, plant parts, and plant products, including plant seed oils. For example, when the desired PUFA's are produced in the seed tissue of a plant, the oil may be isolated from the seeds typically resulting in an oil high in desired PUFAs or an oil having a desired fatty acid content or profile, which may in turn be used to provide beneficial characteristics in food stuffs and other products. The invention in particular embodiments provides endogenous soybean oil having SDA while also containing a beneficial oleic acid content.

Various aspects of the invention include methods and compositions for modification of PUFA content of a cell, for example, modification of the PUFA content of a plant cell(s). Compositions related to the invention include novel isolated polynucleotide sequences, polynucleotide constructs and plants and/or plant parts transformed by polynucleotides of the invention. The isolated polynucleotide may encode *Primula* fatty acid desaturases and, in particular, may encode a *Primula* Δ6-desaturase. Host cells may be manipulated to express a polynucleotide encoding a desaturase polypeptide(s) which catalyze desaturation of a fatty acid(s).

Some aspects of the invention include desaturase polypeptides and polynucleotides encoding the same. Various embodiments of the invention may use combinations of desaturase polynucleotides and the encoded polypeptides that typically depend upon the host cell, the availability of substrate(s), and the desired end product(s). "Desaturase" refers to a polypeptide that can desaturate or catalyze formation of a double bond between consecutive carbons of one or more fatty acids to produce a mono- or poly-unsaturated fatty acid or a precursor thereof. Of particular interest are polypeptides that can catalyze the conversion of oleic acid to LA, LA to ALA, or ALA to SDA, which includes enzymes which desaturate at the 12, 15, or 6 positions. The term "polypeptide" refers to any chain of amino acids, regardless of length or post-translational modification (e.g., glycosylation or phosphorylation). Considerations for choosing a specific polypeptide having desaturase activity include, but are not limited to, the pH optimum of the polypeptide, whether the polypeptide is a rate limiting enzyme or a component thereof, whether the desaturase used is essential for synthesis of a desired PUFA, and/or whether a co-factor is required by the polypeptide. The expressed polypeptide preferably has characteristics that are compatible with the biochemical environment of its location in the host cell. For example, the polypeptide may have to compete for substrate(s).

Analyses of the $K_m$ and specific activity of a polypeptide in question may be considered in determining the suitability of a given polypeptide for modifying PUFA(s) production, level, or profile in a given host cell. The polypeptide used in a particular situation is one which typically can function under the conditions present in the intended host cell, but otherwise may be any desaturase polypeptide having a desired characteristic or being capable of modifying the relative production, level or profile of a desired PUFA(s) or any other desired characteristics as discussed herein. The substrate(s) for the expressed enzyme may be produced by the host cell or may be exogenously supplied. To achieve expression, the polypeptide(s) of the instant invention are encoded by polynucleotides as described below.

The inventors have isolated and produced enzymes from *Primula* that exhibit Δ6-desaturase activity. The sequences encoding the Δ6-desaturase may be expressed in transgenic plants, microorganisms or animals to effect greater synthesis of SDA. Other polynucleotides which are substantially identical to the Δ6-desaturase polynucleotides provided herein, or which encode polypeptides which are substantially identical to the Δ6-desaturase polypeptides, also can be used. "Substantially identical" refers to an amino acid sequence or nucleic acid sequence exhibiting in order of increasing preference at least 90%, 95%, 98 or 99% identity to the Δ6-desaturase polypeptide sequence in SEQ ID NO:4, SEQ ID NO:5, SEQ ID NO:22, SEQ ID NO:24, SEQ ID NO:26, SEQ ID NO:46 or SEQ ID NO:48 or sequences encoding these polypeptides. Polypeptide or polynucleotide comparisons may be carried out using sequence analysis software, for example, the Sequence Analysis software package of the GCG Wisconsin Package (Accelrys, San Diego, Calif.), MEGAlign (DNAStar, Inc., 1228 S. Park St., Madison, Wis. 53715), and MacVector (Oxford Molecular Group, 2105 S. Bascom Avenue, Suite 200, Campbell, Calif. 95008). Such software matches similar sequences by assigning degrees of similarity or identity.

Encompassed by the present invention are related desaturases, including variants of the disclosed Δ6-desaturases naturally occurring within the same or different species of *Primula*. Related desaturases can be identified by their ability to function substantially the same as the disclosed desaturases; that is, having Δ6-desaturase activity. Related desaturases also can be identified by screening sequence databases for sequences homologous to the disclosed desaturases, by hybridization of a probe based on the disclosed desaturases to a library constructed from the source organism, or by RT-PCR using mRNA from the source organism and primers based on the disclosed desaturases. The invention therefore provides nucleic acids hybridizing under stringent conditions to a desaturase coding sequences described herein. One of skill in the art understands that conditions may be rendered less stringent by increasing salt concentration and decreasing temperature. Thus, hybridization conditions can be readily manipulated, and thus will generally be a method of choice depending on the desired results. An example of high stringency conditions is 5×SSC, 50% formamide and 42° C. By conducting a wash under such conditions, for example, for 10 minutes, those sequences not hybridizing to a particular target sequence under these conditions can be removed.

In another aspect of the invention, vectors containing a nucleic acid, or fragment thereof, containing a promoter, a Δ6-desaturase coding sequence and a termination region may be transferred into an organism in which the promoter and termination regions are functional. Accordingly, organisms producing recombinant Δ6-desaturase are provided by this invention. Yet another aspect of this invention provides isolated Δ6-desaturase, which can be purified from the recombinant organisms by standard methods of protein purification. (For example, see Ausubel et al., 1994).

Various aspects of the invention include nucleic acid sequences that encode desaturases, described herein. Nucleic acids may be isolated from *Primula* including SEQ ID NO:2, SEQ ID NO:3, SEQ ID NO:21, SEQ ID NO:23, SEQ ID NO:25, SEQ ID NO:45 or SEQ ID NO:47 and the like. A cloning strategy based on oligonucleotide primers designed to amplify sequences identified as potential fatty acid desaturases, based on BLAST searches of genomic DNA databases, may be used to sequence individual clones. These clones may then be functionally characterized.

Nucleic acid constructs may be provided that integrate into the genome of a host cell or are autonomously replicated (e.g., episomally replicated) in the host cell. For production of ALA and/or SDA, the expression cassettes (i.e., a polynucleotide encoding a protein that is operatively linked to nucleic acid sequence(s) that directs the expression of the polynucleotide) generally used include an expression cassette which provides for expression of a polynucleotide encoding a Δ6-desaturase. In certain embodiments a host cell may have wild type oleic acid content.

Methods and compositions for the construction of expression vectors, when taken in light of the teachings provided herein, for expression of *Primula* desaturase enzymes will be apparent to one of ordinary skill in the art. Expression vectors, as described herein, are DNA or RNA molecules engineered for controlled expression of a desired polynucleotide, e.g., the Δ6-desaturase-encoding polynucleotide. Examples of vectors include plasmids, bacteriophages, cosmids or viruses. Shuttle vectors, e.g. (Wolk et al. 1984; Bustos et al., 1991) are also contemplated in accordance with the present invention. Reviews of vectors and methods of preparing and using them can be found in Sambrook et al. (2001); Goeddel (1990); and Perbal (1988). Sequence elements capable of effecting expression of a polynucleotide include promoters, enhancer elements, upstream activating sequences, transcription termination signals and polyadenylation sites.

Polynucleotides encoding desaturases may be placed under transcriptional control of a strong promoter. In some cases this leads to an increase in the amount of desaturase enzyme expressed and concomitantly an increase in the fatty acid produced as a result of the reaction catalyzed by the enzyme. There are a wide variety of plant promoter sequences which may be used to drive tissue-specific expression of polynucleotides encoding desaturases in transgenic plants. Indeed, in particular embodiments of the invention, the promoter used is a seed specific promoter. Examples of such promoters include the 5' regulatory regions from such genes as napin (Kridl et al., *Seed Sci. Res.* 1:209:219, 1991), phaseolin (Bustos, et al., *Plant Cell,* 1(9):839-853, 1989), soybean trypsin inhibitor (Riggs, et al., *Plant Cell* 1(6):609-621, 1989), ACP (Baerson et al., *Plant Mol. Biol.,* 22(2):255-267, 1993), stearoyl-ACP desaturase (Slocombe et al., *Plant Physiol.* 104(4):167-176, 1994), soybean a' subunit of β-conglycinin (P-Gm7S, see for example, Chen et al., *Proc. Natl. Acad. Sci.* 83:8560-8564, 1986), *Vicia faba* USP (P-Vf.Usp, see for example, SEQ ID NO:1, 2, and 3, U.S. patent application Ser. No. 10/429,516), the globulin promoter (see for example Belanger and Kriz, *Genet.* 129: 863-872 (1991), soybean alpha subunit of β-conglycinin (7S alpha) (U.S. patent application Ser. No. 10/235,618, incorporated by reference) and *Zea mays* L3 oleosin promoter (P-Zm.L3, see, for example, Hong et al., *Plant Mol. Biol.,* 34(3):549-555, 1997). Also included are the zeins, which are a group of storage proteins found in corn endosperm. Genomic clones for zein genes have been isolated (Pedersen et al., *Cell* 29:1015-1026 (1982), and Russell et al., *Transgenic Res.* 6(2):157-168) and the promoters from these clones, including the 15 kD, 16 kD, 19 kD, 22 kD, 27 kD and genes, could also be used.

The ordinarily skilled artisan can determine vectors and regulatory elements (including operably linked promoters and coding regions) suitable for expression in a particular host cell. "Operably linked" in this context means that the promoter and terminator sequences effectively function to regulate transcription. As a further example, a vector appropriate for expression of Δ6-desaturase in transgenic plants can comprise a seed-specific promoter sequence derived from helianthinin, napin, or glycinin operably linked to the Δ6-desaturase coding region and further operably linked to a seed storage protein termination signal or the nopaline synthase termination signal. As a still further example, a vector for use in expression of Δ6-desaturase in plants can comprise a constitutive promoter or a tissue specific promoter operably linked to the Δ6-desaturase coding region and further operably linked to a constitutive or tissue specific terminator or the nopaline synthase termination signal.

Modifications of the nucleotide sequences or regulatory elements disclosed herein which maintain the functions contemplated herein are within the scope of this invention. Such modifications include insertions, substitutions and deletions, and specifically substitutions which reflect the degeneracy of the genetic code.

Standard techniques for the construction of such recombinant vectors are well-known to those of ordinary skill in the art and can be found in references such as Sambrook et al. (2001), or any of the myriad of laboratory manuals on recombinant DNA technology that are widely available. A variety of strategies are available for ligating fragments of DNA, the choice of which depends on the nature of the termini of the DNA fragments. It is further contemplated in accordance with the present invention to include in a nucleic acid vector other nucleotide sequence elements which facilitate cloning, expression or processing, for example sequences encoding signal peptides, a sequence encoding KDEL, which is required for retention of proteins in the endoplasmic reticulum or sequences encoding transit peptides which direct Δ6-desaturase to the chloroplast. Such sequences are known to one of ordinary skill in the art. An optimized transit peptide is described, for example, by Van den Broeck et al. (1985). Prokaryotic and eukaryotic signal sequences are disclosed, for example, by Michaelis et al. (1982).

Polynucleotides encoding desired desaturases can be identified in a variety of ways. As an example, a source of the desired desaturase, for example genomic or cDNA libraries from *Primula*, is screened with detectable enzymatically- or chemically-synthesized probes, which can be made from DNA, RNA, or non-naturally occurring nucleotides, or mixtures thereof. Probes may be enzymatically synthesized from polynucleotides of known desaturases for normal or reduced-stringency hybridization methods. Oligonucleotide probes also can be used to screen sources and can be based on sequences of known desaturases, including sequences conserved among known desaturases, or on peptide sequences obtained from the desired purified protein. Oligonucleotide probes based on amino acid sequences can be degenerate to encompass the degeneracy of the genetic code, or can be biased in favor of the preferred codons of the source organism. Oligonucleotides also can be used as primers for PCR from reverse transcribed mRNA from a known or suspected source; the PCR product can be the full length cDNA or can be used to generate a probe to obtain the desired full length cDNA. Alternatively, a desired protein can be entirely sequenced and total synthesis of a DNA encoding that polypeptide performed.

Once the desired genomic or cDNA has been isolated, it can be sequenced by known methods. It is recognized in the art that such methods are subject to errors, such that multiple sequencing of the same region is routine and is still expected to lead to measurable rates of mistakes in the resulting deduced sequence, particularly in regions having repeated domains, extensive secondary structure, or unusual base compositions, such as regions with high GC base content. When discrepancies arise, resequencing can be done and can employ special methods. Special methods can include altering sequencing conditions by using: different temperatures; different enzymes; proteins which alter the ability of oligonucleotides to form higher order structures; altered nucleotides such as ITP or methylated dGTP; different gel compositions, for example adding formamide; different primers or primers located at different distances from the problem region; or different templates such as single stranded DNAs. Sequencing of mRNA also can be employed.

Some or all of the coding sequence for a polypeptide having desaturase activity may be from a natural source. In some situations, however, it is desirable to modify all or a portion of the codons, for example, to enhance expression, by employing host preferred codons. Host-preferred codons can be determined from the codons of highest frequency in the proteins expressed in the largest amount in a particular host species and/or tissue of interest. Thus, the coding sequence for a polypeptide having desaturase activity can be synthesized in whole or in part. All or portions of the DNA also can be synthesized to remove any destabilizing sequences or regions of secondary structure which would be present in the transcribed mRNA. All or portions of the DNA also can be synthesized to alter the base composition to one more preferable in the desired host cell. Methods for synthesizing sequences and bringing sequences together are well established in the literature. In vitro mutagenesis and selection, site-directed mutagenesis, or other means can be employed to obtain mutations of naturally-occurring desaturase genes to produce a polypeptide having desaturase activity in vivo with more desirable physical and kinetic parameters for function in the host cell, such as a longer half-life or a higher rate of production of a desired polyunsaturated fatty acid.

Once the polynucleotide encoding a desaturase polypeptide has been obtained, it is placed in a vector capable of replication in a host cell, or is propagated in vitro by means of techniques such as PCR or long PCR. Replicating vectors can include plasmids, phage, viruses, cosmids and the like. Desirable vectors include those useful for mutagenesis of the gene of interest or for expression of the gene of interest in host cells. The technique of long PCR has made in vitro propagation of large constructs possible, so that modifications to the gene of interest, such as mutagenesis or addition of expression signals, and propagation of the resulting constructs can occur entirely in vitro without the use of a replicating vector or a host cell.

For expression of a desaturase polypeptide, functional transcriptional and translational initiation and termination regions are operably linked to the polynucleotide encoding the desaturase polypeptide. Expression of the polypeptide coding region can take place in vitro or in a host cell. Transcriptional and translational initiation and termination regions are derived from a variety of nonexclusive sources, including the polynucleotide to be expressed, genes known or suspected to be capable of expression in the desired system, expression vectors, chemical synthesis, or from an endogenous locus in a host cell.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

When increased expression of the desaturase polypeptide in the source organism is desired, several methods can be employed. Additional genes encoding the desaturase polypeptide can be introduced into the host organism. Expression from the native desaturase locus also can be increased through homologous recombination, for example by inserting a stronger promoter into the host genome to cause increased expression, by removing destabilizing sequences from either the mRNA or the encoded protein by deleting that information from the host genome, or by adding stabilizing sequences to the mRNA (U.S. Pat. No. 4,910,141).

It is contemplated that more than one polynucleotide encoding a desaturase or a polynucleotide encoding more than one desaturase may be introduced and propagated in a host cell through the use of episomal or integrated expression vectors. Where two or more genes are expressed from separate replicating vectors, it is desirable that each vector has a different means of replication. Each introduced construct, whether integrated or not, should have a different means of selection and should lack homology to the other constructs to maintain stable expression and prevent reassortment of elements among constructs. Judicious choices of regulatory regions, selection means and method of propagation of the introduced construct can be experimentally determined so that all introduced polynucleotides are expressed at the necessary levels to provide for synthesis of the desired products.

When necessary for transformation, the Δ6-desaturase coding sequences of the present invention can be inserted into a plant transformation vector, e.g. the binary vector described by Bevan (1984). Plant transformation vectors can be derived by modifying the natural gene transfer system of *Agrobacterium tumefaciens*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In the modified binary vectors the tumor-inducing genes have been deleted and the functions of the vir region are utilized to transfer foreign DNA bordered by the T-DNA border sequences. The T-region also contains a selectable marker for antibiotic resistance, and a multiple cloning site for inserting sequences for transfer. Such engineered strains are known as "disarmed" *A. tumefaciens* strains, and allow the efficient transformation of sequences bordered by the T-region into the nuclear genomes of plants.

The subject invention finds many applications. Probes based on the polynucleotides of the present invention may find use in methods for isolating related molecules or in methods to detect organisms expressing desaturases. When used as probes, the polynucleotides or oligonucleotides must be detectable. This is usually accomplished by attaching a label either at an internal site, for example via incorporation of a modified residue, or at the 5' or 3' terminus. Such labels can be directly detectable, can bind to a secondary molecule that is detectably labeled, or can bind to an unlabelled secondary molecule and a detectably labeled tertiary molecule; this process can be extended as long as is practical to achieve a satisfactorily detectable signal without unacceptable levels of background signal. Secondary, tertiary, or bridging systems can include use of antibodies directed against any other molecule, including labels or other antibodies, or can involve any molecules which bind to each other, for example a biotin-streptavidin/avidin system. Detectable labels typically include radioactive isotopes, molecules which chemically or enzymatically produce or alter light, enzymes which produce detectable reaction products, magnetic molecules, fluorescent molecules or molecules whose fluorescence or light-emitting characteristics change upon binding. Examples of labeling methods can be found in U.S. Pat. No. 5,011,770. Alternatively, the binding of target molecules can be directly detected by measuring the change in heat of solution on binding of probe to target via isothermal titration calorimetry, or by coating the probe or target on a surface and detecting the change in scattering of light from the surface produced by binding of target or probe, respectively, as may be done with the BIAcore system.

Constructs comprising the gene of interest may be introduced into a host cell by standard techniques. For convenience, a host cell which has been manipulated by any method to take up a DNA sequence or construct will be referred to as "transformed" or "recombinant" herein. The subject host will have at least have one copy of the expression construct and may have two or more, for example, depending upon whether the gene is integrated into the genome, amplified, or is present on an extrachromosomal element having multiple copy numbers.

The transformed host cell can be identified by selection for a marker contained on the introduced construct. Alternatively, a separate marker construct may be introduced with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene therefore may confer antibiotic resistance, or encode an essential growth factor or enzyme, and permit growth on selective media when expressed in the transformed host. Selection of a transformed host can also occur when the expressed marker protein can be detected, either directly or indirectly. The marker protein may be expressed alone or as a fusion to another protein. The marker protein can be detected by its enzymatic activity; for example, beta-galactosidase can convert the substrate X-gal to a colored product, and luciferase can convert luciferin to a light-emitting product. The marker protein can be detected by its light-producing or modifying characteristics; for example, the green fluorescent protein of *Aequorea victoria* fluoresces when illuminated with blue light. Antibodies can be used to detect the marker protein or a molecular tag on, for example, a protein of interest. Cells expressing the marker protein or tag can be selected, for example, visually, or by techniques such as FACS or panning using antibodies. Desirably, resistance to kanamycin and the amino glycoside G418 are of interest, as well as ability to grow on media lacking uracil, leucine, lysine or tryptophan.

Of particular interest is the Δ6-desaturase-mediated production of PUFA's in eukaryotic host cells. Eukaryotic cells include plant cells, such as those from oil-producing crop plants, and other cells amenable to genetic manipulation including fungal cells. The cells may be cultured or formed as part or all of a host organism including a plant. In a preferred embodiment, the host is a plant cell which produces and/or can assimilate exogenously supplied substrate(s) for a Δ6-desaturase, and preferably produces large amounts of one or more of the substrates.

The transformed host cell is grown under appropriate conditions adapted for a desired end result. For host cells grown in culture, the conditions are typically optimized to produce the greatest or most economical yield of PUFA's, which relates to the selected desaturase activity. Media conditions which may be optimized include: carbon source, nitrogen source, addition of substrate, final concentration of added substrate, form of substrate added, aerobic or anaerobic growth, growth temperature, inducing agent, induction temperature, growth phase at induction, growth phase at harvest, pH, density, and maintenance of selection.

Another aspect of the present invention provides transgenic plants or progeny of plants containing the isolated DNA of the invention. Both monocotyledonous and dicotyledonous plants are contemplated. Plant cells are transformed with an isolated DNA encoding Δ6-desaturase by any plant transformation method. The transformed plant cell, often in a callus culture or leaf disk, is regenerated into a complete transgenic plant by methods well-known to one of ordinary skill in the art (e.g. Horsch et al., 1985). In one embodiment, the transgenic plant is selected from the group consisting of *Arabidopsis thaliana*, canola, soy, soybean, rapeseed, sunflower, cotton, cocoa, peanut, safflower, coconut, flax, oil palm, oilseed *Brassica napus*, corn, jojoba, Chinese tallow tree, tobacco, fruit plants, citrus plants or plants producing nuts and berries. Since progeny of transformed plants inherit the polynucleotide encoding Δ6-desaturase, seeds or cuttings from transformed plants may be used to maintain the transgenic plant line.

The present invention further provides a method for providing transgenic plants with an increased content of ALA and/or SDA. This method includes, for example, introducing DNA encoding Δ6-desaturase into plant cells which lack or have low levels SDA but contain ALA, and regenerating plants with increased SDA content from the transgenic cells. In certain embodiments of the invention, a DNA encoding a Δ15- and/or Δ12-desaturase may also be introduced into the plant cells. Such plants may or may not also comprise endogenous Δ12- and/or Δ15-desaturase activity. In certain embodiments, modified commercially grown crop plants are contemplated as the transgenic organism, including, but not limited to, *Arabidopsis thaliana*, canola, soy, soybean, rapeseed, sunflower, cotton, cocoa, peanut, safflower, coconut, flax, oil palm, oilseed *Brassica napus*, corn, jojoba, Chinese tallow tree, tobacco, fruit plants, citrus plants or plants producing nuts and berries.

The present invention further provides a method for providing transgenic plants which may contain elevated levels of ALA and/or SDA, wherein said elevated levels are greater than levels found in non-transformed plants. Expression vectors comprising DNA encoding a Δ6-desaturase, and/or a Δ12-desaturase and/or a Δ15-desaturase, can be constructed by methods of recombinant technology known to one of ordinary skill in the art (Sambrook et al., 2001). In particular, commercially grown crop plants are contemplated as the transgenic organism, including, but not limited to, *Arabidopsis thaliana*, canola, soy, soybean, rapeseed, sunflower, cotton, cocoa, peanut, safflower, coconut, flax, oil palm, oilseed *Brassica napus*, and corn.

For dietary supplementation, the purified PUFAs, transformed plants or plant parts, or derivatives thereof, may be incorporated into cooking oils, fats or margarines formulated so that in normal use the recipient would receive the desired amount. The PUFAs may also be incorporated into infant formulas, nutritional supplements or other food products, and may find use as anti-inflammatory or cholesterol lowering agents.

As used herein, "edible composition" is defined as compositions which may be ingested by a mammal such as foodstuffs, nutritional substances and pharmaceutical compositions. As used herein "foodstuffs" refer to substances that can be used or prepared for use as food for a mammal and include substances that may be used in the preparation of food (such as frying oils) or food additives. For example, foodstuffs include animals used for human consumption or any product therefrom, such as, for example, eggs. Typical foodstuffs include but are not limited to beverages, (e.g., soft drinks, carbonated beverages, ready to mix beverages), infused foods (e.g. fruits and vegetables), sauces, condiments, salad dressings, fruit juices, syrups, desserts (e.g., puddings, gelatin, icings and fillings, baked goods and frozen desserts such as ice creams and sherbets), soft frozen products (e.g., soft frozen creams, soft frozen ice creams and yogurts, soft frozen toppings such as dairy or non-dairy whipped toppings), oils and emulsified products (e.g., shortening, margarine, mayonnaise, butter, cooking oil, and salad dressings) and intermediate moisture foods (e.g., rice and dog foods).

Furthermore, edible compositions described herein can also be ingested as an additive or supplement contained in foods and drinks. These can be formulated together with a nutritional substance such as various vitamins and minerals and incorporated into substantially liquid compositions such as nutrient drinks, soymilks and soups; substantially solid compositions; and gelatins or used in the form of a powder to be incorporated into various foods. The content of the effective ingredient in such a functional or health food can be similar to the dose contained in a typical pharmaceutical agent.

The purified PUFAs, transformed plants or plant parts may also be incorporated into animal, particularly livestock, feed. In this way, the animals themselves may benefit from a PUFA rich diet, while human consumers of food products produced from such livestock may benefit as well. It is expected in certain embodiments that SDA will be converted to EPA in animals and thus such animals may benefit from an increase in EPA by consumption of SDA.

For pharmaceutical use (human or veterinary), the compositions may generally be administered orally but can be administered by any route by which they may be successfully absorbed, e.g., parenterally (i.e. subcutaneously, intramuscularly or intravenously), rectally, vaginally or topically, for example, as a skin ointment or lotion. The PUFAs transformed plants or plant parts of the present invention may be administered alone or in combination with a pharmaceutically acceptable carrier or excipient. Where available, gelatin capsules are the preferred form of oral administration. Dietary supplementation as set forth above can also provide an oral route of administration. The unsaturated acids of the present invention may be administered in conjugated forms, or as salts, esters, amides or prodrugs of the fatty acids. Any pharmaceutically acceptable salt is encompassed by the present invention; especially preferred are the sodium, potassium or lithium salts. Also encompassed are the N-alkylpolyhydroxamine salts, such as N-methyl glucamine, found in PCT publication WO 96/33155. The preferred esters are the ethyl esters. As solid salts, the PUFAs also can be administered in tablet form. For intravenous administration, the PUFAs or derivatives thereof may be incorporated into commercial formulations such as Intralipids.

If desired, the regions of a desaturase polypeptide important for desaturase activity can be determined through routine mutagenesis followed by expression of the resulting mutant polypeptides and determination of their activities. Mutants may include substitutions, deletions, insertions and point mutations, or combinations thereof. Substitutions may be made on the basis of conserved hydrophobicity or hydrophilicity (Kyte and Doolittle, 1982), or on the basis of the ability to assume similar polypeptide secondary structure (Chou and Fasman, 1978). A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites.

Internal deletions can similarly be made through a variety of methods including the use of existing restriction sites in the DNA, by use of mutagenic primers via site directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR. Chemical mutagenesis may also be used for identifying regions of a desaturase polypeptide important for activity. Such structure-function analysis can determine which regions may be deleted, which regions tolerate insertions, and which point mutations allow the mutant protein to function in substantially the same way as the native desaturase. All such mutant proteins and nucleotide sequences encoding them are within the scope of the present invention.

As described herein above, certain embodiments of the current invention concern plant transformation constructs. For example, one aspect of the current invention is a plant transformation vector comprising one or more desaturase gene(s) or cDNA(s). Exemplary coding sequences for use with the invention include *Primula juliae* Δ6-desaturase (SEQ ID NOs:2-3). In certain embodiments, antisense desaturase sequences can also be employed with the invention. Exemplary desaturase encoding nucleic acids include at least 20, 40, 80, 120, 300 and up to the full length of the nucleic acid sequences of SEQ ID NO:2, SEQ ID NO:3, SEQ ID NO:21, SEQ ID NO:23, SEQ ID NO:25, SEQ ID NO:45 or SEQ ID NO:47. In certain aspects, a nucleic acid may encode 1, 2, 3, 4, or more desaturase enzymes. In particular embodiments, a nucleic acid may encode a Δ6- and a Δ15-desaturase.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce various desaturase encoding nucleic acids. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al. (1996).

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

In one embodiment the instant invention utilizes certain promoters. Examples of such promoters that may be used with the instant invention include, but are not limited to, the 35S CaMV (cauliflower mosaic virus), 34S FMV (figwort mosaic virus) (see, e.g., U.S. Pat. No. 5,378,619, the contents of which are herein incorporated in their entirety), Napin (from *Brassica*), 7S (from soybean), Globulin and Lec (from corn). The napin promoter and promoters, which are regulated during plant seed maturation, are of particular interest for use with the instant invention. All such promoter and transcriptional regulatory elements, singly or in combination, are contemplated for use in the present replicable expression vectors and are known to one of ordinary skill in the art.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

Transformation constructs prepared in accordance with the invention will typically include a 3' end DNA sequence that acts as a signal to terminate transcription and allow for the poly-adenylation of the mRNA produced by coding sequences operably linked to a desaturase gene (e.g., cDNA). In one embodiment of the invention, the native terminator of a desaturase gene is used. Alternatively, a heterologous 3' end may enhance the expression of desaturase coding regions. Examples of terminators deemed to be useful include those from the nopaline synthase gene of *Agrobacterium tumefaciens* (nos 3' end) (Bevan et al., 1983), the terminator for the T7 transcript from the octopine synthase gene of *Agrobacterium tumefaciens*, the 3' end of the protease inhibitor I or II genes from potato or tomato and the CaMV 35S terminator (tml3'). Regulatory elements such as an Adh intron (Callis et al., 1987), sucrose synthase intron (Vasil et al., 1989) or TMV omega element (Gallie et al., 1989), may further be included where desired.

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Suitable methods for transformation of plant or other cells for use with the current invention are believed to include virtually any method by which DNA can be introduced into a cell, such as by direct delivery of DNA such as by PEGmediated transformation of protoplasts (Omirulleh et al., 1993), by desiccation/inhibition-mediated DNA uptake (Potrykus et al., 1985), by electroporation (U.S. Pat. No. 5,384, 253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464, 765, specifically incorporated herein by reference in its entirety), by Agrobacterium-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, typically at least 2 weeks, then transferred to media conducive to maturation of embryoids. Cultures are transferred every 2 weeks on this medium. Shoot development will signal the time to transfer to medium lacking growth regulators.

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

In addition to direct transformation of a particular plant genotype with a construct prepared according to the current invention, transgenic plants may be made by crossing a plant having a selected DNA of the invention to a second plant lacking the DNA. Plant breeding techniques may also be used to introduce a multiple desaturases, for example Δ6, Δ12, and/or Δ15-desaturase(s) into a single plant. In this manner, Δ6-desaturase can be effectively up-regulated. By creating plants homozygous for a Δ6-desaturase activity and/or other desaturase activity (e.g., Δ12- and/or Δ15-desaturase activity) beneficial metabolites can be increased in the plant.

As set forth above, a selected desaturase gene can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes or alleles relative to a starting plant line, as disclosed herein, is defined as the techniques that result in a particular sequence being introduced into a plant line by crossing a starting line with a donor plant line that comprises a transgene or allele of the invention. To achieve this one could, for example, perform the following steps: (a) plant seeds of the first (starting line) and second (donor plant line that comprises a desired transgene or allele) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower.

Backcrossing is herein defined as the process including the steps of: (a) crossing a plant of a first genotype containing a desired gene, DNA sequence or element to a plant of a second genotype lacking said desired gene, DNA sequence or element; (b) selecting one or more progeny plant containing the desired gene, DNA sequence or element; (c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention.

More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Cloning of Primula juliae Δ6 Desaturase Sequences

Cloning of the *Primula juliae* Δ6 desaturase (PjD6D) was achieved by PCR amplification of a partial internal genomic DNA region using degenerate oligonucleotides, followed by bi-directional genomic walking. Total genomic DNA was isolated from *P. juliae* (Collector's Nursery, Battleground Wash.) using the DNeasy Plant Mini Kit (Qiagen, Valencia, Calif.), following the manufacturer's procedure. Initially, a 552 bp fragment corresponding to positions 687 to 1238 of SEQ ID NO:1 was isolated using degenerate oligonucleotides BO-1 For and BO-2 Rev as described by Garcia-Maroto et al. (2002). The fragment was cloned into pCR®4-TOPO® (Invitrogen, Carlsbad, Calif.) to yield the vector pMON83955 and the insert was sequenced. Primer sequences BO-1 For and BO-2 Rev were as follows:

```
BO-1 For:
5'-ATMAGYATYGGTTGGTGGAARTGG-3'        (SEQ ID NO: 6)

BO-2 Rev:
5'-AATCCACCRTGRAACCARTCCAT-3'         (SEQ ID NO: 7)
```

To determine the genomic flanking sequence of the insert of pMON83955, a Universal Genome Walker Kit™ (BD Biosciences, Palo Alto, Calif.) was utilized, following the manufacture's procedure. Four *P. juliae* genomic libraries were generated by digesting the DNA with four restriction enzymes: EcoRV, PvuII, StuI, and DraI. After a purification step, the digestions were ligated to an adapter provided in the kit. The procedure then involved two PCR reactions, each with a gene-specific primer and an adapter-primer. The secondary PCR reaction used a dilution of the primary PCR reaction products as a template. For the 5' direction, primers PD6D R8 and PD6D R2 were used for the primary and secondary PCR reactions, respectively. For the 3' direction, primers PD6D F8 and PD6D F3 were used for the primary and secondary PCR reactions, respectively. The primer sequences are given below:

```
PD6D R8:
5'-CACACATGACCGGATAAAACGACCAGT-3'      (SEQ ID NO: 8)

PD6D R2:
5'-GGGAATGTACTGGAGGTCAGGGTCGTA-3'      (SEQ ID NO: 9)

PD6D F8:
5'-CGTGCAGTTCAGCTTGAACCATTTCTC-3'      (SEQ ID NO: 10)

PD6D F3:
5'-TGCAGGGACACTCAACATATCGTGCCC-3'      (SEQ ID NO: 11)
```

Genome walking in the 5' direction yielded a 574 bp fragment from the EcoRV library. This product Was cloned into pCR®4-TOPO® (Invitrogen) giving pMON83956, and the insert was sequenced. The resulting sequence did not contain a start codon of the putative delta 6 desaturase gene and thus another set of PCR reactions was performed using gene specific primers designed to walk in the 5' direction from the pMON83956 insert. The primers used for the second genome walking set in the 5' direction were PD6D R15 and PD6D R14 for the primary and secondary PCR reactions, respectively. The sequences are given below:

```
PD6D R15:
5'-GTAGGTTGGTGGAGAAGGGAGGGAGGA-3'      (SEQ ID NO: 12)

PD6D R14:
5'-GGAAGGGGATGGTAAGCGAGGAAAGC-3'       (SEQ ID NO: 13)
```

A product of 328 bp in length from the StuI library was cloned into pCR4®-TOPO®(Invitrogen) giving pMON83958 and the insert was sequenced. This insert contained 2 potential start codons, 44 bases apart. The first start codon corresponds to position 87 and the second to position 135 of SEQ ID NO:1. Genome walking in the 3' direction resulted in a 773 bp fragment from the DraI library. This product was cloned into pCR®4-TOPO®, giving pMON83957. The insert was sequenced and found to contain 292 bp of the coding region for the putative delta 6 desaturase gene, followed by a stop codon at position 1473 with respect to SEQ ID NO:1.

The inserts of pMON83955, pMON83956, pMON83957, and pMON83958 were aligned to form a composite sequence, SEQ ID NO:1. Three primers were designed to PCR amplify 2 different lengths of coding sequence from *P. juliae* genomic DNA, reflecting the two start codons found in pMON83958. The longer of the two sequences, PjD6D-1, was amplified using forward primer Pj D6D F2 and reverse primer Pj D6D R1. The shorter of the two, PjD6D-2, was amplified using forward primer Pj D6D F1 and reverse primer Pj D6D R1. The two putative delta 6 desaturase coding sequences were each then ligated into the yeast expression vector pYES2.1-TOPO. Upon sequencing, the plasmid containing PjD6D-1 was designated pMON83950 (SEQ ID NO:3) and the plasmid containing PjD6D-2 was designated pMON67011 (SEQ ID NO:2). The primer sequences are given below:

```
Pj D6D F2:  5'-GTCGACATGGAAAACACATTTTCACCACCACCT-3'    (SEQ ID NO: 14)

Pj D6D F1:  5'-GTCGACATGACTAAGACGATTTACATAACCAGC-3'    (SEQ ID NO: 15)

Pj D6D R1:  5'-CCTGCAGGTCACCCGACATTTTTAACAGCCTCCC-3'   (SEQ ID NO: 16)
```

The two PjΔ6 desaturase clones, PjD6D-2 and PjD6D-1, encode potential polypeptides of 446 amino acids and 462 amino acids, given in SEQ ID NO:4 and SEQ ID NO:5, respectively. The initial MET site of the shorter peptide sequence (PjD6D-2) is located 16 amino acids downstream from the first MET site of the longer sequence (PjD6D-1). 3' of the second MET, the sequences are identical. These sequences have high similarity to other plant Δ6 desaturases (FIG. 1), including an N-terminal cytochrome $b_5$ domain which is found in all front-end desaturases (Napier et al., 2003). Within the cytochrome $b_5$ domain is found the eight invariant residues characteristic of the cytochrome $b_5$ superfamily and the H-P-G-G heme-binding motif, which has been shown to be essential for enzymatic activity (Napier et al., 1997, Sayanova et al, 1999, Sperling and Heinz 2001). Within the desaturase domain of the putative PjD6D desaturase are three conserved histidine boxes that are characteristic of all membrane-bound desaturases (Shanklin et al., 1994). A distinguishing feature found in all front-end desaturases is that the third histidine box contains a glutamine residue in the first position (Q-x-x-H-H) instead of a histidine (Napier et al., 1997, Napier et al., 2003, Sperling and Heinz 2001). The deduced amino acid sequence of the PjD6D had approximately 88% identity to the *Primula vialii* and *P. farinosa* desaturases and approximately 64% identity to the *Echium pitardii* and *E. gentianoides* desaturases. Visual inspection of the multiple sequence alignment shown in FIG. 1 suggests that the *P. juliae* Δ6 desaturase sequence does not contain any introns. This has been observed in Δ6 desaturases from *Primula* and *Echium* species (Sayanova et al., 2003, Garcia-Maroto et al., 2002).

Example 2

Yeast Transformation and Expression

Figure 3:
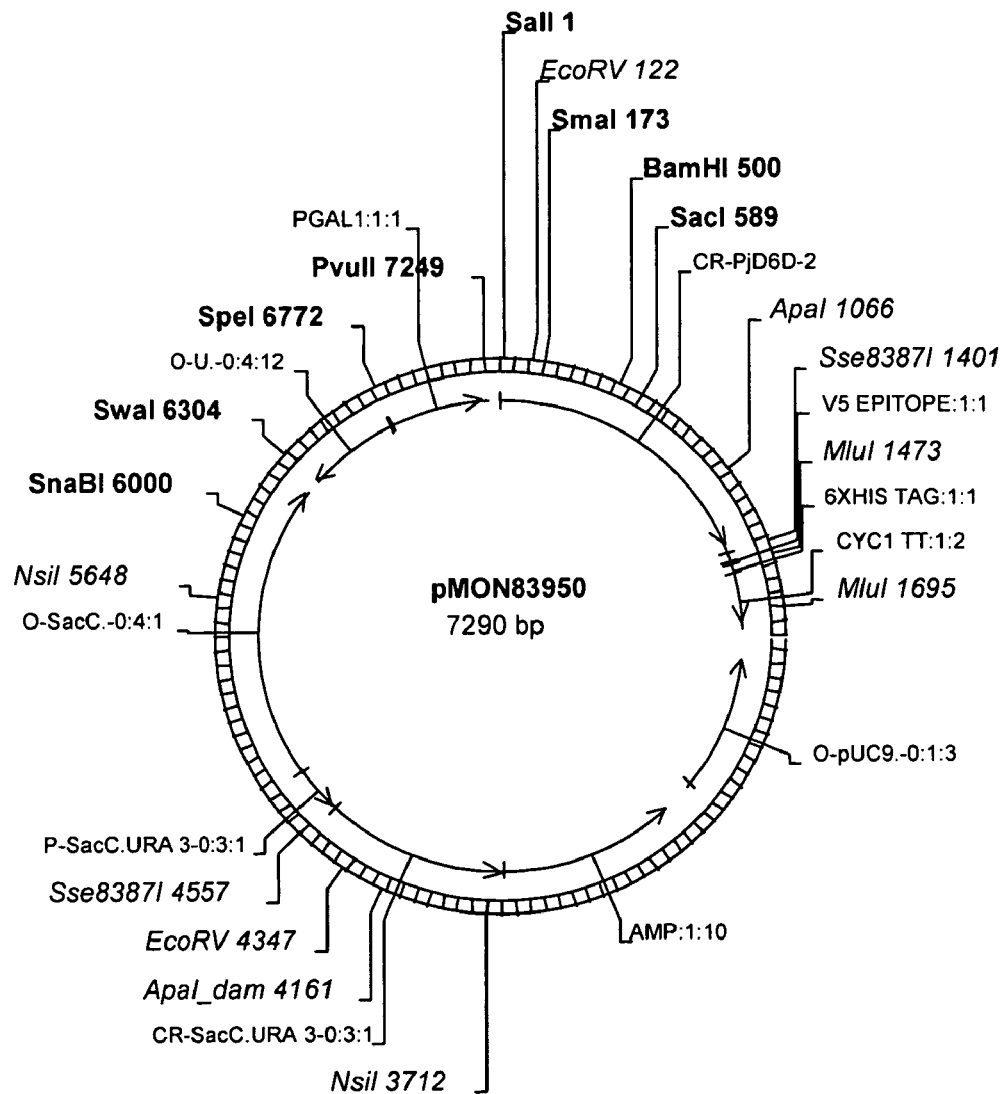
FIG. 3 shows map of vector pMON83950.

Constructs pMON83950 (FIG. 3) and pMON67011 (FIG. 2) were introduced into the host strain *Saccharomyces cerevisiae* INVSc1 (Invitrogen), which is auxotrophic for uracil, using the PEG/Li Ac protocol as described in the Invitrogen manual for pYES2.1/V5-His-TOPO. Transformants were selected on plates made of SC minimal media minus uracil with 2% glucose. Colonies of transformants were used to inoculate 5 ml of SC minimal media minus uracil and 2% glucose and were grown overnight at 30° C. For induction, stationary phase yeast cells were pelleted and re-suspended in SC minimal media minus uracil supplemented with 2% galactose and grown for 3 days at 15° C. When exogenous fatty acids were provide to the cultures, 0.01% LA (Δ9,12-18:2) was added with the emulsifier 0.1% Tergitol. The cultures were grown for 3 days at 15° C., and subsequently harvested by centrifugation. Cell pellets were washed once with sterile TE buffer pH 7.5, to remove the media, and lyophilized for 24 h. The host strain transformed with the vector containing the LacZ gene was used as a negative control in all studies.

Lipids were extracted from lyophilized yeast pellets by adding 0.1 mL toluene and incubating over night at room temperature. Extracted lipids were converted to fatty acid methyl esters (FAMEs) in situ by addition of 0.5 mL 0.6N sodium methoxide in methanol and incubating for 45 min. The FAMEs were extracted by addition of 0.8 mL 10% (w/v) NaCl and 0.15 mL of heptane. The heptane layer containing FAMEs was removed and used directly for gas chromatography (GC). The FAMEs were identified on a Hewlett-Packard 5890 II Plus GC (Hewlett-Packard, Palo Alto, Calif.) equipped with a flame-ionization detector and a capillary column (omegawax 250; 30 m×0.25 mm i.d.×0.25 μm; Supelco, Bellefonte, Pa.). A 100:1 split ratio was used for injections. The injector was maintained at 250° C. and the flame ionization detector was maintained at 270° C. The column temperature was maintained at 180° C. for 1.5 min following injection, increased to 240° C. at 40° C./min, and held at 245° C. for 3.38 min.

Table 1 shows the fatty acid composition for yeast expressing *P. juliae* clones pMON67011 (PjD6D-2), pMON83950 (PjD6D-1) or *Mortierella alpina* Δ6 desaturase, pMON77205. Expected products for Δ6 desaturation of LA and ALA were observed for both *P. juliae* clones (Table 1, GLA and SDA, respectively), demonstrating that the clones contained in pMON67011 and pMON83950 are 06 desaturases. The substrate selectivity was determined by feeding equal quantities of LA and ALA. *M. alpina* is a filamentous fungus that accumulates high levels of the n-6 fatty acid arachidonic acid and was expected to have a Δ6 desaturase with an n-6 selectivity. Table 2 shows the n-3:n-6 substrate selectivities of the *P. juliae* and *M. alpina* Δ6 desaturases. An n-3:n-6 selectivity of ~0.8 was observed for the *M. alpina* Δ6 desaturase. An n-3:n-6 selectivity of ~1.5-1.9 was observed for both *P. juliae* Δ6 desaturase clones.

TABLE 1

Comparison of fatty acid composition of yeast expressing different Δ6 desaturases

| Vector | Gene | FA in medium | LA* | GLA* | ALA* | SDA* |
| --- | --- | --- | --- | --- | --- | --- |
| pMON67011 | *P. juliae* D6D-2 | — | 2.0 | 0.0 | 0.0 | 0.0 |
| pMON67011 | *P. juliae* D6D-2 | — | 2.5 | 0.0 | 0.1 | 0.0 |
| pMON67011 | *P. juliae* D6D-2 | LA | 25.7 | 14.0 | 0.0 | 0.0 |
| pMON67011 | *P. juliae* D6D-2 | LA | 28.4 | 16.8 | 0.1 | 0.0 |
| pMON67011 | *P. juliae* D6D-2 | ALA | 0.3 | 0.1 | 24.4 | 16.8 |
| pMON67011 | *P. juliae* D6D-2 | ALA | 0.3 | 0.1 | 30.6 | 19.0 |
| pMON67011 | *P. juliae* D6D-2 | LA + ALA | 22.7 | 6.0 | 18.0 | 8.5 |
| pMON67011 | *P. juliae* D6D-2 | LA + ALA | 24.3 | 5.8 | 20.4 | 8.9 |
| pMON83950 | *P. juliae* D6D-1 | — | 2.3 | 0.0 | 0.3 | 0.0 |
| pMON83950 | *P. juliae* D6D-1 | — | 2.3 | 0.0 | 0.2 | 0.0 |
| pMON83950 | *P. juliae* D6D-1 | LA | 26.3 | 15.0 | 0.0 | 0.0 |
| pMON83950 | *P. juliae* D6D-1 | LA | 23.5 | 16.6 | 0.0 | 0.0 |
| pMON83950 | *P. juliae* D6D-1 | ALA | 0.6 | 0.2 | 37.3 | 17.5 |
| pMON83950 | *P. juliae* D6D-1 | ALA | 0.7 | 0.1 | 33.9 | 17.4 |
| pMON83950 | *P. juliae* D6D-1 | LA + ALA | 18.8 | 4.3 | 17.1 | 9.4 |
| pMON83950 | *P. juliae* D6D-1 | LA + ALA | 16.9 | 4.8 | 15.7 | 9.8 |
| pMON77205 | *M. alpina* D6D | — | 1.7 | 0.0 | 0.2 | 0.0 |
| pMON77205 | *M. alpina* D6D | — | 1.0 | 0.0 | 0.0 | 0.0 |
| pMON77205 | *M. alpina* D6D | LA | 56.8 | 6.0 | 0.0 | 0.0 |
| pMON77205 | *M. alpina* D6D | LA | 25.4 | 4.6 | 0.2 | 0.0 |
| pMON77205 | *M. alpina* D6D | ALA | 0.5 | 0.0 | 69.2 | 2.6 |
| pMON77205 | *M. alpina* D6D | ALA | 0.9 | 0.0 | 23.0 | 5.0 |
| pMON77205 | *M. alpina* D6D | LA + ALA | 34.8 | 1.3 | 39.7 | 1.1 |
| pMON77205 | *M. alpina* D6D | LA + ALA | 18.7 | 2.8 | 18.4 | 2.2 |

**Reported as a % of the total for all analytes included in the GC-FID chromatogram, including but not shown (16:0, 16:1, 18:0, 20:0, 20:1, 20:2, 22:0, 22:1, 22:2

TABLE 2

Comparison of n-3:n-6 substrate selectivities for *P. juliae* and *M. alpina* Δ6 desaturases.

| Vector | Gene | FA in medium | % conv GLA* | % conv SDA* | Ratio n-3:n-6** |
| --- | --- | --- | --- | --- | --- |
| pMON67011 | *P. juliae* D6D-2 | LA + ALA | 21.0 | 32.1 | 1.53 |
| pMON67011 | *P. juliae* D6D-2 | LA + ALA | 19.2 | 30.3 | 1.58 |

TABLE 2-continued

Comparison of n-3:n-6 substrate selectivities for *P. juliae* and *M. alpina* Δ6 desaturases.

| Vector | Gene | FA in medium | % conv GLA* | % conv SDA* | Ratio n-3:n-6** |
|---|---|---|---|---|---|
| pMON83950 | *P. juliae* D6D-1 | LA + ALA | 18.7 | 35.4 | 1.89 |
| pMON83950 | *P. juliae* D6D-1 | LA + ALA | 22.2 | 38.4 | 1.73 |
| pMON77205 | *M. alpina* D6D | LA + ALA | 3.6 | 2.8 | 0.78 |
| pMON77205 | *M. alpina* D6D | LA + ALA | 12.8 | 10.5 | 0.82 |

*The percentage conversion to GLA was calculated by dividing the value for GLA (Table 1) by the sum of the values for LA and GLA (Table 1). The same calculation was made for SDA using the sum of ALA and SDA (Table 1).
**The n-3:n-6 ratio was calculated by dividing the % conv. SDA by % conv. GLA.

Example 3

Plant Transformation and Expression of Primula juliae Δ6-desaturase

Figure 4:
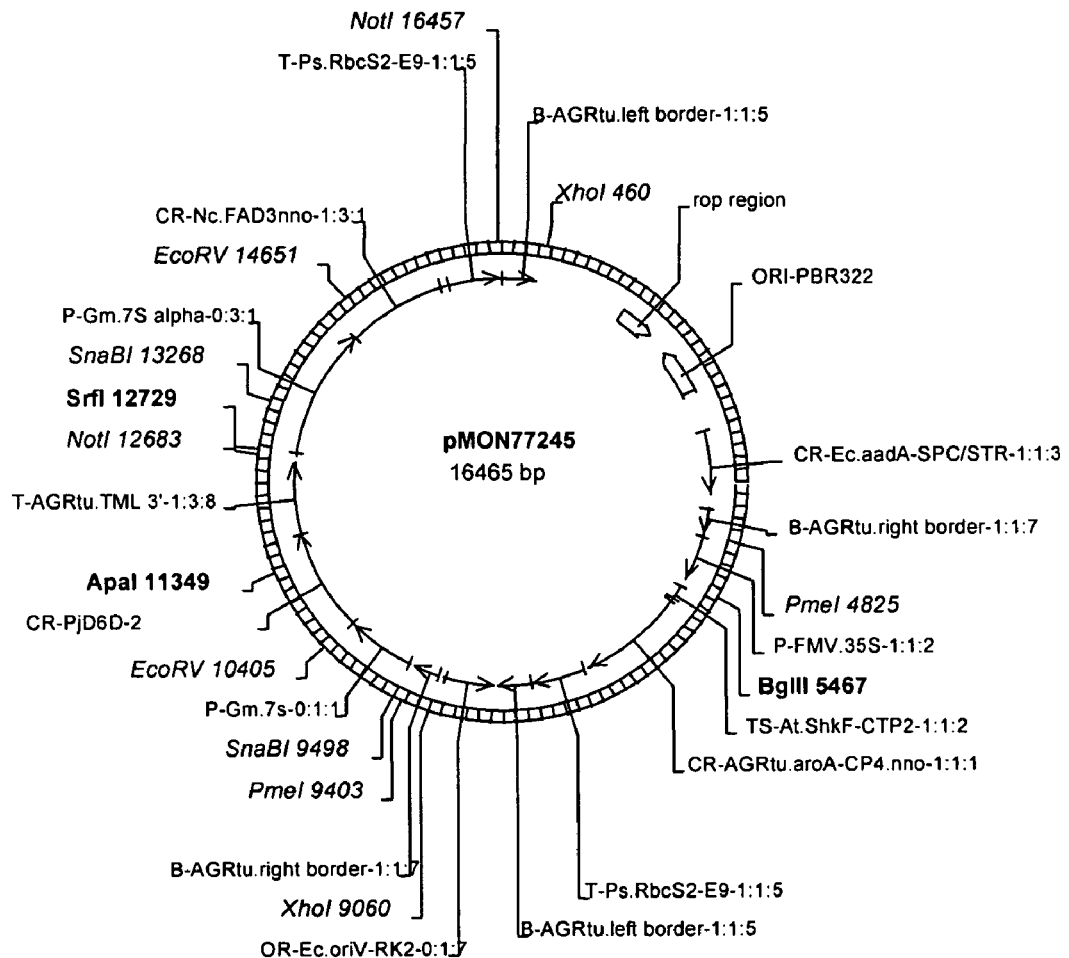
FIG. 4 shows map of vector pMON77245.
Figure 5:
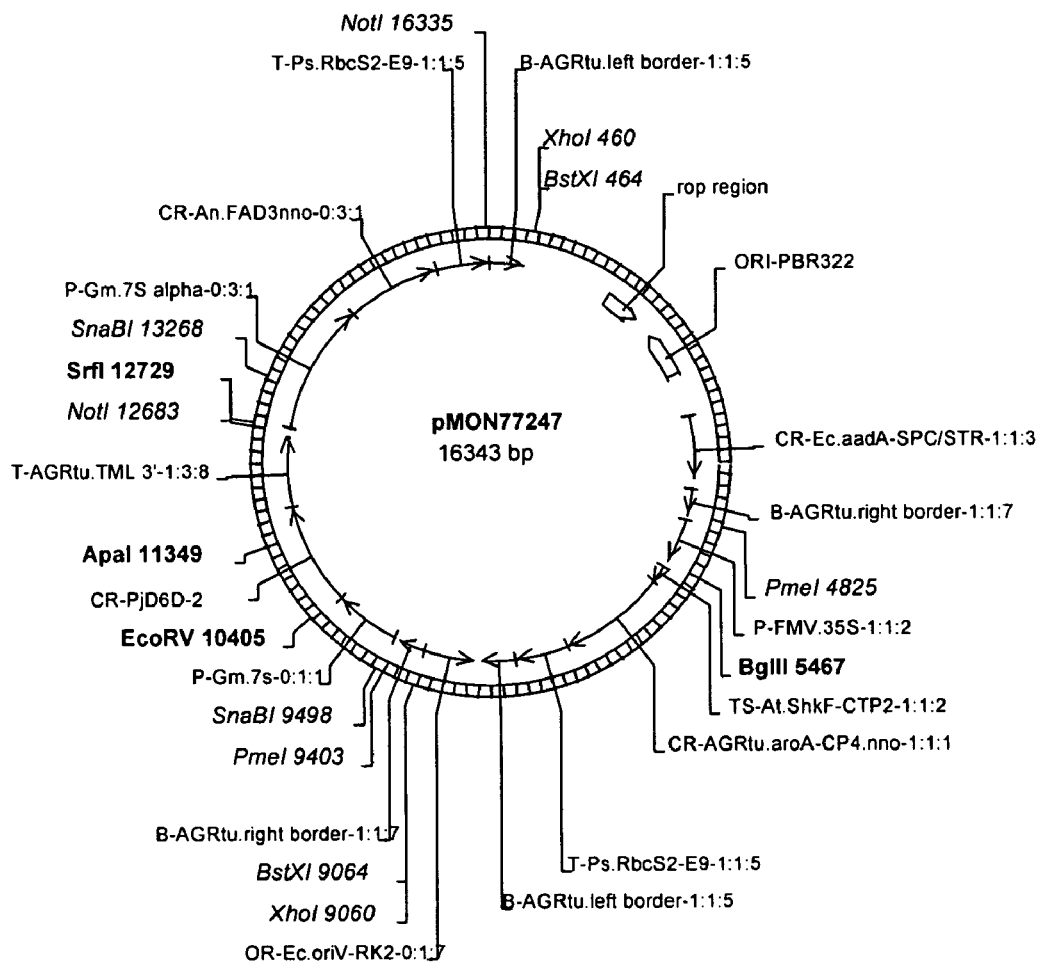
FIG. 5 shows map of vector pMON77247.
Figure 6:
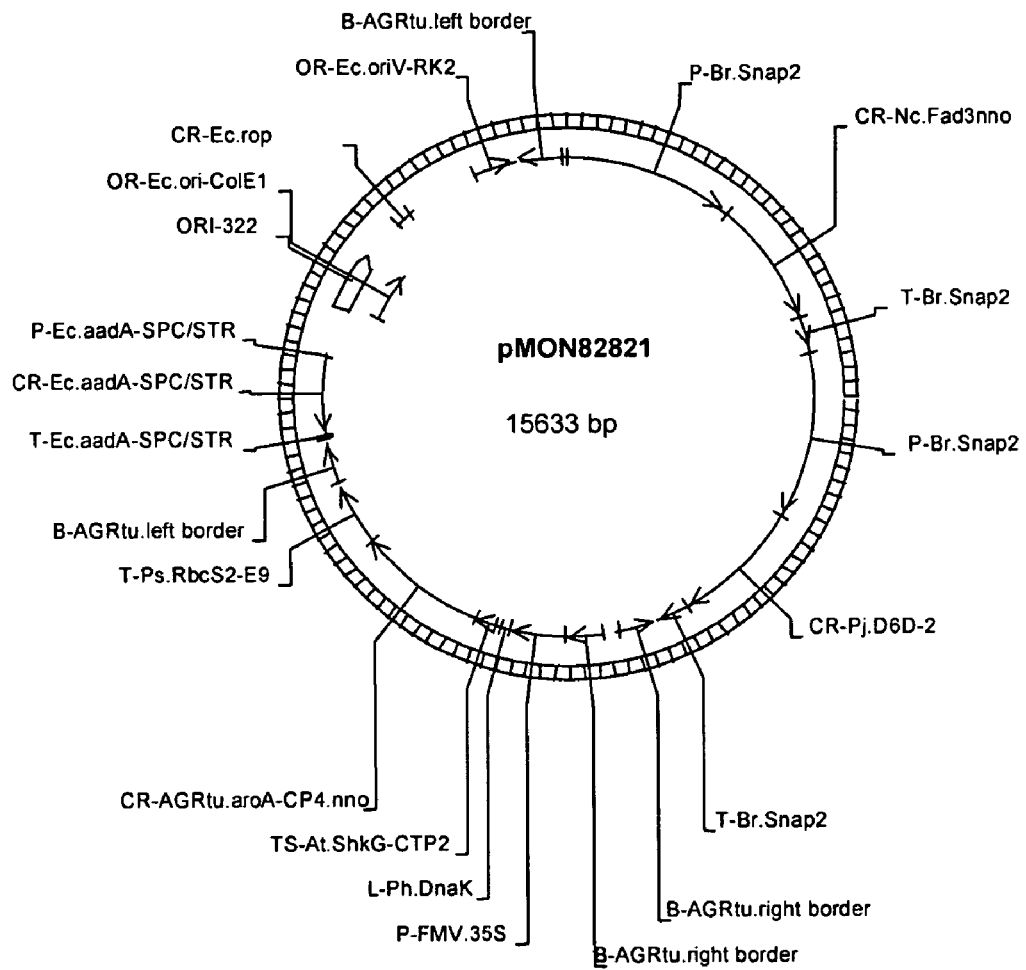
FIG. 6 shows map of vector pMON82821.

The activity of the *P. juliae* Δ6-desaturase was evaluated in soybean by combining it with a Δ15-desaturase from either *Neurospora crassa* (NcD15D), pMON77245 (FIG. 4), or *Aspergillus nidulans* (AnD15D), pMON77247 (FIG. 5). The vector pMON77245 was constructed in three steps. First *P. juliae* Δ6-desaturase (PjD6D-2) was placed behind the seed-specific 7S alpha' promoter by digesting pMON67011 with Sse8387 I, followed by removal of the 3' overhangs, and Sal I, and then ligating the resulting fragment into the EcoRI and filled-in XhoI sites of the expression vector pMON68527, generating the vector pMON77243. Second, the PjD6D-2 expression cassette was removed from pMON77243 by digesting with NotI, followed by a fill-in reaction, and then the resulting fragment was ligated into the EcoRV site of the 2T binary vector pMON77244. Finally, a codon-optimized NcD15D (SEQ ID NO:17) under the control of a 7S alpha seed-specific promoter was combined with the PjD6D-2 by digesting pMON77227 with NotI and then ligating the resulting NcD15D expression cassette fragment into NotI digested pMON77344 to give pMON77245 (FIG. 4). The vector pMON77247 (FIG. 5) was constructed by digesting vector pMON77242 with Not I and ligating the resulting expression cassette fragment comprising a codon-optimized AnD15D (SEQ ID NO:18) linked to the 7S alpha promoter into the NotI site of pMON77244. The vectors pMON77245 and pMON77247 were transformed into soybean using the method of Martinell et al. (U.S. Pat. No. 6,384,301, the disclosure of which is incorporated herein by reference in the entirety).

Expression of the PjD6D-2 coding sequence was measured by determining the fatty acid composition of immature (approximately 30 days after flowering) R1 transgenic soybean seeds, including both homozygotes and heterozygotes, by gas chromatography of lipid methyl ester derivatives (PCT US03/16144, filed May 21, 2003, the entire disclosure of which is specifically incorporated herein by reference). The levels of PA (palmitic acid, 16:0), SA (stearic acid, 18:0), OA, LA, GLA, ALA, and SDA are expressed as a percentage of the total weight of measured fatty acids and are shown in Tables 3 and 4 below. The non-transgenic control line was A3525. Whenever possible, five individual seeds were analyzed from each event.

Individual seed from a majority of the pMON77245 transgenic events were found to accumulate measurable amounts of SDA. In all cases, the levels of SDA were greater than those of GLA, with an average SDA:GLA ratio for each event ranging from 2:1 to a high of 8:1. The highest single seed value was observed from event GM_A38083, which contained 32.0% SDA and 2.6% GLA, with a SDA:GLA ratio of 12:1. Of the 12 events shown below, 9 had SDA values >10% in at least one seed out of five. As SDA values increased, the levels of PA, SA and OA did not vary significantly from control levels; however, there is a strong negative correlation for LA. In seeds that accumulated SDA, the levels of GLA remains low, between 2.3 to 5.5%. The ALA levels increased along the SDA levels.

TABLE 3

Relative Area Percent Results (Approx. wt percent) from single pMON77245-transformed R1 seeds

| pMON77245 Pedigree | Fatty Acid (percent wt) | | | | | | |
|---|---|---|---|---|---|---|---|
| | PA | SA | OA | LA | GLA | ALA | SDA |
| A3525 | 11.47 | 5.21 | 16.5 | 56.75 | 0 | 9.15 | 0 |
| A3525 | 11.66 | 4.53 | 18.54 | 54.9 | 0 | 9.51 | 0 |
| A3525 | 11.8 | 5.42 | 16.66 | 56.04 | 0 | 9.14 | 0 |
| A3525 | 11.41 | 4.91 | 17.64 | 56 | 0 | 9.08 | 0 |
| A3525 | 11.56 | 4.36 | 17.86 | 56.55 | 0 | 8.77 | 0 |
| GM_A38005 | 12.57 | 4.19 | 18.45 | 53.99 | 0 | 10.8 | 0 |
| GM_A38005 | 13.73 | 4.77 | 19.32 | 52.42 | 0 | 9.76 | 0 |
| GM_A38005 | 14.81 | 4.74 | 19.09 | 36.84 | 5.23 | 10.3 | 8.98 |
| GM_A38005 | 13.4 | 4.71 | 18.34 | 53.26 | 0 | 10.29 | 0 |
| GM_A38005 | 13.21 | 4.38 | 19.97 | 52.19 | 0 | 10.25 | 0 |
| GM_A38005 | 13.08 | 4.78 | 17.99 | 53.56 | 0 | 10.59 | 0 |
| GM_A38013 | 12.91 | 4.45 | 19.72 | 40.8 | 4.57 | 9.56 | 7.99 |
| GM_A38013 | 12.45 | 4.38 | 18.9 | 55.04 | 0 | 9.23 | 0 |
| GM_A38013 | 13.04 | 4.68 | 17.38 | 40.36 | 4.66 | 10.27 | 9.61 |
| GM_A38013 | 13.26 | 4.34 | 17.14 | 40.03 | 4.6 | 10.17 | 10.46 |
| GM_A38013 | 11.67 | 4.26 | 22.5 | 44.26 | 3.3 | 8.95 | 5.05 |
| GM_A38021 | 12.95 | 4.33 | 19.39 | 53.48 | 0 | 9.85 | 0 |
| GM_A38021 | 13.07 | 4.87 | 18.12 | 54.1 | 0 | 9.84 | 0 |
| GM_A38021 | 13.14 | 4.27 | 22.76 | 34.62 | 2.3 | 13.7 | 9.2 |
| GM_A38021 | 12.98 | 4.08 | 21.58 | 39.6 | 1.6 | 13.7 | 6.45 |
| GM_A38021 | 13.21 | 4.34 | 17.24 | 29.03 | 1.78 | 19.07 | 15.31 |
| GM_A38043 | 13.1 | 4.26 | 19.58 | 52.44 | 0 | 10.62 | 0 |
| GM_A38043 | 13.09 | 4.3 | 20.01 | 52.83 | 0 | 9.77 | 0 |
| GM_A38043 | 14.01 | 4.35 | 22.05 | 29.98 | 4.39 | 12.18 | 13.05 |
| GM_A38043 | 13.32 | 4.26 | 19.41 | 51.85 | 0 | 11.16 | 0 |
| GM_A38043 | 12.8 | 4.34 | 19.81 | 53 | 0 | 10.05 | 0 |
| GM_A38048 | 13.44 | 5.5 | 18.01 | 44.46 | 2.28 | 10.7 | 5.61 |
| GM_A38048 | 13.43 | 4.8 | 18.57 | 44.25 | 2.34 | 10.93 | 5.68 |
| GM_A38048 | 13.14 | 4.47 | 18.88 | 44.97 | 2.33 | 10.78 | 5.44 |
| GM_A38048 | 12.98 | 4.89 | 17.79 | 44.92 | 2.43 | 11.23 | 5.76 |
| GM_A38048 | 13.3 | 4.56 | 17.95 | 35.88 | 3.41 | 13.15 | 11.75 |
| GM_A38060 | 12.73 | 4.94 | 17.37 | 43.16 | 4.01 | 10.4 | 7.39 |
| GM_A38060 | 12.85 | 5.19 | 15.27 | 35.1 | 5.32 | 11.88 | 14.39 |
| GM_A38060 | 12.73 | 4.99 | 16.41 | 43.44 | 3.95 | 10.25 | 8.23 |
| GM_A38060 | 13.06 | 5.34 | 16.06 | 42.75 | 4.04 | 10.32 | 8.43 |
| GM_A38060 | 12.85 | 5.25 | 16.45 | 42.68 | 4.01 | 10.39 | 8.36 |
| GM_A38064 | 13.32 | 5 | 18.8 | 42 | 3.86 | 10.16 | 6.87 |
| GM_A38064 | 13.07 | 4.72 | 18.97 | 42.1 | 3.59 | 9.95 | 7.6 |
| GM_A38064 | 13.45 | 4.84 | 19.7 | 41.67 | 3.8 | 9.92 | 6.62 |
| GM_A38064 | 12.66 | 4.61 | 19.09 | 43.21 | 3.52 | 9.85 | 7.05 |
| GM_A38064 | 13.03 | 4.73 | 19.58 | 36.38 | 4.94 | 11.28 | 10.06 |
| GM_A38069 | 12.9 | 4.71 | 21.24 | 41.12 | 2.64 | 11.43 | 5.97 |
| GM_A38069 | 12.74 | 4.76 | 20.35 | 51.21 | 0 | 10.94 | 0 |
| GM_A38069 | 12.93 | 4.77 | 20.5 | 51.27 | 0 | 10.53 | 0 |
| GM_A38069 | 13.18 | 4.69 | 18.85 | 38.76 | 3.3 | 12.34 | 8.87 |
| GM_A38069 | 13.08 | 4.79 | 19.16 | 52.08 | 0 | 10.89 | 0 |
| GM_A38083 | 13.33 | 5.28 | 21.73 | 27.31 | 2.48 | 15.28 | 13.35 |
| GM_A38083 | 12.8 | 4.96 | 16.85 | 11.52 | 2.64 | 18.11 | 32.02 |
| GM_A38083 | 12.32 | 5.07 | 22.23 | 13.59 | 2.52 | 17.46 | 25.56 |
| GM_A38083 | 13.22 | 4.26 | 20.83 | 15.89 | 3.81 | 14.69 | 26.12 |
| GM_A38083 | 13.74 | 4.61 | 17.03 | 20.93 | 4.84 | 13.82 | 23.91 |
| GM_A38084 | 12.9 | 4.04 | 22.66 | 41.63 | 3.37 | 9.07 | 5.28 |
| GM_A38084 | 13.38 | 3.94 | 28.07 | 25.81 | 4.9 | 11.37 | 11.42 |
| GM_A38084 | 13.92 | 3.75 | 31.36 | 32.26 | 2.89 | 9.23 | 5.51 |
| GM_A38084 | 14.42 | 4.12 | 27.17 | 33.26 | 3.28 | 11.57 | 5.77 |
| GM_A38084 | 12.74 | 3.95 | 22.59 | 40.82 | 3.3 | 9.68 | 5.91 |
| GM_A38089 | 13.05 | 4.48 | 22.37 | 42.63 | 2.55 | 9.3 | 4.59 |

TABLE 3-continued

Relative Area Percent Results (Approx. wt percent) from single pMON77245-transformed R1 seeds

| pMON77245 | Fatty Acid (percent wt) | | | | | | |
|---|---|---|---|---|---|---|---|
| Pedigree | PA | SA | OA | LA | GLA | ALA | SDA |
| GM_A38089 | 13.15 | 4.63 | 18.82 | 53.48 | 0 | 9.03 | 0 |
| GM_A38089 | 12.67 | 4.41 | 20.59 | 51.87 | 0 | 9.42 | 0.07 |
| GM_A38089 | 12.64 | 4.29 | 20.56 | 52.58 | 0 | 8.96 | 0 |
| GM_A38089 | 12.72 | 4.57 | 21.81 | 50.79 | 0 | 9.16 | 0 |
| GM_A38094 | 12.62 | 4.57 | 18.97 | 52.96 | 0 | 9.9 | 0.11 |
| GM_A38094 | 13.3 | 5.08 | 17.08 | 34.49 | 5.35 | 11.39 | 12.35 |
| GM_A38094 | 13.08 | 4.52 | 18.38 | 38.95 | 5.41 | 9.88 | 8.82 |
| GM_A38094 | 13.41 | 5 | 17.27 | 38.5 | 5.49 | 10.26 | 9.1 |
| GM_A38094 | 12.58 | 4.46 | 20.06 | 40.28 | 4.88 | 9.5 | 7.25 |

Individual seed from the pMON77247 transgenic events accumulated similar amounts of SDA as compared to pMON77245, with the exception of event GM_A38083 that accumulated significantly higher levels of SDA. The levels of PA, SA, OA, and LA were similar to the control levels shown in Table 3. Generally, the levels of SDA were greater than those of GLA with an average SDA:GLA ratio for each event ranging from 1:1 to 1.6:1, which was less than that observed for pMON77245.

TABLE 4

Relative Area Percent Results (Approx. wt percent) from single pMON77247 R1 seeds

| pMON77247 | Fatty Acid (percent wt) | | | | | | |
|---|---|---|---|---|---|---|---|
| Pedigree | PA | SA | OA | LA | GLA | ALA | SDA |
| GM_A38909 | 12.18 | 4.19 | 20.66 | 44.94 | 3.52 | 8.65 | 4.87 |
| GM_A38909 | 12.25 | 3.84 | 22.37 | 44.89 | 2.95 | 8.22 | 4.46 |
| GM_A38909 | 12.06 | 4.67 | 22.95 | 43.37 | 3.31 | 8.32 | 4.86 |
| GM_A38909 | 12.64 | 4.63 | 17.61 | 45.99 | 3.66 | 9.01 | 5.44 |
| GM_A38909 | 12.28 | 4.2 | 19.42 | 46.1 | 3.1 | 9.01 | 4.82 |
| GM_A38941 | 13.95 | 4.87 | 18.03 | 40.2 | 7.08 | 7.87 | 6.92 |
| GM_A38941 | 13.76 | 4.38 | 19.72 | 33.62 | 8.94 | 8.57 | 9.95 |
| GM_A38941 | 13.15 | 4.91 | 17.89 | 52.06 | 0.75 | 9.52 | 0.8 |
| GM_A38941 | 12.73 | 4.27 | 22.23 | 42.14 | 4.98 | 7.44 | 5.15 |
| GM_A38941 | 12.73 | 4.34 | 19.37 | 52.34 | 0.36 | 9.53 | 0.37 |
| GM_A38946 | 13.02 | 4.68 | 17.4 | 44.66 | 4.54 | 8.83 | 5.89 |
| GM_A38946 | 13.17 | 4.42 | 17.35 | 43.71 | 5.01 | 8.91 | 6.49 |
| GM_A38946 | 13.63 | 4.24 | 18.96 | 38.16 | 6.36 | 8.89 | 8.75 |
| GM_A38946 | 13.32 | 4.6 | 17.76 | 43.37 | 4.8 | 8.94 | 6.2 |
| GM_A38946 | 13.32 | 4.5 | 18.07 | 43.24 | 4.71 | 8.95 | 6.23 |
| GM_A38977 | 13.43 | 5.18 | 21.3 | 40.54 | 4.43 | 8.51 | 5.62 |
| GM_A38977 | 13.6 | 4.92 | 21.44 | 40.95 | 4.26 | 8.41 | 5.42 |
| GM_A38977 | 13.17 | 4.23 | 21.61 | 38.02 | 5.45 | 8.38 | 8.07 |
| GM_A38977 | 13.06 | 4.97 | 21.93 | 37.82 | 5.75 | 8.63 | 6.86 |
| GM_A38977 | 13.33 | 4.5 | 22.96 | 37.43 | 5.54 | 8.42 | 6.76 |
| GM_A39047 | 13.22 | 4.21 | 20.95 | 31.88 | 7.8 | 9.01 | 11.72 |
| GM_A39047 | 13.34 | 4.47 | 19.14 | 31.1 | 7.54 | 9.9 | 13.35 |
| GM_A39047 | 13.79 | 4.32 | 18.82 | 32.97 | 8.26 | 9.07 | 11.68 |
| GM_A39047 | 13.16 | 4.38 | 19.34 | 29.61 | 7.94 | 9.97 | 14.44 |
| GM_A39047 | 12.65 | 4.25 | 17.48 | 50.71 | 1.49 | 9.92 | 2.45 |

Example 4

Figure 7:
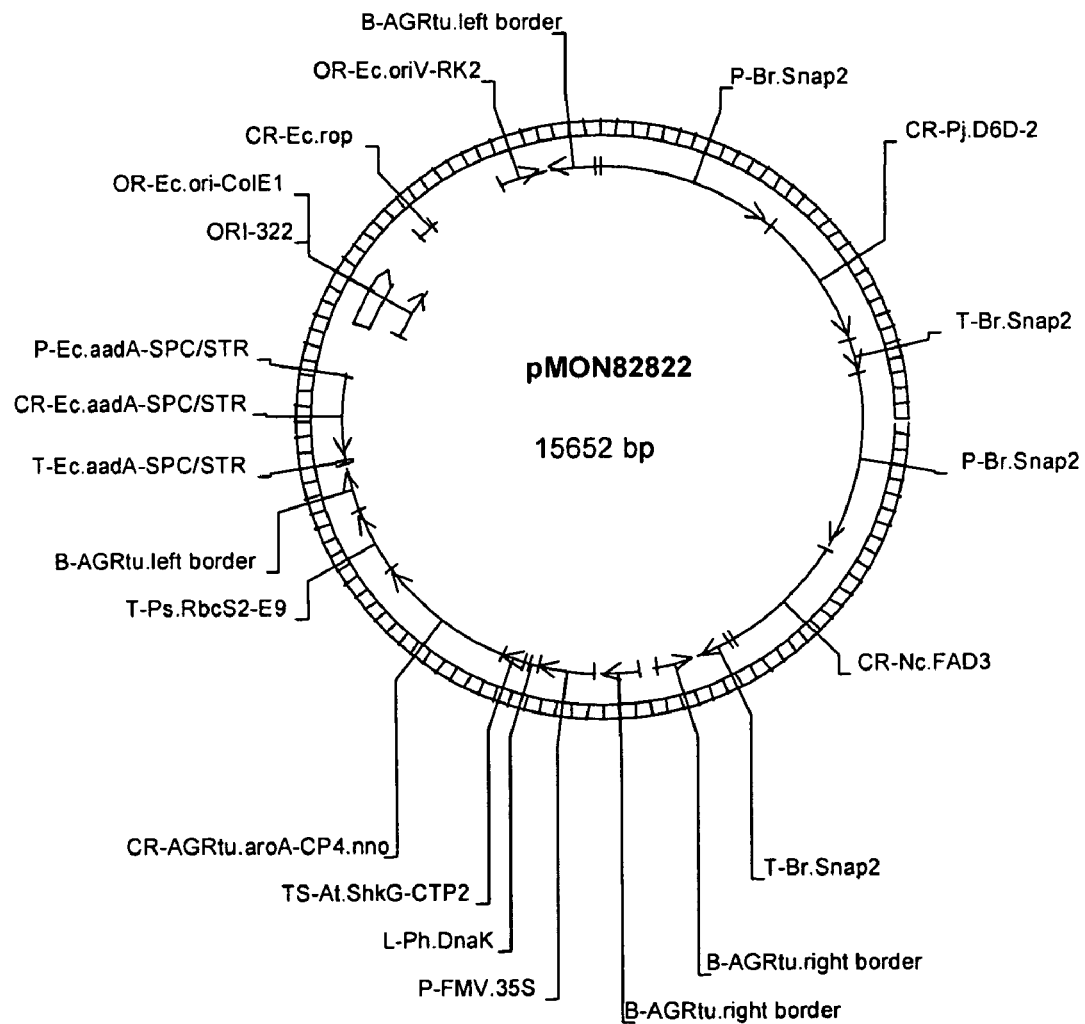
FIG. 7 shows map of vector pMON82822.

Activity of the Primula juliae Δ6-desaturase in Combination with the Neurospora crassa Δ15-desaturase in Canola The activity of the *Primula juliae* Δ6-desaturase in combination with *Neurospora crassa* Δ15-desaturase was evaluated by transforming canola with the MON82822 (FIG. 7). pMON82822 contained a native NcD15D (SEQ ID NO:19) as well as PjD6D-2, both inserted into a seed-specific expression cassette under the control of the napin promoter (PCT US03/16144, the disclosure of which is specifically incorporated herein by reference).

The pMON82822 vector was constructed by first digesting pMON77214 (PCT US03/16144) with PmeI and BamHI (filled-in) and ligating the resulting native NcD15D napin cassette into the EcoRV site of the 2T binary vector pMON71801 to generate pMON82820. Next, pMON82819 was digested with NotI, the ends were filled in and the resulting PjD6D-2 napin expression cassette was ligated into the filled-in AscI site of pMON82820 to generate pMON82822.

A second vector, pMON82821, was also constructed containing the codon-optimized NcD15D (SEQ ID NO:17) and PjD6D-2 pMON82821 by first digesting pMON67011 with SalI and Sse8387I and ligating the resulting PjD6D-2 fragment into the SalI and XhoI (filled-in) sites of the napin expression cassette in pMON82800 giving pMON82819. The napin cassette containing a codon-optimized NcD15D was constructed by digesting pMON67024 with PmeI and BamHI (filled-in) and ligating the resulting fragment into an EcoRV-digested 2T binary vector, pMON71801, giving pMON82801. Finally, pMON82819 was digested with NotI, filled-in and the resulting PjD6D-2 napin expression cassette was ligated into the filled in NotI site of pMON82801 giving pMON82821.

pMON82822 was transformed into canola (*Brassica napus*) using a modification of the protocol described by Radke et al., (*Plant Cell Reports* 11:499-505, 1992). Briefly canola seed of the cultivar 'Ebony' (Monsanto Canada, Inc., Winnipeg, Canada) were disinfected and germinated in vitro as described in Radke et al., 1992. Precocultivation with tobacco feeder plates, explant preparation and inoculation of explants with *Agrobacterium tumefaciens* strain ABI (Koncz and Schell, *Mol Gen Genet.* 204:383-396 (1986)) containing the desired vector were as described with the *Agrobacterium* being maintained in LB media (solid or liquid) containing 75 mg/l spectinomycin, 25 mg/l chloramphenicol and 50 mg/l kanamycin. For plant transformation including callus induction, shoot regeneration, maturation and rooting, glyphosate selection was used rather than the kanamycin selection as described in Radke et al., 1992. Specifically, the B5-1 callus induction medium was supplemented with 500 mg/l carbenicillin and 50 mg/l Timentin (Duchefa Biochemie BV) to inhibit the *Agrobacterium* growth and kanamycin was omitted from the media. B5BZ shoot regeneration medium contained, in addition, 500 mg/l carbenicillin, 50 mg/l Timentin and 45 mg/l glyphosate with explants being transferred to fresh medium every two weeks.

Glyphosate selected shoots were transferred to hormone-free B5-0 shoot maturation medium containing 300 mg/l carbenicillin and 45 mg/l glyphosate for two weeks and finally shoots were transferred to B5 root induction medium containing 45 mg/l glyphosate. Rooted green plantlets were transplanted to potting soil and acclimated to green house conditions. Plants were maintained in a greenhouse under standard conditions. The fatty acid composition of mature seed was determined by GC analysis of methyl ester derived lipids as done above for soybean transformants. The GC analysis of canola seed from plants transformed with pMON82822 yielded 199 events with SDA levels ranging from 0.12 to 4.49% (weight %, 100 seed pool).

Example 5

Construction and Transformation of PjD6D Expression Vectors for Soy, Corn and Canola The expression of the PjD6D sequences alone is evaluated in planta for canola, corn and soybean under the expression a seed-specific promoter. A soybean expression vector is constructed by digesting pMON77243 with Not I, and ligating the resulting fragment containing PjD6D-2 into the Not I site of the binary vector pMON17227. A canola expression vector is constructed by digesting pMON83950 with SalI and Sse8387I (made blunt) and ligating the resulting fragment, which contains the coding region of PjD6D-1 into the SalI and XhoI (filled-in) sites of the seed-specific napin expression cassette vector pMON82800. The resulting plasmid is then digested with Not I followed by ligating the resulting napin-PjD6D-1 expression cassette into the Not I site of the binary vector pMON17227. A corn expression vector is constructed by digesting pMON83950 with Sal I (filled-in) and Sse83872I (made blunt) and ligating the resulting PjD6D-1 fragment into the SfiI (made blunt) site of the globulin expression cassette in pMON71084. The resulting vector is then digested with PmeI and HindIII and the expression cassette is then ligated into the HpaI and HindIII sites of the binary vector pMON30167.

The activity of the *P. juliae* Δ6-desaturase in corn is evaluated in combination with a *Neurospora crassa* Δ15-desaturase codon-optimized for corn (NcD15Dnno) (SEQ ID NO:20). The vector pMON67011 is digested with SalI and Sse83871 (made blunt) and the resulting PjD6D-2 fragment is ligated into the SfiI (fill-in) site of the globulin expression cassette in pMON71084 to give pMON82823. Next, pMON82806 (PCT US03/16144) is digested with PmeI and HindIII and the resulting globulin NcD15Dnno cassette is ligated into the NotI (fill-in) and HindIII sites of the 1T binary vector pMON30167 to give pMON82824. Finally the globulin PjD6D-2 cassette is combined with globulin NcD15Dnno by digesting pMON82823 with PmeI and HindIII and ligating the resulting fragment into the SmaI and HindIII sites of pMON82824 giving pMON82825. The resulting vector is introduced into maize via *Agrobacterium tumefaciens*-mediated transformation as known to one of skill in the art, e.g., U.S. Pat. No. 6,603,061.

Example 6

Cloning of Primula waltonii and Primula alpicola Δ6 Desaturase Sequences

Cloning of the *Primula waltonii* Δ6 desaturase (PwD6D) and *P. alpicola* Δ6 desaturase (PaD6D) genes was achieved by PCR amplification of a partial internal genomic DNA region using degenerate oligonucleotides, followed by bi-directional genomic walking. Total genomic DNA was isolated from *P. waltonii* and *P. alpicola* (Collector's Nursery) using the DNeasy Plant Mini Kit (Qiagen), following the manufacturer's procedure. Two fragments were isolated from the *P. alpicola* genomic DNA using the degenerate oligonucleotides BO-1 For and BO-2 Rev as described by Garcia-Maroto et al. 2002:

```
BO-1 For:
5'-ATMAGYATYGGTTGGTGGAARTGG-3'    (SEQ ID NO: 6)

BO-2 Rev:
5'-AATCCACCRTGRAACCARTCCAT-3'    (SEQ ID NO: 7)
```

The first *P. alpicola* fragment was 550 bp in length and corresponded to positions 553 to 1103 of SEQ ID NO:21. This fragment was cloned into pCR®4-TOPO® (Invitrogen) to yield the vector pMON83977 (no intron). The second *P. alpicola* fragment was 550 bp in length and corresponded to positions 763 to 1313 of SEQ ID NO:23. This fragment was cloned into pCR®4-TOPO® (Invitrogen) to yield the vector pMON83975 (contains intron). One fragment was obtained from *P. waltonii* that was 550 bp in length and corresponded to positions 763 to 1313 of SEQ ID NO:25. This fragment was cloned into pCR®4-TOPO® (Invitrogen) to yield the vector pMON83976. The polypeptide sequences encoded by SEQ ID NOs:21, 23 and 25 are given in SEQ ID NOs:22, 24 and 26, respectively.

To determine the genomic flanking sequences of the pMON83975, pMON83976, and pMON83977 inserts, a Universal Genome Walker Kit™ (BD Biosciences) was utilized, following the manufacture's procedure. Four genomic libraries for each *Primula* species were generated by digesting the DNA with four restriction enzymes: EcoRV, PvuII, StuI, and DraI. After a purification step, the digestions were ligated to an adapter provided in the kit. The procedure then involved two PCR reactions, each with a gene-specific primer and an adapter-primer. The secondary PCR reaction used a dilution of the primary PCR reaction products as a template.

A. pMON83975 (PaD6D-2)

For the 5' direction, primers PD6D R7 and PD6D R1 were used for the primary and secondary PCR reactions, respectively. For the 3' direction, primers PD6D F7 and PD6D F1 were used for the primary and secondary PCR reactions, respectively. The primer sequences are given below:

```
PD6D R7:
5'-CACACATGACCGGATAAAACGTCCAGT-3'    (SEQ ID NO: 27)

PD6D R1:
5'-AGGGATATACTGGAGGTCGGGGTCGTA-3'    (SEQ ID NO: 28)

PD6D F7:
5'-GAGCTATTCCGTTACGGGGATACAACA-3'    (SEQ ID NO: 29)

PD6D F1:
5'-TGCAGGGACACTTAACATATCGTGCCC-3'    (SEQ ID NO: 30)
```

Genome walking in the 5' direction yielded a 751 bp fragment from the EcoRV library. This product was cloned into pCR®4-TOPO® (Invitrogen) giving pMON83978, and the insert was sequenced. The resulting sequence did not contain a start codon of the putative delta 6 desaturase gene and thus another set of PCR reactions was performed using gene specific primers designed to walk in the 5' direction from the pMON83978 insert. The primers used for the second genome walking set in the 5' direction were PD6D R17 and PD6D R16 for the primary and secondary PCR reactions, respectively. The sequences are given below:

```
PD6D R17:
5'-GTGAAAGTTGTTGAGGAGGGATCGGTA-3'    (SEQ ID NO: 31)

PD6D R16:
5'-GTGGAAGGAGGATGGTAAGCGAGGAAA-3'    (SEQ ID NO: 32)
```

A product of 473 bp in length from the PvuII library was cloned into pCR®4-TOPO® giving pMON83980 and the insert was sequenced. This insert contained a start codon corresponding to position 1 of SEQ ID NO:23. Genome walking in the 3' direction resulted in a 942 bp fragment from the DraI library. This product was cloned into pCR®4-TOPO®, giving pMON83979. The insert was sequenced and found to contain 294 bp of the coding region for the putative delta 6 desaturase gene, followed by a stop codon at position 1549 with respect to SEQ ID NO:23.

The inserts of pMON83975, pMON83978, pMON83980 and pMON83979 were aligned to form a composite sequence of a putative Δ6 desaturase gene for *P. alpicola* giving PaD6D-2, SEQ ID NO:23. Two primers were designed to PCR amplify the complete open reading frame from *P. alpicola* genomic DNA. The primer sequences are given below:

```
Pa D6D F1:  5'- GTCGACATGGCTAACAAATCTCAAACAGGTTAC-3'   (SEQ ID NO: 33)

Pa D6D R1:  5'- CCTGCAGGTCACCCGAGAGTTTTAACAGCCTCC-3"  (SEQ ID NO: 34)
```

The PCR amplified fragment (SEQ ID NO:23) was then ligated into the yeast expression vector pYES2.1-TOPO giving the vector pMON83968.

B. pMON83976 (PwD6D)

A putative Δ6 desaturase was PCR amplified from *P. waltonii* genomic DNA using the primers Pa D6D F1 (SEQ ID NO:33) and Pa D6D R1 (SEQ ID NO:34) shown above. The PCR amplified fragment (SEQ ID NO:25) was then ligated into the yeast expression vector pYES2.1-TOPO giving the vector pMON83967.

C. pMON83977 (PaD6D-1)

For the 5' direction, primers PD6D R9 and PD6D R4 were used for the primary and secondary PCR reactions, respectively. For the 3' direction, primers PD6D F9 and PD6D F4 were used for the primary and secondary PCR reactions, respectively. The primer sequences are given below:

```
PD6D R9:
5'-CACACATTACCGGATAAAACGTCCAGT-3'    (SEQ ID NO: 35)

PD6D R4:
5'-AGGAATATACTGGAGGTCTGGGTCGTA-3'    (SEQ ID NO: 36)

PD6D F9:
5'-ATTTTTCTTCGGACGTATACATGGGCC-3'    (SEQ ID NO: 37)

PD6D F4:
5'-TTCGGGGACACTGAACATATCGTGCCC-3'    (SEQ ID NO: 38)
```

Genome walking in the 5' direction yielded a 979 bp fragment from the StuI library. This product was cloned into pCR®4-TOPO® (Invitrogen) giving pMON83981, and the insert was sequenced. The resulting sequence contained the start codon of the putative delta 6 desaturase at position 1 with respect to SEQ ID NO:21. Genome walking in the 3' direction resulted in a 1028 bp fragment from the DraI library. This product was cloned into pCR®4-TOPO® (Invitrogen), giving pMON83982. The insert was sequenced and found to contain 295 by of the coding region for the putative delta 6 desaturase gene, followed by a stop codon at position 1339 with respect to SEQ ID NO:21.

The inserts of pMON83977, pMON83981 and pMON83982 were aligned to form a composite sequence of a second putative Δ6 desaturase gene for *P. alpicola* giving PaD6D-1, SEQ ID NO:21. Two primers were designed to PCR amplify the complete open reading frame from *P. alpicola* genomic DNA. The primer sequences are given below.

```
Pf D6D-F2:  5'-GTCGACATGGCCAACACTAGTTACATTTCCAGCT-3'   (SEQ ID NO: 39)

Pf D6D-R2:  5'-GATATCACCCCAGAGTGTTAACAGCTTCCCAG-3'     (SEQ ID NO: 40)
```

The PCR amplified fragment was then ligated into the yeast expression vector pYES2.1-TOPO giving the vector pMON67026 (SEQ ID NO 21).

Alignment of PaD6D-2 and PwD6D (also abbreviated PRIwaD6D) with other characterized plant Δ6 desaturase genes revealed that these two genes contained a single intron corresponding to positions 476 to 676 in SEQ ID NO:23 and positions 476 to 651 in SEQ ID NO:25. This has been observed in Δ6 desaturases from *Primula* and *Echium* species (Sayanova et al., 2003, Garcia-Maroto et al., 2002).

The three Δ6 desaturase clones encode potential polypeptides of 446 amino acids for PaD6D-1 (SEQ ID NO:22), 449 amino acids for PaD6D-2 (SEQ ID NO: 24) and 449 amino acids for PwD6D (SEQ ID NO: 26). These sequences have high similarity to other plant Δ6 desaturases (FIG. 1), including an N-terminal cytochrome $b_5$ domain, which is found in all front-end desaturases (Napier et al., 2003). Within the cytochrome $b_5$ domain is found the eight invariant residues characteristic of the cytochrome $b_5$ superfamily and the H-P-G-G heme-binding motif, which has been shown to be essential for enzymatic activity (Napier et al., 1997, Sayanova et al, 1999, Sperling and Heinz 2001). Within the desaturase domain of the PaD6D-1, PaD6D-2, and PwD6D desaturases are three conserved histidine boxes that are characteristic of all membrane-bound desaturases (Shanklin et al., 1994). A distinguishing feature found in all front-end desaturases is that the third histidine box contains a glutamine residue in the first position (Q-x-x-H-H) instead of a histidine (Napier et al., 1997, Napier et al., 2003, Sperling and Heinz 2001). The deduced amino acid sequence of the PaD6D-1 had approximately 80% identity to PaD6D-2 and approximately 80% identity to PwD6D. However, the two intron containing genes, PaD6D-2 and PwD6D, are more similar to each other with approximately 97% identity, than the two *P. alpicola* genes, PaD6D-1 and PaD6D are to each other.

Example 7

Cloning Additional Primula Δ6 Desaturase Sequences

Genomic DNA was isolated from *P. farinosa* and *P. florindae* using a Sarkosyl/CTAB lysis system. Five grams of tissue from each species was ground in a mortar and pestle with liquid nitrogen until ground into a fine powder. The powdered tissue was then resuspended in lysis buffer (140 mM sorbitol, 220 mM Tris-HCl, pH 8.0, 22 mM ethylenediaminetetraacetic acid (EDTA), 800 mM sodium chloride (NaCl), 1% N-laurylsarcosine and 0.8% hexadecyltrimethyl ammonium bromide (CTAB)) and incubated for 1 hour at 65° C. with gentle inversion every 10 minutes. After incubation, 10 ml of chloroform was added to the lysis suspension and incubated at room temperature with gentle rocking for 20 minutes. The lysis suspension was centrifuged for 10 minutes at 12,000×g. The aqueous layer was transferred to a clean tube and the nucleic acid precipitated with 0.6% isopropanol. The nucleic acid pellet was resuspended in 4 ml of a solution containing 10 mM Tris-HCl, pH 8.0, 1 mM EDTA, 1 M NaCl and 20 mg Proteinase K. The resuspended nucleic acid was then incubated for 2 hours at 63° C. The Proteinase K was then heat inactivated by incubation at 75° C. for 20 minutes. RNase (2.5 µg) was added to the solution and incubated at 37° C. for 1 hour. The solution was extracted with an equal volume of phenol:chloroform:isoamylalcohol (25:24:1) 2 times. The purified genomic DNA was then ethanol precipitated.

Approximately, 3 μg of genomic DNA was digested in separate reactions with the restriction endonucleases, EcoRI, HindIII, KpnI, SalI and XhoI. After digestion, each reaction was purified using a QIAquick® PCR Purification Kit (Qiagen, Valencia, Calif.), following the manufacturer's protocol. The digested genomic DNA was eluted from the purification columns using 100 μl of elution buffer supplied in the kit. Ligation favoring intramolecular interactions was performed in a 200 μl volume using 20 μl of the eluted digested genomic DNA in a PEG-free ligation reaction with 800 units of ligase (M0202L) (New England Biolabs, Beverly Mass.) overnight at 16° C., followed by heat inactivation at 75° C. for 10 minutes. After ligation, the reaction was again purified using a QIAquick® PCR Purification Kit. Inverse PCR was performed using 6-20 ng of purified ligated DNA and from 10-20 pg of primer and the Expand Long Template PCR System (Roche Applied Science, Indianapolis, Ind.). Primers are shown in Table 5 and were designed using a combination of available sequence data and data covering the desaturase domain. Thermal cycle conditions consisted of an initial incubation at 94° C. for 2 minutes; 10 cycles of 94° C. for 20 seconds, 52° C. for 30 seconds and 68° C. for 8 minutes; followed by 25 cycles of 94° C. for 30 seconds, 52° C. for 30 seconds and 68° C. for 8 minutes plus 10 seconds per cycle. After cycling was complete, a further incubation at 68° C. for 7 minutes was performed. Inverse PCR library products visible after agarose electrophoresis were cloned into either pCR®2.1-TOPO or pCR®4Blunt-TOPO (Invitrogen) following the manufacturer's protocol. The following inverse library fragments (with approximate size) were cloned: *P. farinosa*-EcoRI (6 kb) and *P. florindae*-HindIII (3 kb). The DNA sequencing was performed on an Applied Biosystems 3730×1 DNA Analyzer, using Big Dye® Terminator v3.0.

TABLE 5

Primers and fragments used in inverse PCR determination of the 5' and 3' regions of the delta 6 desaturase genes.

| Species | Primer | Sequence | SEQ ID NO: |
|---|---|---|---|
| P. farinosa | Pfl 107F1 | TGGAGGTCTGGGTCGTAATC | 41 |
|  | Pfl 107R1 | CTTCGGACGTATACATGGGC | 42 |

TABLE 5-continued

Primers and fragments used in inverse PCR determination of the 5' and 3' regions of the delta 6 desaturase genes.

| Species | Primer | Sequence | SEQ ID NO: |
|---|---|---|---|
| P. florindae | Pfl 113-1F2 | TCGTAATCCAGGCTATTGCA | 43 |
|  | Pfl 113-1R2 | TTTTCTTCGGACGTCCATGT | 44 |

Putative sequences were aligned with public data to determine the approximate region of the open reading frame (ORF) covered for each gene. Primers to amplify the ORF of each gene were designed based upon the aligned inverse PCR data. Proofreading polymerases were used to amplify the putative delta 6 genes to insure fidelity of the final product. The primers used in the final cloning of the putative delta 6 desaturase genes are shown in Table 6. The products were cloned into either pUC19 or pCR®4Blunt-TOPO (Invitrogen). DNA sequencing was performed on an Applied Biosystems 3730xl DNA Analyzer, using Big Dye® Terminator v3.0. Two putative delta 6 desaturase genes were cloned: *P. farinosa* (PfaD6D) (pMON84809) (SEQ ID NO:45) and *P. florindae* (PflD6D) (pMON84810) (SEQ ID NO:47).

TABLE 6

Primers used to amplify delta 6 desaturase genes.

| Primer | Sequence | SEQ ID NO: |
|---|---|---|
| Pfarinosa754F | GACGATTTTTGAGTGAGAGTTAATTTGAGTCAATAATA | 49 |
| Pfarinosa2447R | CGACATCATAGACAATCATCAAGACACCGT | 50 |
| PflorindaestartF | ATACCCCCTCAAAACACCCCCAAAT | 51 |
| PflorindaestopR | CTCAATATCACCCGAGAGTTTTAACAGCCT | 52 |

Two primers were designed to amplify the complete PfaD6D open reading frame from pMON84809. The resulting fragment was ligated into the yeast expression vector pYES2.1-TOPO giving pMON67065. The two primers are given below.

Pfar F1: 5'- GTCGAGAACA<u>ATG</u>TCCAACACATATCCACCAAATC -3'  (SEQ ID NO: 53)

Pfar R1: 5'- CCTGCAGGTCACCCCAGAGTGTTAACAGCTTC -3'   (SEQ ID NO: 54)

Two primers were designed to amplify the complete PflD6D gene containing two exons and one intron from pMON84810. The resulting fragment was ligated into vector pYES2.1-TOPO giving pMON67067. The two primers are given below.

Pw F1:
5'- GTCGAC<u>ATG</u>GCTAACAAATCTCAAAC -3' (SEQ ID NO: 55)

Pw R2:
5'- CCTGCAGGTCACGCGAGAGT -3'    (SEQ ID NO: 56)

The two Δ6 desaturase clones encode potential polypeptides of 454 amino acids for PfaD6D (SEQ ID NO:46) and 449 amino acids for PflD6D (SEQ ID NO:48). These sequences have high similarity to other plant Δ6 desaturases (FIG. 1), including an N-terminal cytochrome $b_5$ domain, which is found in all front-end desaturases (Napier et al., 2003). Within the cytochrome $b_5$ domain is found the eight invariant residues characteristic of the cytochrome $b_5$ superfamily and the H-P-G-G heme-binding motif, which has been shown to be essential for enzymatic activity (Napier et al., 1997, Sayanova et al, 1999, Sperling and Heinz 2001). Within the desaturase domain of the putative PflD6D and PfaD6D desaturases are three conserved histidine boxes that are characteristic of all membrane-bound desaturases (Shanklin et al., 1994). A distinguishing feature found in all front-end desaturases is that the third histidine box contains a glutamine residue in the first position (Q-x-x-H-H) instead of a histidine (Napier et al., 1997, Napier et al., 2003, Sperling and Heinz 2001).

Example 8

Intron Removal

Alignment of the three *Primula* clones PaD6D-2 (SEQ ID NO:22), PwD6D (SEQ ID NO:25), and PflD6D (SEQ ID NO:47) revealed extensive similarity between the DNA sequences. PaD6D-2 had approximately 97% identity to PwD6D and approximately 98% identity to PflD6D. PwD6D had approximately 98% identity to PflD6D. A 2-step PCR procedure was utilized to remove the intron region from each gene. Briefly, the procedure entails the amplification of the two exons in separate PCRs, followed by a second round of PCR amplification to combine the two exons together. The same set of primers was used for each gene amplification because of the extensive similarity between the three Δ6 desaturase genes.

Two sets of primers were designed to amplify exon1 from the PwD6D insert in pMON83967. The size of the amplified product was 475 bp and corresponded to exon 1 of PwD6D. The two primers are given below.

Pw F1: 5'-GTCGAC<u>ATG</u>GCTAACAAATCTCAAAC -3'  (SEQ ID NO: 55)

Pw R1: 5'-GTAATGCCCAGAGTCGTGACCTATCCATCCGCACTGGATCC -3'  (SEQ ID NO: 57)

Exon 2 was PCR amplified from pMON83967 using the primer sequences shown below. The size of the amplified product was 875 bp.

Pw F2: 5'- GATCCAGTGCGGATGGATAGGTCACGACTCTGGGCATTACCG -3'  (SEQ ID NO:58)

Pw R2: 5'- CCTGCAGGTCACCCGAGAGT-3'  (SEQ ID NO:56)

The amplified exon1 and exon2 products were then combined together with the primers Pw F1 and Pw R2 to PCR amplify the complete ORF minus the original intron. The resulting 1350 bp fragment was ligated into the yeast expression vector pYES2.1-TOPO giving pMON67062.

The removal of the intron region from PaD6D-2 in pMON83968 and PflD6D in pMON84810 was done utilizing the same procedure as described above for PwD6D. The sizes of the exons were the same as that of PwD6D. The resulting 1350 bp combined exon fragments were ligated into the yeast expression vector pYES2.1-TOPO giving pMON67063 for PaD6D-2 and pMON67064 for PflD6D.

Example 9

Yeast Transformation and Expression

Constructs pMON83950 (FIG. 3), pMON67011 (FIG. 2), pMON67026, pMON67062, pMON67064, and pMON67065 were introduced into the uracil auxotrophic *Saccharomyces cerevisiae* strain INVSc1 (Invitrogen) using the *S. cerevisiae* EasyComp Transformation Kit (Invitrogen). Transformants were selected on plates made of SC minimal media minus uracil with 2% glucose. Colonies of transformants were used to inoculate 5 ml of SC minimal media minus uracil and 2% glucose and were grown overnight at 30° C. For induction, stationary phase yeast cells were pelleted and re-suspended in SC minimal media minus uracil supplemented with 2% galactose and grown for 1 day at 25° C. followed by 3 days at 15° C. When exogenous fatty acids were provide to the cultures, 0.01% (v/v) LA (09, 12-18:2) and 0.01% ALA (Δ9, 12, 15-18:3) were added with the emulsifier 0.1% (w/v) Tergitol. The cultures were grown 1 day at 25° C. followed by 3 days at 15° C., and subsequently harvested by centrifugation. Cell pellets were washed once with sterile TE buffer pH 7.5, to remove the media, and lyophilized for 24 h. The host strain transformed with the vector containing the LacZ gene was used as a negative control in all studies.

FAMEs were prepared from lyophilized yeast pellets by transmethylation with 0.5 mL 5% (v/v) $H_2SO_4$ in methanol containing 0.075 mg/mL 2,6-Di-tert-butyl-4-methoxyphenol for 90 min at 90° C. The FAMEs were extracted by addition of 0.9 mL 10% (w/v) NaCl and 0.3 mL of heptane. The heptane layer containing FAMEs was removed and used directly for GC as described in Example 2.

The results shown in Table 7 demonstrate that *P. juliae* clones pMON67011 and pMON83950, *P. alpicola* clones pMON67026 and pMON67063, *P. waltonii* clone pMON67062, *P. florindae* clone pMON67064, and *P. farinosa* clone pMON67065 exhibit Δ6 desaturase activity in a yeast expression system. The data in Table 8 demonstrate that each *Primula* clone encodes a protein with selectivity for either n-3 or n-6 substrate fatty acids.

TABLE 7

Δ6 desaturase activity of *Primula* clones in a yeast expression system.

| Vector | Gene | FA in medium | LA* | GLA* | ALA* | SDA* |
|---|---|---|---|---|---|---|
| LacZ-1 | LacZ | — | 0.0 | 0.0 | 0.0 | 0.0 |
| LacZ-2 | LacZ | — | 0.0 | 0.0 | 0.0 | 0.0 |
| LacZ-3 | LacZ | — | 0.0 | 0.0 | 0.0 | 0.0 |
| LacZ-1 | LacZ | LA + ALA | 23.5 | 0.0 | 20.6 | 0.0 |
| LacZ-2 | LacZ | LA + ALA | 20.3 | 0.0 | 16.6 | 0.0 |
| LacZ-3 | LacZ | LA + ALA | 29.1 | 0.0 | 28.0 | 0.0 |
| pMON67011 | *P. juliae* D6D-2 | — | 0.0 | 0.0 | 0.0 | 0.0 |
| pMON67011 | *P. juliae* D6D-2 | — | 0.0 | 0.0 | 0.0 | 0.0 |
| pMON67011 | *P. juliae* D6D-2 | — | 0.2 | 0.0 | 0.0 | 0.0 |
| pMON67011 | *P. juliae* D6D-2 | LA + ALA | 18.7 | 6.5 | 12.2 | 8.4 |
| pMON67011 | *P. juliae* D6D-2 | LA + ALA | 14.7 | 5.4 | 9.6 | 7.6 |
| pMON67011 | *P. juliae* D6D-2 | LA + ALA | 18.6 | 5.1 | 14.6 | 8.8 |
| pMON67026 | *P. alpicola* D6D1 | — | 0.0 | 0.0 | 0.0 | 0.0 |
| pMON67026 | *P. alpicola* D6D-1 | — | 0.0 | 0.0 | 0.0 | 0.0 |
| pMON67026 | *P. alpicola* D6D-1 | — | 0.0 | 0.0 | 0.0 | 0.0 |
| pMON67026 | *P. alpicola* D6D-1 | LA + ALA | 23.0 | 3.6 | 21.8 | 1.5 |
| pMON67026 | *P. alpicola* D6D-1 | LA + ALA | 19.1 | 3.7 | 17.9 | 1.5 |
| pMON67026 | *P. alpicola* D6D-1 | LA + ALA | 22.6 | 3.1 | 24.1 | 1.5 |
| pMON83950 | *P. juliae* D6D-1 | — | 0.0 | 0.0 | 0.0 | 0.0 |
| pMON83950 | *P. juliae* D6D-1 | — | 0.0 | 0.0 | 0.0 | 0.0 |
| pMON83950 | *P. juliae* D6D-1 | — | 0.0 | 0.0 | 0.0 | 0.0 |
| pMON83950 | *P. juliae* D6D-1 | LA + ALA | 21.2 | 4.0 | 14.9 | 6.7 |
| pMON83950 | *P. juliae* D6D-1 | LA + ALA | 13.9 | 4.2 | 8.8 | 6.0 |
| pMON83950 | *P. juliae* D6D-1 | LA + ALA | 21.7 | 4.3 | 16.8 | 8.3 |
| pMON67062 | *P. waltonii* D6D | — | 0.0 | 0.0 | 0.0 | 0.0 |
| pMON67062 | *P. waltonii* D6D | — | 0.0 | 0.0 | 0.0 | 0.0 |
| pMON67062 | *P. waltonii* D6D | — | 0.0 | 0.0 | 0.0 | 0.0 |
| pMON67062 | *P. waltonii* D6D | LA + ALA | 17.5 | 5.7 | 12.1 | 7.1 |
| pMON67062 | *P. waltonii* D6D | LA + ALA | 12.8 | 4.8 | 8.6 | 6.0 |
| pMON67062 | *P. waltonii* D6D | LA + ALA | 20.9 | 5.2 | 16.8 | 8.4 |
| pMON67063 | *P. alpicola* D6D-2 | — | 0.0 | 0.0 | 0.0 | 0.0 |
| pMON67063 | *P. alpicola* D6D-2 | — | 0.0 | 0.0 | 0.0 | 0.0 |
| pMON67063 | *P. alpicola* D6D-2 | — | 0.0 | 0.0 | 0.0 | 0.0 |
| pMON67063 | *P. alpicola* D6D-2 | LA + ALA | 19.9 | 3.7 | 13.4 | 6.7 |
| pMON67063 | *P. alpicola* D6D-2 | LA + ALA | 16.0 | 3.6 | 9.5 | 5.6 |
| pMON67063 | *P. alpicola* D6D2- | LA + ALA | 19.8 | 3.6 | 14.9 | 7.8 |
| pMON67064 | *P. florindae* D6D | — | 0.0 | 0.0 | 0.0 | 0.0 |
| pMON67064 | *P. florindae* D6D | — | 0.0 | 0.0 | 0.0 | 0.0 |
| pMON67064 | *P. florindae* D6D | — | 0.0 | 0.0 | 0.0 | 0.0 |
| pMON67064 | *P. florindae* D6D | LA + ALA | 17.4 | 5.6 | 12.0 | 6.9 |
| pMON67064 | *P. florindae* D6D | LA + ALA | 12.8 | 4.8 | 8.3 | 5.9 |
| pMON67064 | *P. florindae* D6D | LA + ALA | 17.1 | 4.5 | 14.6 | 8.3 |
| pMON67065 | *P. farinosa* D6D | — | 0.0 | 0.0 | 0.0 | 0.0 |
| pMON67065 | *P. farinosa* D6D | — | 0.0 | 0.0 | 0.0 | 0.0 |
| pMON67065 | *P. farinosa* D6D | — | 0.0 | 0.0 | 0.0 | 0.0 |
| pMON67065 | *P. farinosa* D6D | LA + ALA | 22.1 | 0.9 | 19.7 | 0.3 |
| pMON67065 | *P. farinosa* D6D | LA + ALA | 28.8 | 0.8 | 27.5 | 0.2 |
| pMON67065 | *P. farinosa* D6D | LA + ALA | 21.1 | 0.8 | 22.7 | 0.3 |

*Reported as a % of the total for all analytes included in the GC-FID chromatogram, including (16:0, 16:1, 18:0, 20:0, 20:1, 20:2, 22:0, 22:1, 22:2)

TABLE 8

Comparison of n-3:n-6 substrate selectivities for *Primula* Δ6 desaturases.

| Sample | Vector | Gene | % conv. GLA* | % conv SDA* | Ratio n-3:n-6 |
|---|---|---|---|---|---|
| 1 | LacZ-1 | LacZ | 0.00 | 0.00 | 0.00 |
| 2 | LacZ-2 | LacZ | 0.00 | 0.00 | 0.00 |
| 3 | LacZ-3 | LacZ | 0.00 | 0.00 | 0.00 |
| 4 | pMON67011 | *P. juliae* D6D-2 | 25.75 | 40.64 | 1.58 |
| 5 | pMON67011 | *P. juliae* D6D-2 | 26.98 | 44.07 | 1.63 |
| 6 | pMON67011 | *P. juliae* D6D-2 | 21.64 | 37.78 | 1.75 |
| 7 | pMON67026 | *P. alpicola* D6D-1 | 13.60 | 6.39 | 0.47 |
| 8 | pMON67026 | *P. alpicola* D6D-1 | 16.06 | 7.83 | 0.49 |
| 9 | pMON67026 | *P. alpicola* D6D-1 | 12.12 | 5.83 | 0.48 |
| 10 | pMON83950 | *P. juliae* D6D-1 | 15.82 | 31.14 | 1.97 |
| 11 | pMON83950 | *P. juliae* D6D-1 | 23.23 | 40.72 | 1.75 |
| 12 | pMON83950 | *P. juliae* D6D-1 | 16.58 | 32.92 | 1.99 |
| 13 | pMON67062 | *P. waltonii* D6D | 24.46 | 36.80 | 1.50 |
| 14 | pMON67062 | *P. waltonii* D6D | 27.05 | 41.15 | 1.52 |
| 15 | pMON67062 | *P. waltonii* D6D | 19.77 | 33.41 | 1.69 |
| 16 | pMON67063 | *P. alpicola* D6D-2 | 15.74 | 33.48 | 2.13 |
| 17 | pMON67063 | *P. alpicola* D6D-2 | 18.53 | 36.82 | 1.99 |
| 18 | pMON67063 | *P. alpicola* D6D-2 | 15.37 | 34.39 | 2.24 |
| 19 | pMON67064 | *P. florindae* D6D | 24.34 | 36.72 | 1.51 |
| 20 | pMON67064 | *P. florindae* D6D | 27.29 | 41.56 | 1.52 |
| 21 | pMON67064 | *P. florindae* D6D | 20.96 | 36.13 | 1.72 |
| 22 | pMON67065 | *P. farinosa* D6D | 4.07 | 1.25 | 0.31 |
| 23 | pMON67065 | *P. farinosa* D6D | 2.77 | 0.79 | 0.29 |
| 24 | pMON67065 | *P. farinosa* D6D | 3.70 | 1.09 | 0.29 |

*The percentage conversion to GLA was calculated by dividing the value for GLA (Table 1) by the sum of the values for LA and GLA (Table 1). The same calculation was made for SDA using the sum of ALA and SDA (Table 1).
**The n-3:n-6 ratio was calculated by dividing the % conv. SDA by % conv. GLA.

Example 10

Arabidopsis Cloning, Transformation and Expression

Figure 8:
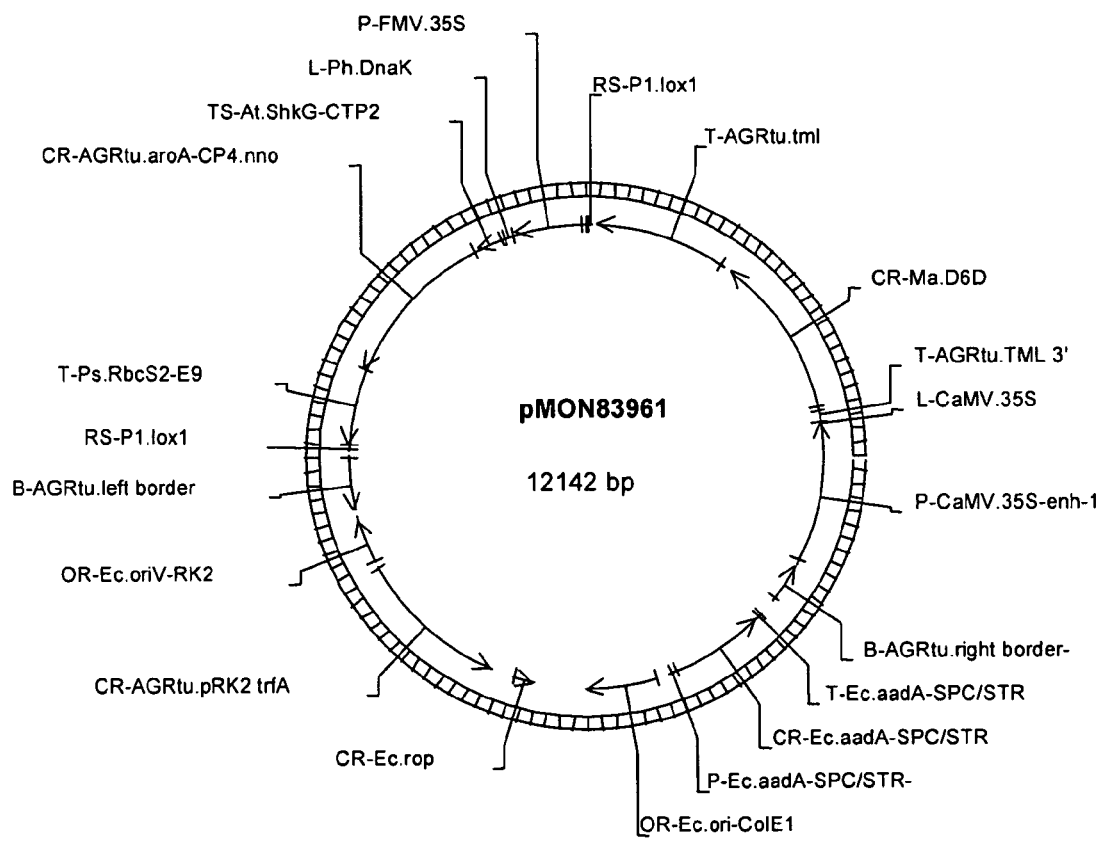
FIG. 8 shows map of vector pMON83961.
Figure 9:
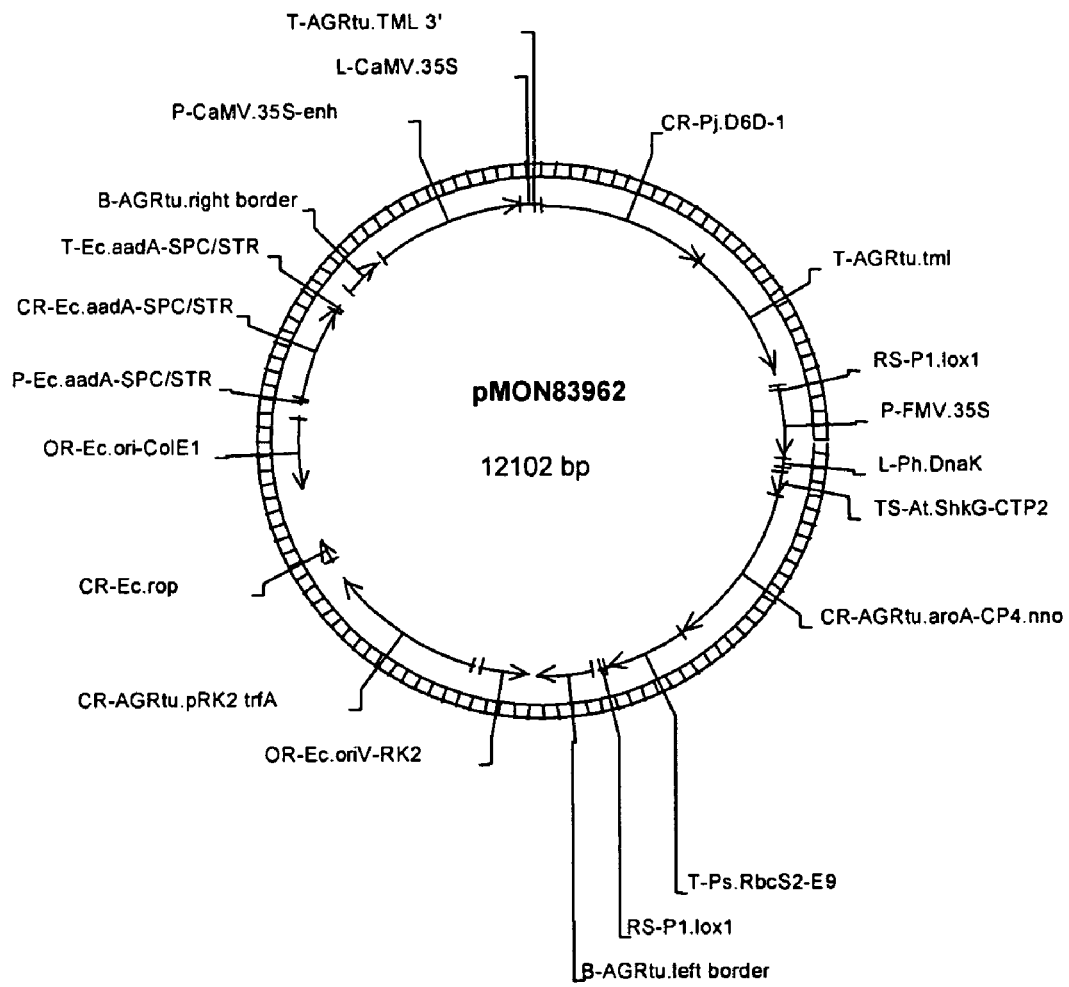
FIG. 9 shows map of vector pMON83962.
Figure 10:
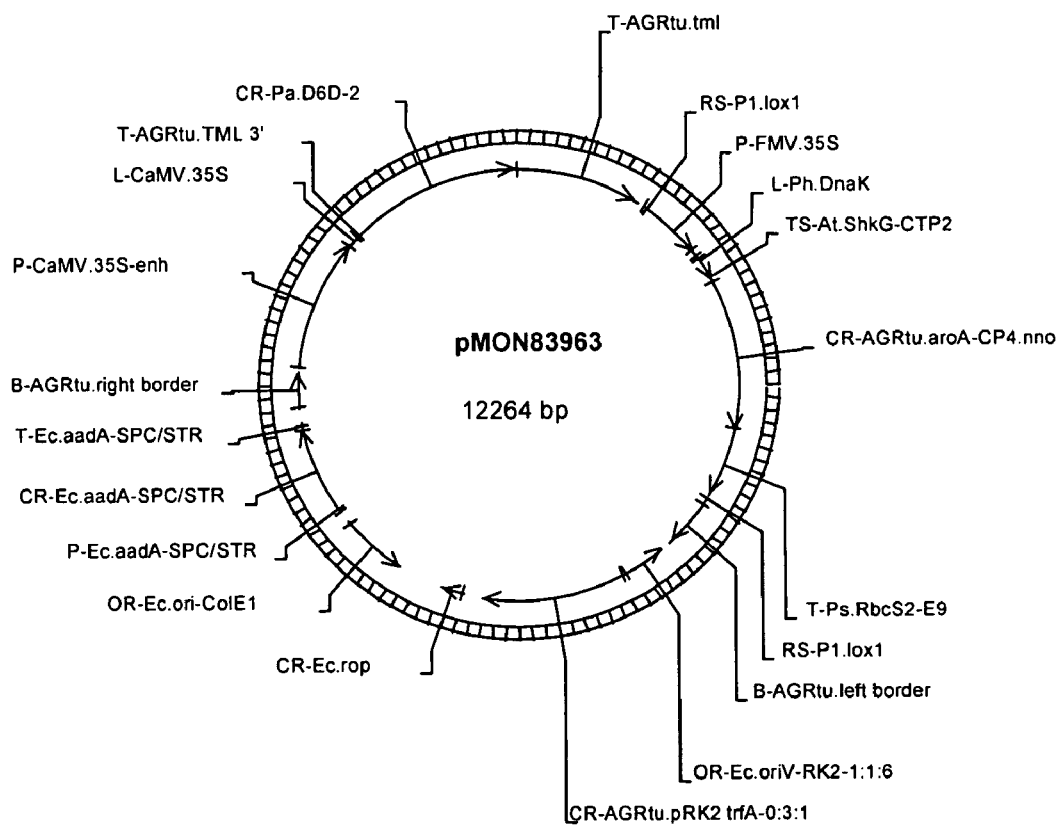
FIG. 10 shows map of vector pMON83963.
Figure 11:
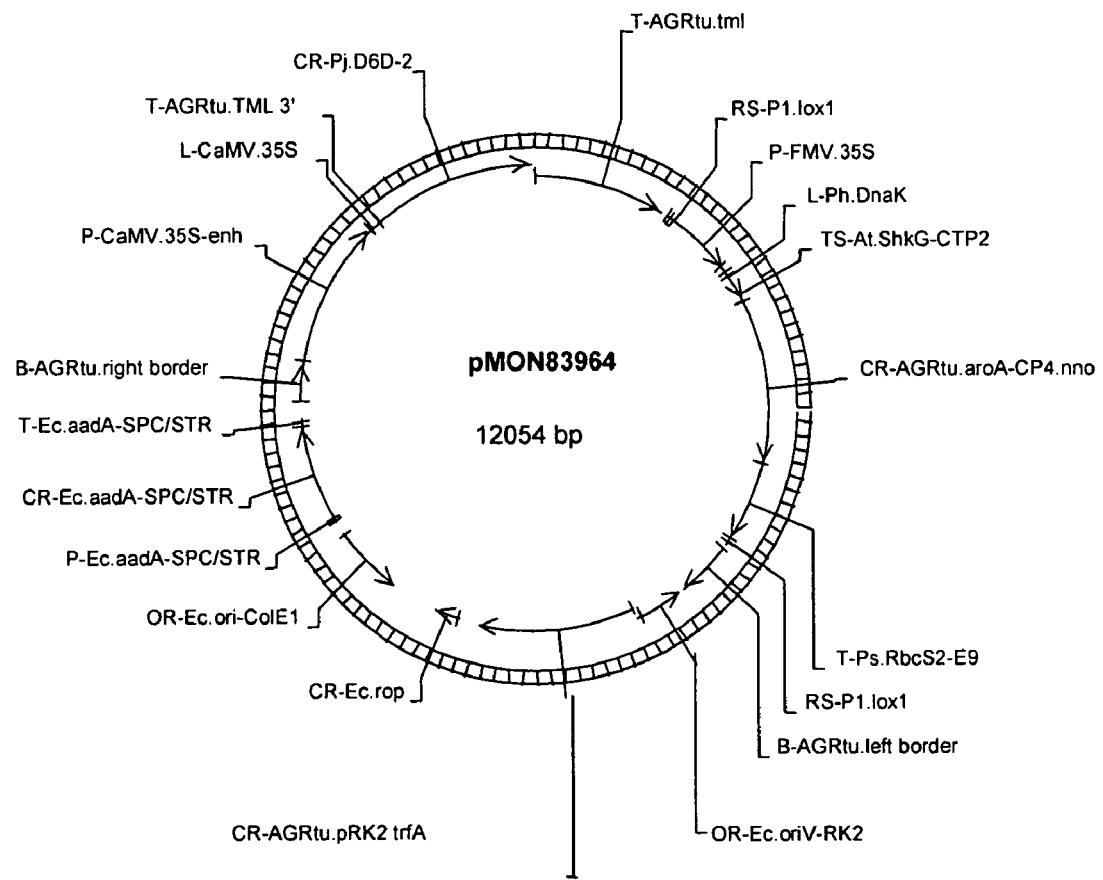
FIG. 11 shows map of vector pMON83964.
Figure 12:
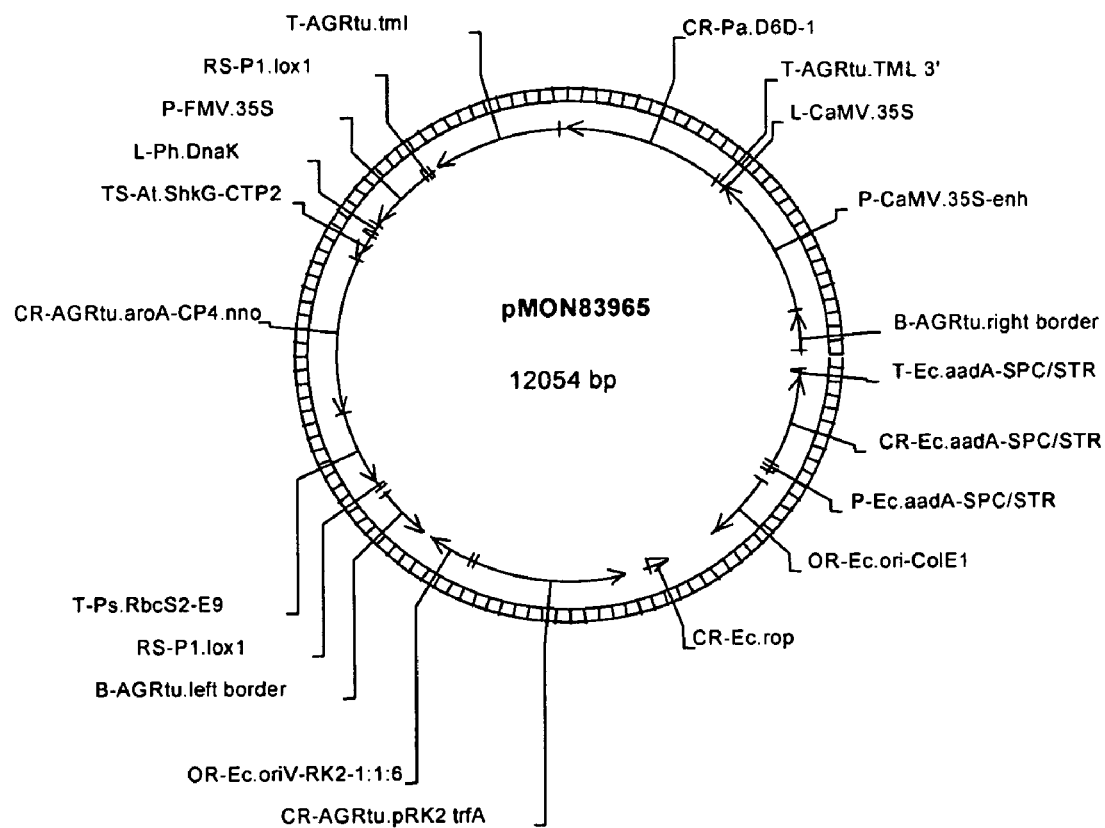
FIG. 12 shows map of vector pMON83965.
Figure 13:
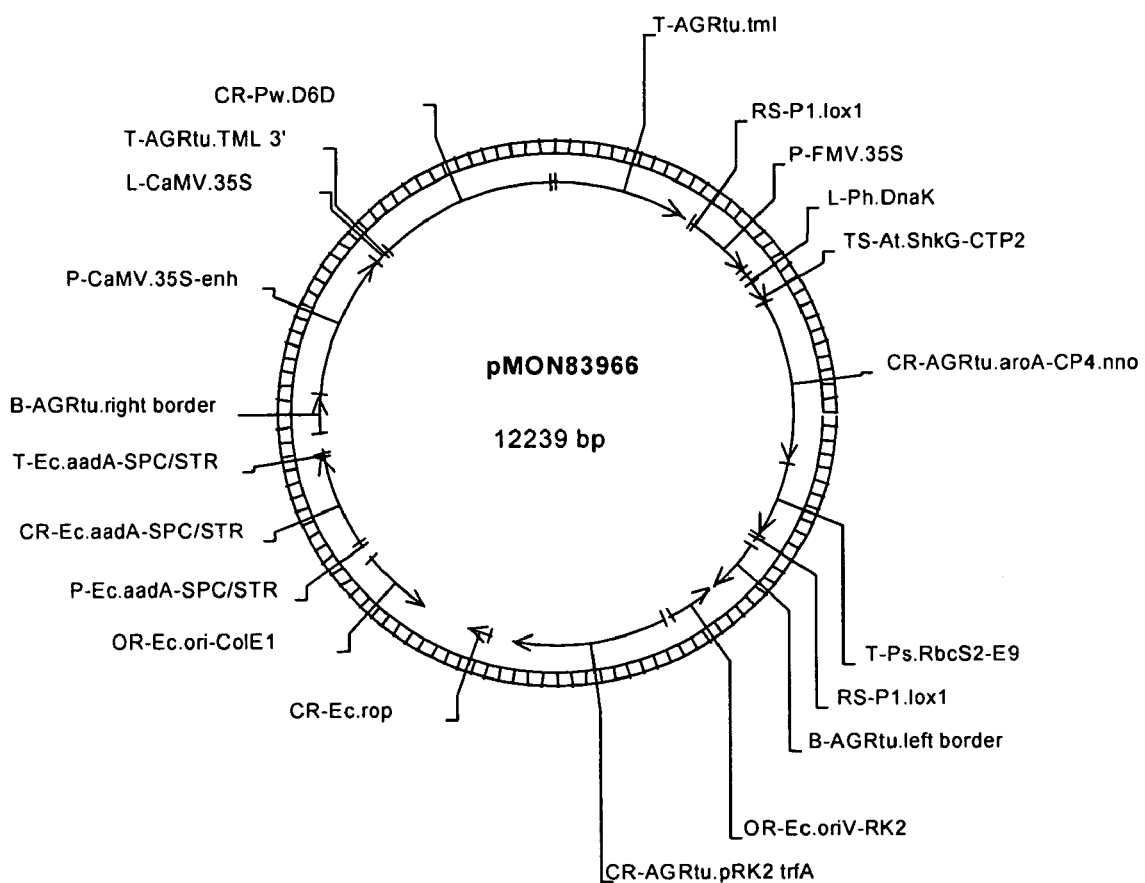
FIG. 13 shows map of vector pMON83966.

After confirming activity of the *Primula* Δ6 desaturases in yeast, the genes were then cloned into pMON73273 (a binary vector containing the constitutive 35S CaMV promoter) for expression in *Arabidopsis thaliana* to determine activity in planta. PwD6D and PaD6D-2 were cloned with introns intact. The following vectors were transformed into *Arabidopsis*: pMON83961 (MaD6D) (FIG. 8), pMON83962 (PjD6D-1) (FIG. 9), pMON83963 (PaD6D-2) (FIG. 10), pMON84964 (PjD6D-2) (FIG. 11), pMON84965 (PaD6D-1) (FIG. 12), and pMON83966 (PwD6D) (FIG. 13).

*Arabidopsis* plants were grown by sowing seeds onto 4 inch pots containing reverse osmosis water (ROW) saturated MetroMix 200 (The Scotts Company, Columbus, Ohio). The plants were vernalized by placing the pots in a covered flat, in a growth chamber at 4-7° C., 8 hours light/day for 4-7 days. The flats were transferred to a growth chamber at 22° C., 55% relative humidity, and 16 hours light/day at an average intensity of 160-200 μEinstein/s/m$^2$. The cover was lifted and slid back 1 inch after germination, and then was removed when the true leaves had formed. The plants were bottom watered, as needed, with ROW until 2-3 weeks after germination. Plants were then bottom watered, as needed, with Plantex 15-15-18 solution (Plantex Corporation Ottawa, Canada) at 50 ppm N$_2$. Pots were thinned so that 1 plant remained per pot at 2-3 weeks after germination. Once the plants began to bolt, the primary inflorescence was trimmed to encourage the growth of axillary bolts.

Transgenic *Arabidopsis thaliana* plants were obtained as described by Bent et al., Science, 265:1856-1860, 1994 or Bechtold et al., *C. R. Acad Sci, Life Sciences,* 316:1194-1199, 1993. Cultures of *Agrobacterium tumefaciens* strain ABI containing one of the transformation vectors pMON69804, pMON69812, or pMON69815 were grown overnight in LB (10% bacto-tryptone, 5% yeast extract, and 10% NaCl with kanamycin (75 mg/L), chloramphenicol (25 mg/L), and spectinomycin (100 mg/L)). The bacterial culture was centrifuged and resuspended in 5% sucrose+0.05% Silwet-77 solution. The aerial portions of whole *Arabidopsis thaliana* Columbia plants (at about 5-7 weeks of age) were immersed in the resulting solution for 2-3 seconds. The excess solution was removed by blotting the plants on paper towels. The dipped plants were placed on their side in a covered flat and transferred to a growth chamber at 19° C. After 16 to 24 hours the dome was removed and the plants were set upright. When plants had reached maturity, water was withheld for 2-7 days prior to seed harvest. Harvested seed was passed through a stainless steel mesh screen (40 holes/inch) to remove debris.

The harvested seeds described above were sown onto flats containing ROW saturated MetroMix 200 (The Scotts Company). The plants were vernalized and germinated as described above. After true leaves had emerged, the seedlings were sprayed with Roundup to select for transformed plants.

The fatty acid composition of mature seed (R2) was determined by GC analysis of methyl ester derived lipids as done above for soybean seed. Values for pooled seed from each transgenic event are shown in Table 9. The n-3 or n-6 substrate selectivities that were observed in the yeast assays were confirmed in planta.

TABLE 9

Fatty Acid Analysis of *Arabidopsis* Seed

| Gene | Pedigree | Construct | PA | SA | OA | LA | GLA | ALA | SDA |
| --- | --- | --- | --- | --- | --- | --- | --- | --- | --- |
| MaD6D | At_S54435:@ | pMON83961 | 7.47 | 3.73 | 14.18 | 26.31 | 2.3 | 17.3 | 0.72 |
| MaD6D | At_S54436:@ | pMON83961 | 7.44 | 3.91 | 14.72 | 25.51 | 1.72 | 18.57 | 0.44 |
| MaD6D | At_S54437:@ | pMON83961 | 7.65 | 3.72 | 14.51 | 28.49 | 0.37 | 17.97 | 0 |
| MaD6D | At_S54438:@ | pMON83961 | 7.65 | 3.53 | 13.55 | 25.48 | 2.09 | 19.18 | 0.87 |
| MaD6D | At_S54439:@ | pMON83961 | 7.7 | 3.51 | 13.69 | 27.81 | 1.63 | 17.07 | 0.45 |
| MaD6D | At_S54440:@ | pMON83961 | 7.38 | 3.55 | 14.42 | 25.95 | 1.6 | 18.26 | 0.53 |
| MaD6D | At_S54441:@ | pMON83961 | 7.24 | 3.54 | 13.53 | 24.24 | 4.4 | 17.68 | 1.52 |
| MaD6D | At_S54442:@ | pMON83961 | 7.29 | 3.6 | 14.7 | 25.31 | 3.58 | 16.45 | 0.98 |
| MaD6D | At_S54443:@ | pMON83961 | 7.01 | 3.61 | 14.46 | 27.25 | 0.44 | 18.49 | 0 |
| MaD6D | At_S54444:@ | pMON83961 | 7.68 | 3.75 | 14.34 | 27.89 | 1.19 | 17.95 | 0.05 |
| PjD6D-1 | At_S54446:@ | pMON83962 | 7.5 | 3.34 | 13.52 | 25.05 | 2.06 | 13.81 | 5.93 |
| PjD6D-1 | At_S54447:@ | pMON83962 | 7.29 | 3.15 | 14.03 | 26.18 | 1.64 | 14 | 5.25 |
| PjD6D-1 | At_S54448:@ | pMON83962 | 7.2 | 3.08 | 13.37 | 27.24 | 0.49 | 17 | 2.72 |
| PjD6D-1 | At_S54449:@ | pMON83962 | 7.24 | 3.17 | 14.28 | 27.52 | 0.46 | 16.65 | 2.44 |
| PjD6D-1 | At_S54450:@ | pMON83962 | 7.24 | 3.18 | 13.38 | 26.3 | 1.32 | 15.16 | 4.92 |
| PjD6D-1 | At_S54451:@ | pMON83962 | 7.53 | 3.04 | 14.49 | 28.01 | 1.8 | 13.03 | 4.79 |
| PjD6D-1 | At_S54452:@ | pMON83962 | 7.59 | 3.44 | 13.16 | 25.54 | 1.72 | 13.3 | 6.69 |
| PjD6D-1 | At_S54453:@ | pMON83962 | 7.22 | 3.21 | 14.05 | 26.72 | 1.14 | 14.35 | 4.48 |
| PjD6D-1 | At_S54454:@ | pMON83962 | 6.98 | 3.23 | 13.48 | 25.12 | 2.27 | 12.62 | 6.55 |
| PjD6D-1 | At_S54455:@ | pMON83962 | 7.34 | 3.18 | 14.63 | 27.07 | 0.16 | 18.57 | 1.1 |
| PjD6D-1 | At_S54456:@ | pMON83962 | 7.26 | 3.44 | 15.8 | 27.83 | 0.5 | 15.81 | 2.45 |
| PjD6D-1 | At_S54457:@ | pMON83962 | 7.41 | 3.11 | 14.03 | 27.39 | 1.92 | 12.97 | 4.95 |
| PjD6D-1 | At_S54458:@ | pMON83962 | 7.2 | 3.26 | 13.38 | 26.18 | 1.31 | 14.54 | 5.1 |
| PjD6D-1 | At_S54459:@ | pMON83962 | 7.23 | 3.16 | 13.25 | 26.38 | 1.32 | 15.07 | 4.46 |
| PjD6D-1 | At_S54460:@ | pMON83962 | 7.21 | 3.19 | 13.48 | 26.35 | 1.32 | 14.36 | 5.16 |
| PjD6D-1 | At_S54461:@ | pMON83962 | 7.18 | 3.34 | 13.5 | 26.64 | 0.79 | 15.65 | 3.96 |
| PjD6D-1 | At_S54462:@ | pMON83962 | 7.11 | 3.15 | 13.88 | 27.28 | 1.12 | 15.02 | 3.84 |
| PjD6D-1 | At_S54463:@ | pMON83962 | 7.4 | 3.19 | 13.37 | 26.35 | 0.61 | 17.58 | 2.93 |
| PjD6D-1 | At_S54464:@ | pMON83962 | 7.57 | 3.34 | 13.72 | 26.12 | 1.24 | 15.26 | 4.69 |
| PaD6D-2 | At_S54466:@ | pMON83963 | 7.25 | 3.18 | 14.44 | 26.54 | 1.46 | 14.44 | 4.45 |
| PaD6D-2 | At_S54467:@ | pMON83963 | 7.28 | 3.07 | 14.66 | 27.82 | 0.31 | 17.25 | 1.59 |
| PaD6D-2 | At_S54468:@ | pMON83963 | 7.34 | 3.22 | 15.05 | 26.37 | 2.01 | 13.14 | 4.86 |
| PaD6D-2 | At_S54469:@ | pMON83963 | 6.91 | 2.94 | 14.35 | 26.77 | 1.32 | 14.33 | 4.38 |
| PaD6D-2 | At_S54470:@ | pMON83963 | 7.36 | 3.26 | 13.31 | 27.8 | 1.36 | 13.39 | 4.52 |
| PaD6D-2 | At_S54471:@ | pMON83963 | 7.14 | 3.07 | 14.38 | 25.73 | 3.26 | 11.32 | 6.18 |

TABLE 9-continued

Fatty Acid Analysis of *Arabidopsis* Seed

| Gene | Pedigree | Construct | PA | SA | OA | LA | GLA | ALA | SDA |
|---|---|---|---|---|---|---|---|---|---|
| PaD6D-2 | At_S54472:@ | pMON83963 | 7.67 | 3.28 | 14.01 | 27.82 | 0 | 19.54 | 0.3 |
| PaD6D-2 | At_S54473:@ | pMON83963 | 7.48 | 3.27 | 13.95 | 26.26 | 2.12 | 13.24 | 5.57 |
| PaD6D-2 | At_S54474:@ | pMON83963 | 7.22 | 3.01 | 14.95 | 27.87 | 1.02 | 14.5 | 3.48 |
| PaD6D-2 | At_S54475:@ | pMON83963 | 7.44 | 3.07 | 13.33 | 26.46 | 1.58 | 14.27 | 5.24 |
| PaD6D-2 | At_S54476:@ | pMON83963 | 7.35 | 3.17 | 14.22 | 27.48 | 0.8 | 15.51 | 3.25 |
| PaD6D-2 | At_S54477:@ | pMON83963 | 8.01 | 2.7 | 15.85 | 30.18 | 0 | 16.8 | 0 |
| PaD6D-2 | At_S54478:@ | pMON83963 | 7.45 | 3.05 | 13.47 | 27.48 | 0.13 | 19.53 | 0.84 |
| PaD6D-2 | At_S54479:@ | pMON83963 | 7.14 | 2.99 | 15.32 | 27.71 | 0.24 | 17.74 | 0.9 |
| PaD6D-2 | At_S54480:@ | pMON83963 | 7.37 | 3.1 | 14.8 | 27.87 | 0.07 | 18.64 | 0.45 |
| PaD6D-2 | At_S54481:@ | pMON83963 | 7.39 | 3.2 | 13.49 | 27.32 | 0.1 | 19.9 | 0.6 |
| PaD6D-2 | At_S54482:@ | pMON83963 | 7.29 | 3.1 | 13.72 | 27.63 | 0.25 | 17.96 | 1.63 |
| PaD6D-2 | At_S54483:@ | pMON83963 | 7.04 | 2.97 | 15.2 | 28.08 | 0 | 18.71 | 0.1 |
| PaD6D-2 | At_S54484:@ | pMON83963 | 7.09 | 2.89 | 14.89 | 28.18 | 0.05 | 19.73 | 0 |
| PaD6D-2 | At_S54485:@ | pMON83963 | 7.17 | 2.93 | 15.33 | 27.21 | 1.52 | 13.48 | 4.57 |
| PjD6D-2 | At_S54487:@ | pMON83964 | 7.18 | 3.06 | 14.91 | 27.66 | 0.79 | 15.58 | 3 |
| PjD6D-2 | At_S54488:@ | pMON83964 | 7.36 | 3.09 | 14.13 | 27.75 | 1.34 | 14.21 | 4.15 |
| PjD6D-2 | At_S54489:@ | pMON83964 | 7.48 | 2.9 | 13.86 | 27.52 | 0.6 | 16.94 | 2.95 |
| PjD6D-2 | At_S54490:@ | pMON83964 | 7.39 | 3.08 | 14.12 | 27.93 | 0.63 | 16.23 | 2.88 |
| PjD6D-2 | At_S54491:@ | pMON83964 | 7.35 | 3.05 | 15.03 | 28.07 | 0 | 19.04 | 0.16 |
| PjD6D-2 | At_S54492:@ | pMON83964 | 7.59 | 3.07 | 14.84 | 27.99 | 0 | 19.18 | 0.33 |
| PjD6D-2 | At_S54493:@ | pMON83964 | 7.36 | 2.97 | 13.57 | 28.18 | 0.68 | 16.38 | 2.96 |
| PjD6D-2 | At_S54494:@ | pMON83964 | 7.39 | 3.03 | 13.37 | 27.5 | 0.98 | 15.71 | 3.96 |
| PjD6D-2 | At_S54495:@ | pMON83964 | 7.46 | 2.98 | 13.59 | 26.97 | 1.02 | 16.11 | 3.83 |
| PjD6D-2 | At_S54496:@ | pMON83964 | 7.65 | 3.02 | 14.54 | 27.83 | 0.35 | 17.43 | 1.87 |
| PjD6D-2 | At_S54497:@ | pMON83964 | 7.62 | 2.94 | 13.64 | 28.44 | 0.89 | 15.27 | 3.61 |
| PjD6D-2 | At_S54498:@ | pMON83964 | 7.55 | 3.06 | 14.06 | 27.53 | 1.01 | 14.89 | 4.37 |
| PjD6D-2 | At_S54499:@ | pMON83964 | 7.19 | 3.12 | 14.62 | 26.77 | 1.55 | 13.28 | 5.14 |
| PjD6D-2 | At_S54500:@ | pMON83964 | 7.42 | 2.9 | 13.83 | 27.84 | 0.39 | 17.55 | 2.3 |
| PjD6D-2 | At_S54501:@ | pMON83964 | 7.51 | 3.09 | 14.23 | 28.21 | 0 | 19.5 | 0.1 |
| PjD6D-2 | At_S54502:@ | pMON83964 | 7.41 | 3 | 13.56 | 27.41 | 0.81 | 16.36 | 3.33 |
| PjD6D-2 | At_S54503:@ | pMON83964 | 7.33 | 2.95 | 13.46 | 26.74 | 1.09 | 15.92 | 4.28 |
| PaD6D-1 | At_S54505:@ | pMON83965 | 7.24 | 2.97 | 14.25 | 27.24 | 0.96 | 19.3 | 0.21 |
| PaD6D-1 | At_S54506:@ | pMON83965 | 7.37 | 3.12 | 14.25 | 26.81 | 1.26 | 19.08 | 0.24 |
| PaD6D-1 | At_S54507:@ | pMON83965 | 7.48 | 3.03 | 15.61 | 26.86 | 0.52 | 18.75 | 0.09 |
| PaD6D-1 | At_S54508:@ | pMON83965 | 7.61 | 3.07 | 13.41 | 25.28 | 2.2 | 19.67 | 0.51 |
| PaD6D-1 | At_S54509:@ | pMON83965 | 7.33 | 3.24 | 14.21 | 25.71 | 2.32 | 18.64 | 0.48 |
| PaD6D-1 | At_S54510:@ | pMON83965 | 7.66 | 3.09 | 15.86 | 24.84 | 1.1 | 18.88 | 0.23 |
| PaD6D-1 | At_S54511:@ | pMON83965 | 7.55 | 3.08 | 15.2 | 25.25 | 0.94 | 19.36 | 0.21 |
| PaD6D-1 | At_S54512:@ | pMON83965 | 7.43 | 3.16 | 13.51 | 26 | 1.37 | 19.63 | 0.29 |
| PaD6D-1 | At_S54513:@ | pMON83965 | 8.11 | 3.3 | 14.94 | 24.33 | 0.45 | 20.26 | 0.12 |
| PaD6D-1 | At_S54514:@ | pMON83965 | 7.35 | 3.14 | 14.18 | 26.35 | 1.36 | 19.27 | 0.36 |
| PaD6D-1 | At_S54515:@ | pMON83965 | 7.52 | 2.95 | 12.14 | 26.65 | 0.63 | 22.45 | 0.21 |
| PaD6D-1 | At_S54516:@ | pMON83965 | 7.86 | 3.29 | 15.13 | 23.72 | 0.74 | 20.03 | 0.21 |
| PaD6D-1 | At_S54517:@ | pMON83965 | 7.2 | 3.49 | 15.25 | 27.77 | 0.26 | 18.14 | 0 |
| PaD6D-1 | At_S54518:@ | pMON83965 | 7.17 | 2.81 | 15.7 | 23.13 | 0.06 | 20.4 | 0 |
| PaD6D-1 | At_S54519:@ | pMON83965 | 6.9 | 3.07 | 15.34 | 26.65 | 0.14 | 19.19 | 0 |
| PaD6D-1 | At_S54520:@ | pMON83965 | 8.64 | 3.7 | 15.97 | 20.96 | 0.97 | 18.39 | 0.28 |
| PaD6D-1 | At_S54521:@ | pMON83965 | 7.2 | 3.19 | 13.39 | 26.03 | 1.63 | 19.36 | 0.32 |
| PaD6D-1 | At_S54522:@ | pMON83965 | 8.77 | 3.69 | 15.83 | 20.94 | 0 | 18.92 | 0 |
| PaD6D-1 | At_S54523:@ | pMON83965 | 7.43 | 3.33 | 14.1 | 26.94 | 0.23 | 19.93 | 0 |
| PwD6D | At_S54524:@ | pMON83966 | 7.37 | 3.17 | 15.27 | 25.68 | 2.72 | 13.22 | 4.36 |
| PwD6D | At_S54525:@ | pMON83966 | 7.15 | 3.38 | 14.38 | 25.61 | 2.86 | 12.9 | 4.82 |
| PwD6D | At_S54526:@ | pMON83966 | 6.87 | 3.6 | 14.68 | 27.25 | 0.23 | 17.54 | 1.19 |
| PwD6D | At_S54527:@ | pMON83966 | 7.01 | 3.45 | 15.06 | 26.18 | 1.43 | 14.72 | 3.88 |
| PwD6D | At_S54528:@ | pMON83966 | 7.21 | 3.04 | 14.6 | 27.87 | 0.11 | 18.52 | 0.65 |
| PwD6D | At_S54530:@ | pMON83966 | 7.59 | 3.17 | 15.34 | 21.81 | 0.77 | 17.64 | 2.92 |
| PwD6D | At_S54531:@ | pMON83966 | 7.4 | 3.58 | 14.39 | 26.71 | 0.4 | 17.68 | 1.74 |
| PwD6D | At_S54532:@ | pMON83966 | 6.28 | 3.44 | 14.76 | 24.09 | 2.51 | 12.87 | 6.1 |
| PwD6D | At_S54533:@ | pMON83966 | 7.01 | 3.48 | 14.15 | 25.54 | 2.01 | 12.98 | 5.54 |
| PwD6D | At_S54534:@ | pMON83966 | 7.35 | 3.35 | 14.6 | 26.37 | 2.25 | 13.61 | 4.32 |
| PwD6D | At_S54535:@ | pMON83966 | 7.24 | 3.56 | 14.59 | 27.04 | 0.45 | 17.02 | 2.17 |
| PwD6D | At_S54536:@ | pMON83966 | 7.22 | 3.54 | 13.14 | 25.92 | 1.49 | 15.35 | 4.53 |
| PwD6D | At_S54537:@ | pMON83966 | 7.18 | 3.6 | 13.51 | 26.27 | 1.61 | 15.03 | 4.02 |
| PwD6D | At_S54538:@ | pMON83966 | 7.75 | 3.29 | 13.57 | 25.43 | 2.33 | 13.96 | 5.35 |
| PwD6D | At_S54539:@ | pMON83966 | 7.15 | 3.13 | 14.86 | 26.63 | 0.16 | 18.99 | 0.35 |
| PwD6D | At_S54540:@ | pMON83966 | 7.66 | 3.28 | 14.22 | 26.2 | 0.97 | 16.45 | 3.24 |
| PwD6D | At_S54541:@ | pMON83966 | 7.39 | 2.98 | 13.83 | 27.29 | 0 | 20.28 | 0 |
| PwD6D | At_S54542:@ | pMON83966 | 7.39 | 3.32 | 14.71 | 26.08 | 1.56 | 14 | 4.18 |
| control | At_S54543:@ | pMON26140 | 6.82 | 3.04 | 14.82 | 25.91 | 0 | 20.07 | 0 |
| control | At_S54544:@ | pMON26140 | 7.49 | 3.23 | 13.69 | 27.33 | 0 | 19.77 | 0 |
| control | At_S54545:@ | pMON26140 | 7.32 | 3.23 | 15.05 | 27.47 | 0 | 18.6 | 0 |
| control | At_S54546:@ | pMON26140 | 7.52 | 3.3 | 13.73 | 27.15 | 0 | 19.86 | 0 |
| control | At_S54547:@ | pMON26140 | 7.44 | 3.21 | 14.21 | 27.43 | 0 | 19.36 | 0 |
| control | At_S54548:@ | pMON26140 | 7.39 | 3.25 | 14.1 | 27.05 | 0 | 19.59 | 0 |
| control | At_S54549:@ | pMON26140 | 7.71 | 3.28 | 13.61 | 27.98 | 0 | 20 | 0 |
| control | At_S54550:@ | pMON26140 | 7.62 | 3.24 | 13.58 | 28.28 | 0 | 18.83 | 0 |

TABLE 9-continued

Fatty Acid Analysis of *Arabidopsis* Seed

| Gene | Pedigree | Construct | PA | SA | OA | LA | GLA | ALA | SDA |
|---|---|---|---|---|---|---|---|---|---|
| control | At_S54551:@ | pMON26140 | 7.52 | 3.18 | 14.73 | 27.27 | 0 | 19.78 | 0 |
| control | At_S54552:@ | pMON26140 | 7.44 | 3.21 | 14.95 | 27.69 | 0 | 18.43 | 0 |
| control | At_S54553:@ | pMON26140 | 7.72 | 3.26 | 13.74 | 27.2 | 0 | 19.94 | 0 |
| control | At_S54554:@ | pMON26140 | 7.3 | 3.11 | 15.09 | 27.73 | 0 | 18.75 | 0 |
| control | At_S54555:@ | pMON26140 | 7.44 | 2.99 | 14.51 | 29.21 | 0 | 18.34 | 0 |
| control | At_S54556:@ | pMON26140 | 7.52 | 3.19 | 15.22 | 27.24 | 0 | 18.92 | 0 |
| control | At_S54557:@ | pMON26140 | 7.49 | 3.07 | 14.6 | 28.87 | 0 | 18.17 | 0 |
| control | At_S54558:@ | pMON26140 | 7.45 | 3.11 | 14.72 | 27.88 | 0 | 18.88 | 0 |
| control | At_S54559:@ | pMON26140 | 7.63 | 3.26 | 14.39 | 27.12 | 0 | 19.57 | 0 |
| control | At_S54560:@ | pMON26140 | 7.74 | 3.15 | 13.17 | 28.5 | 0 | 19.61 | 0 |
| control | At_S54561:@ | pMON26140 | 7.39 | 3.15 | 14.34 | 27.06 | 0 | 19.42 | 0 |
| control | At_S54562:@ | pMON26140 | 7.25 | 3.12 | 15.78 | 27.96 | 0 | 17.93 | 0 |
| control | At_S54563:@ | pMON26140 | 7.59 | 3.24 | 14.32 | 27.2 | 0 | 19.54 | 0 |
| control | At_S54564:@ | pMON26140 | 6.73 | 2.82 | 16.17 | 26.66 | 0 | 18.63 | 0 |
| control | At_S54565:@ | pMON26140 | 7.2 | 3 | 15.14 | 27.78 | 0 | 18.66 | 0 |
| control | At_S54566:@ | pMON26140 | 7.33 | 3.16 | 14.6 | 27.28 | 0 | 19.26 | 0 |

Example 10

Canola Transformation and Expression

The vectors pMON83961, pMON83962, pMON83963, and pMON83964 described in Example 9 were also transformed into Canola according to the methods in Example 4. pMON70500 was included as a negative control. The fatty acid composition of leaves was determined by GC analysis of methyl ester derived lipids. The data is shown in Table 10. Again the substrate selectivities observed in yeast and *Arabidopsis* were confirmed.

TABLE 10

Fatty Acid Analysis of Canola Leaf Tissue

| Event | Construct | PA | SA | OA | LA | GLA | ALA | SDA |
|---|---|---|---|---|---|---|---|---|
| BN_G8912 | pMON70500 | 11.64 | 0.63 | 0.39 | 10.68 | 0 | 53.2 | 0 |
| BN_G8913 | pMON70500 | 12.31 | 0.79 | 0.57 | 11.93 | 0 | 53.87 | 0 |
| BN_G8914 | pMON70500 | 16.59 | 1.72 | 2.09 | 20.81 | 0 | 47.72 | 0 |
| BN_G8915 | pMON70500 | 11.74 | 0.82 | 0.27 | 7.86 | 0 | 58.66 | 0 |
| BN_G8918 | pMON70500 | 10.14 | 0.59 | 0.35 | 11.18 | 0 | 52.94 | 0 |
| BN_G8919 | pMON70500 | 10.47 | 0.75 | 0.43 | 13.63 | 0 | 50.63 | 0 |
| BN_G8925 | pMON70500 | 11.3 | 0.72 | 0.51 | 13.69 | 0 | 50.95 | 0 |
| BN_G8926 | pMON70500 | 11.61 | 0.84 | 0.77 | 15.8 | 0 | 49.08 | 0 |
| BN_G8928 | pMON70500 | 10.93 | 0.69 | 0.63 | 16.22 | 0 | 49.41 | 0 |
| BN_G8929 | pMON70500 | 15.53 | 2.06 | 2.18 | 13.04 | 0 | 47.53 | 0 |
| BN_G9007 | pMON83961 | 14.54 | 1.83 | 2.23 | 11.27 | 3.3 | 46.08 | 1.5 |
| BN_G9008 | pMON83961 | 16.91 | 2.38 | 1.41 | 10.26 | 3.81 | 46.21 | 2.01 |
| BN_G9009 | pMON83961 | 17.11 | 1.86 | 3.04 | 16.21 | 0.48 | 47.15 | 0.23 |
| BN_G9011 | pMON83961 | 18.45 | 2.27 | 3.2 | 19.45 | 7.25 | 37.69 | 1.95 |
| BN_G9013 | pMON83961 | 17.95 | 2.39 | 2.66 | 20.5 | 1.29 | 44.84 | 0.37 |
| BN_G9014 | pMON83961 | 16.65 | 1.94 | 1.83 | 12 | 4.73 | 42.26 | 2.79 |
| BN_G9033 | pMON83962 | 16.89 | 2.23 | 1.16 | 16.35 | 0 | 50.45 | 2.52 |
| BN_G9034 | pMON83962 | 15.83 | 2.16 | 1.64 | 15.89 | 0 | 50.66 | 1.11 |
| BN_G9035 | pMON83962 | 16.36 | 3.18 | 2.74 | 23 | 0 | 40.73 | 3.14 |
| BN_G9036 | pMON83962 | 17.01 | 2.65 | 2.4 | 21.09 | 0.37 | 41.23 | 5.12 |
| BN_G9037 | pMON83962 | 16.08 | 2.64 | 1.82 | 17.68 | 0.17 | 44.39 | 3.29 |
| BN_G8828 | pMON83963 | 13.18 | 1.32 | 2.58 | 14 | 0.15 | 47.07 | 4.1 |
| BN_G8829 | pMON83963 | 11.56 | 1.34 | 1.42 | 12.07 | 0.66 | 37.31 | 7.55 |
| BN_G8830 | pMON83963 | 12.49 | 1.37 | 1.31 | 12.24 | 0.31 | 41.45 | 5.87 |
| BN_G9020 | pMON83963 | 16.66 | 2.54 | 4.3 | 23.54 | 1.42 | 41.6 | 0 |
| BN_G9021 | pMON83963 | 16.72 | 1.91 | 2.01 | 14.58 | 0 | 47.55 | 1.36 |
| BN_G9024 | pMON83964 | 18.32 | 2.63 | 2.14 | 25.17 | 0.63 | 37.29 | 5.34 |
| BN_G9025 | pMON83964 | 18.41 | 2.42 | 3.16 | 26.57 | 0 | 39.23 | 0.51 |
| BN_G9026 | pMON83964 | 12.23 | 1.53 | 1.8 | 15.08 | 0.14 | 42.48 | 2.99 |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,826,877
U.S. Pat. No. 4,910,141
U.S. Pat. No. 5,011,770
U.S. Pat. No. 5,158,975
U.S. Pat. No. 5,302,523
U.S. Pat. No. 5,378,619
U.S. Pat. No. 5,384,253
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,591,616
U.S. Pat. No. 5,952,544
U.S. Pat. No. 6,603,061
Ausubel et al., In: Current Protocols in Molecular Biology, Green Publishing Assoc., NY, 1994.
Baerson et al., *Plant Mol. Biol.,* 22(2):255-267, 1993.
Bevan et al., *Nucleic Acids Res.,* 11(2):369-385, 1983.
Bevan, *Nucleic Acids Res.,* 12:8111, 1984.
Bustos et al., *J. Bacteriol.,* 174:7525-7533, 1991.
Bustos, et al., *Plant Cell,* 1(9):839-853, 1989.
Callis et al., *Genes Dev.,* 1:1183-1200, 1987.
Chen et al., *Proc. Natl. Acad. Sci. USA,* 83:8560-8564, 1986.
Chou and Fasman, *Adv. Enzymol.,* 47:45-148, 1978.
de Deckerer, *Eur. J. Clin. Nutr.,* 52:749, 1998.
Garcia-Maroto et al., *Lipids,* 37 (4), 2002
Gelvin et al., In: *Plant Molecular Biology Manual,* 1990.
Goeddel, In: *Methods in Enzymology,* Perbal (Ed.), Academic Press, John Wiley and Sones, 185, 1988.
Hamilton et al., *Proc. Natl. Acad. Sci. USA,* 93(18):9975-9979, 1996.
Hong et al., *Plant Mol. Biol.,* 34(3):549-555, 1997.
Horrobin et al., *Am. J. Clin. Nutr.,* 57(Suppl):732S-737S, 1993.
Horsch et al., *Science,* 227:1229, 1985.
Huang, *Biochem. Biophys. Acta,* 1082:319, 1991.
James et al., *Semin. Arthritis Rheum.,* 28:85, 2000.
Kaeppler et al., *Plant Cell Reports,* 9:415-418, 1990.
Koncz and Schell, *Mol. Gen. Genet.,* 204:383-396, 1986.
Kridl et al., *Seed Sci. Res.,* 1:209:219, 1991.
Kyte and Doolittle, *J. Mol. Biol.,* 157:105-132, 1982.
Manzioris et al., *Am. J. Clin. Nutr.,* 59:1304, 1994.
Michaelis et al., *Ann. Rev. Microbiol.,* 36:425, 1982.
Napier et al., *Biochem. J,* 328, 717-720, 1997.
Napier et al., *Prostaglandins Leukot. Essent. Fatty Acids,* 68 (2), 135-143, 2003.
Naylor et al., *Nature,* 405:1017, 2000.
Omirulleh et al., *Plant Mol. Biol.,* 21(3):415-28, 1993.
PCT Appl. US03/16144
PCT Appl. WO 96/33155
PCT Appl. WO 03/06870
Pedersen et al., *Cell,* 29:1015-1026, 1982.
Potrykus et al., *Mol. Gen. Genet.,* 199(2):169-77, 1985.
Potrykus et al., *Mol. Gen. Genet.,* 199:183-188, 1985.
Radke et al., *Plant Cell Reports,* 11:499-505, 1992.
Reed et al., *Plant Physiol.,* 122:715-720, 2000.
Riggs, et al., *Plant Cell,* 1(6):609-621, 1989.
Russell et al., *Transgenic Res.,* 6(2):157-168
Sambrook et al., In: *Molecular cloning,* Cold Spring Harbor Laboratory Press, Cold Spring Harbor, N.Y., 2001.
Sayanova et al., *FEBS Let.,* 542:100-104, 2003.
Sayanova et al., *Plant Physiol.,* 121, 641-646, 1999.
Shanidin et al., *Biochemistry* 33, 12787-12794, 1994.
Simopoulos et al., *Am. Coll. Nutr.,* 18:487, 1999.
Slocombe et al., *Plant Physiol.,* 104(4):167-176, 1994.
Sperling and Heinz, *Eur. J. Lipid Sci. Technolo.,* 103, 158-180, 2001.
Van den Broeck et al., *Nature,* 313:358, 1985.
Vasil et al., *Plant Physiol.,* 91:1575-1579, 1989.
Wolk et al., *Proc. Natl. Acad. Sci. USA,* 1561-1565, 1984.
Yamazaki et al., *Biochem. Biophys. Acta,* 1123:18, 1992.

What is claimed is:

1. A method of feeding an animal comprising the following steps:
   a. providing a soybean seed oil comprising SDA and GLA;
   b. providing starting feed ingredients;
   c. combining said seed oil and said feed ingredients to make a feed;
   d. feeding said feed to an animal; and
   wherein said feed has a ratio of SDA/GLA of at least about 1.3.

2. The method of claim 1 wherein said soybean seed oil comprises at least about 1% SDA.

3. The method of claim 2 wherein said soybean seed oil comprises at least about 5% SDA.

4. The method of claim 3 wherein said ratio of SDA/GLA is at least about 1.5.

5. The method of claim 4 wherein said ratio of SDA/GLA is at least about 2.0.

6. The method of claim 5 wherein said ratio of SDA/GLA is at least about 2.5.

7. The method of claim 6 wherein said ratio of SDA/GLA is at least about 3.0.

8. The method of claim 7 wherein said seed oil further comprises ALA.

9. The method of claim 8 wherein said seed oil has a ratio of SDA/ALA of at least about 0.5.

10. The method of claim 9 wherein said ratio of SDA/ALA is at least about 1.0.

11. The method of claim 10 wherein said ratio of SDA/ALA is at least about 1.5.

12. The method of claim 11 wherein said ratio of SDA/ALA is less than about 1.8.

13. The method of claim 1 wherein said feed comprises soybean seeds.

14. The method of claim 13 wherein said feed comprises endogenous soybean seeds having an SDA concentration greater than about 5% and a GLA concentration less than about 20%.

15. The method of claim 14 wherein said feed comprises a soybean oil having an SDA concentration greater than about 10% SDA and less than about 20% GLA.

16. The method of claim 14 wherein said feed comprises a soybean oil having an SDA concentration greater than about 15% and a GLA concentration less than about 20%.

17. A feed product for an animal comprising
a. starting feed ingredients;
b. soybean oil; and,
wherein said soybean oil comprises SDA, ALA and GLA; and wherein the ratio of SDA/GLA is at least about 1.3 and the ratio of SDA/ALA is at least about 0.5.

18. The feed product of claim 17 wherein said ratio of SDA/GLA is at least about 1.5.

19. The feed product of claim 18 wherein said ratio of SDA/GLA is at least about 2.0.

20. The feed product of claim 19 wherein said ratio of SDA/GLA is at least about 2.5.

21. The feed product of claim 20 wherein said ratio of SDA/GLA is at least about 3.0.

22. The feed product of claim 17 wherein said ratio of SDA/ALA is at least about 1.0.

23. The feed product of claim 22 wherein said ratio of SDA/ALA is at least about 1.5.

24. The feed product of claim 17 wherein said ratio of SDA/ALA is less than about 1.8.

25. The feed product of claim 17 wherein said feed product is a livestock feed.

26. The feed product of claim 25 wherein said feed product is a feed selected from the group consisting of horse feed, beef cattle feed, dairy cattle feed, swine feed, poultry feed, sheep feed, goat feed, or fish feed.

27. The feed product of claim 17 wherein said feed product is a feed supplement.

28. The feed product of claim 17 wherein said feed product is an intermediate moisture food.

29. The feed product of claim 28 wherein said feed product is selected from the group consisting of dog food and cat food.

30. The feed product of claim 17 wherein said feed product further comprises an excipient.

31. A food or feed comprising soybean oil comprising ALA, SDA, and GLA, wherein the ratio of SDA/GLA in said soybean oil is at least about 1.3.

* * * * *

SEQUENCE LISTING

<160> NUMBER OF SEQ ID NOS: 60

<210> SEQ ID NO 1
<211> LENGTH: 1953
<212> TYPE: DNA
<213> ORGANISM: Primula juliae

<400> SEQUENCE: 1

```
tatatatata tatatatata atcccaaaca aacactgtca cttgcaaaac aaactcaacc      60
cacgttactt atccctttttc cccaaaatgg aaaacacatt ttcaccacca cctactaaca     120
ccaattccaa ccccatgact aagaccattt acataaccag ctcagaactt gaaaaacata     180
acaagccagg tgacctatgg atatcaattc acggtcaagt ttacgacgtt tcttcctggg     240
ctgcgcttca cccgggggc atcgctcccc tcctcgccct tgcaggacat gatgtgaccg     300
acgctttcct cgcttaccat cccccctycca cctcccgcct cctccctccc ttctccacca     360
acctacttct agaaaaacat tccgtgtccg agacctcttc cgactatcgc aaacttctag     420
acagctttca taagatgggc atgtttcgtg ccaggggcca cactgcctac gcgaccttttg     480
```

```
tcattatgat acttatgttg gtttcctctg tgactggggt gctttgcagt gagaatccgt      540
gggtgcattt ggtttgtgga gcggcaatgg ggtttgcctg gatccagtgc ggatggatag      600
gtcatgattc cggacattac cggataatga ctgacaggaa atggaaccgg ttcgctcaga      660
tcctgagctc aaactgcctc aagggattag tatcgggtg gtggaagtgg aaccacaacg       720
cgcaccacat tgcctgcaat agtctggagt acgaccctga cctccagtac attcccttgt      780
tggttgtgtc cccgaagttc tttaactccc tcacttctcg tttctacgac aagaagctga      840
acttcgacgg tgtgtcgagg ttttggttc aataccagca ctggtcgttt tatccggtca       900
tgtgtgttgc taggctgaac atgcttgcgc agtcgtttat actgcttttt tcgaggaggg      960
aggtggcgaa cagggtgcag gagattcttg gactagcggt tttttggctt tggtttccgc     1020
tcctgctttc ttgccttcct aattggggtg agagaataat gttttgctc gcgagctact      1080 ccgttacggg gatacaacac gtgcagttca gcttgaacca tttctcatct gacgtttacg     1140
tgggcccacc cgtaggtaac gattggttta agaaacagac tgcagggaca ctcaacatat     1200
cgtgcccggc gtggatggat tggttccacg gtggattgca gtttcaggtc gagcaccact     1260
tgttcccgcg gatgcctagg ggtcagtttc ggaagatttc ccttttgtg agggatttgt      1320 gtaagaaaca caatttgact tacaatattg cgtcttttac taaagcaaat gtgttgacgc     1380
ttgagaccct gagaaacaca gccattgagg ctcgggacct ctctaatccg atcccaaaga     1440
atatggtgtg ggaggctgtt aaaaatgtcg ggtgaaattg actatgtgtt ttgctattgg     1500
agcttcaatt tcgtgattgt cgtttaaggg ggtatacaca atcaccagat aatcaaacgt     1560
tttctgttgt atttcgttct tgttatttac atttgtagag tggctcatgt aactgacttg     1620
tgtcgaatcg ttaagcctaa atacaagtgt aacaatttag tttctgtcca atttgagaaa     1680
tagaaaagtt tggttgagcc ttttttttct tctaatttct tcaacaggct tattgagtgc     1740
cttatttgcc acatacttaa gcgaaatgct ccaagtgcgc tagccgcaga tgtataaatt     1800 gtcttttcg gcttcaagtt ttaactgtat aacgtcattt cggcttatcg taatggttca      1860
aattagctgc ttttgttttg acaattgtcc taagcaggca ctgatcaaca ctatcagttg     1920
ttctttccct ggtaaaaaag aactgttgaa ttt                                  1953

<210> SEQ ID NO 2
<211> LENGTH: 1341
<212> TYPE: DNA
<213> ORGANISM: Primula juliae

<400> SEQUENCE: 2
atgactaaga ccatttacat aaccagctca gaacttgaaa aacataacaa gccaggtgac       60
ctatggatat caattcacgg tcaagtttac gacgtttctt cctgggctgc gcttcacccg      120 ggggcatcg ctcccctcct cgcccttgca ggacatgatg tgaccgacgc tttcctcgct       180
taccatcccc cttccacctc ccgcctcctc cctcccttct ccaccaacct acttctagaa      240
aaacattccg tgtccgagac ctcttccggc tatcgcaaac ttctagacag ctttcataag      300
atgggcatgt ttcgtgccag gggccacact gcctacgcga cctttgtcat tatgatactt      360
atgttggttt cctctgtgac tggggtgctt tgcagtgaga atccgtgggt gcatttggtt      420
tgtggagcgg caatgggggtt tgcctggatc cagtgcggat ggataggtca tgattccgga    480
cattaccgga taatgactga caggaaatgg aaccggttcg ctcagatcct gagctcaaac     540
tgcctccaag ggattagcat cgggtggtgg aagtggaacc acaacgcgca ccacattgcc     600
tgcaatagtc tggagtacga ccctgacctc cagtacattc ccttgttggt tgtgtccccg     660
```

```
aagttcttta actccctcac ttctcgtttc tacgacaaga agctgaactt cgacggtgtg    720
tcgaggtttt tggttcaata ccagcactgg tcgttttatc cggtcatgtg tgttgctagg    780
ctgaacatgc ttgcgcagtc gtttatactg ctttttttcga ggaggaggt ggcgaacagg    840 gtgcaggaga ttcttggact agcggttttt tggctttggt ttccgctcct gctttcttgc    900
cttcctaatt ggggtgagag aataatgttt ttgctcgcga gctactccgt tacggggata    960
caacacgtgc agttcagctt gaaccatttc tcatctgacg tttacgtggg cccacccgta   1020
ggtaacgatt ggtttaagaa acagactgca gggacactca acatatcgtg cccggcgtgg   1080
atggattggt tccatggcgg gttgcagttt caggtcgagc accacttgtt cccgcggatg   1140
cctaggggtc agtttcggaa gatttctcct tttgtgaggg atttgtgtaa gaaacacaat   1200
ttgacttaca atattgcgtc ttttactaaa gcaaatgtgt tgacgcttga ccctgaga    1260 aacacagcca ttgaggctcg ggacctctct aatccgatcc caaagaatat ggtgtgggag   1320
gctgttaaaa atgtcgggtg a                                             1341

<210> SEQ ID NO 3
<211> LENGTH: 1389
<212> TYPE: DNA
<213> ORGANISM: Primula juliae

<400> SEQUENCE: 3
atggaaaaca cattttcacc accacctact aacaccaatt ccaacccat gactaagacc      60 atttacataa ccagctcaga acttgaaaaa cataacaagc caggtgacct atggatatca    120
attcacggtc aagtttacga cgtttcttcc tgggctgcgc ttcacccggg gggcatcgct    180
cccctcctcg cccttgcagg acatgatgtg accgacgctt cctcgctta ccatccccct     240 tccacctccc gcctcctccc tcccttctcc accaacctac ttctagaaaa acattccgtg    300
tccgagacct cttccgacta tcgcaaactt ctagacagct tcataagat gggcatgttt     360 cgtgccagag gccacactgc ctacgcgacc tttgtcatta tgatacttat gttggtttcc    420
tctgtgactg gggtgctttg cagtgagaat ccgtgggtgc atttggtttg tggagcggca    480
atggggtttg cctggatcca gtgcggatgg ataggtcatg attccggaca ttaccggata    540
atgactgaca ggaaatggaa ccggttcgct cagatcctga gctcaaactg cctccaaggg    600
attagcatcg ggtggtggaa gtggaaccac aacgcgcacc acattgcctg caatagtctg    660
gagtacgacc ctgacctcca gtacattccc ttgttggttg tgtccccgaa gttctttaac    720
tccctcactt ctcgtttcta cgacaagaag ctgaacttcg acggtgtgtc gaggtttttg    780
gttcaatacc agcactggtc gttttatccg gtcatgtgtg ttgctaggct gaacatgctt    840
gcgcagtcgt ttatactgct tttttcgagg agggaggtgg cgaacagggt gcaggagatt    900
cttggactag cggttttttg gctttggttt ccgctcctgc tttcttgcct tcctaattgg    960
ggtgagagaa taatgttttt gctcgcgagc tactccgtta cggggataca acacgtgcag   1020
ttcagcttga accatttctc atctgacgtt tacgtgggcc cacccgtagg taacgattgg   1080
tttaagaaac agactgcagg gacactcaac atatcgtgcc cggcgtggat ggattggttc   1140
catggcgggt tgcagtttca ggtcgagcac cacttgttcc cgcggatgcc tagggtcag   1200 tttcggaaga tttctccttt tgtgagggat tgtgtaaga acacaatttt gacttacaat   1260
attgcgtctt ttactaaagc aaatgtgttg acgcttgaga ccctgagaaa cacagccatt   1320
gaggctcggg acctctctaa tccgatccca aagaatatgg tgtgggaggc tgttaaaaat   1380
gtcgggtga                                                           1389
```

<210> SEQ ID NO 4
<211> LENGTH: 446
<212> TYPE: PRT
<213> ORGANISM: Primula juliae

<400> SEQUENCE: 4

```
Met Thr Lys Thr Ile Tyr Ile Thr Ser Ser Glu Leu Glu Lys His Asn
1               5                   10                  15

Lys Pro Gly Asp Leu Trp Ile Ser Ile His Gly Gln Val Tyr Asp Val
            20                  25                  30

Ser Ser Trp Ala Ala Leu His Pro Gly Gly Ile Ala Pro Leu Leu Ala
        35                  40                  45

Leu Ala Gly His Asp Val Thr Asp Ala Phe Leu Ala Tyr His Pro Pro
    50                  55                  60

Ser Thr Ser Arg Leu Leu Pro Pro Phe Ser Thr Asn Leu Leu Leu Glu
65                  70                  75                  80

Lys His Ser Val Ser Glu Thr Ser Ser Asp Tyr Arg Lys Leu Leu Asp
                85                  90                  95

Ser Phe His Lys Met Gly Met Phe Arg Ala Arg Gly His Thr Ala Tyr
            100                 105                 110

Ala Thr Phe Val Ile Met Ile Leu Met Leu Val Ser Val Thr Gly
        115                 120                 125

Val Leu Cys Ser Glu Asn Pro Trp Val His Leu Val Cys Gly Ala Ala
    130                 135                 140

Met Gly Phe Ala Trp Ile Gln Cys Gly Trp Ile Gly His Asp Ser Gly
145                 150                 155                 160

His Tyr Arg Ile Met Thr Asp Arg Lys Trp Asn Arg Phe Ala Gln Ile
                165                 170                 175

Leu Ser Ser Asn Cys Leu Gln Gly Ile Ser Ile Gly Trp Trp Lys Trp
            180                 185                 190

Asn His Asn Ala His His Ile Ala Cys Asn Ser Leu Glu Tyr Asp Pro
        195                 200                 205

Asp Leu Gln Tyr Ile Pro Leu Leu Val Val Ser Pro Lys Phe Phe Asn
    210                 215                 220

Ser Leu Thr Ser Arg Phe Tyr Asp Lys Lys Leu Asn Phe Asp Gly Val
225                 230                 235                 240

Ser Arg Phe Leu Val Gln Tyr Gln His Trp Ser Phe Tyr Pro Val Met
                245                 250                 255

Cys Val Ala Arg Leu Asn Met Leu Ala Gln Ser Phe Ile Leu Leu Phe
            260                 265                 270

Ser Arg Arg Glu Val Ala Asn Arg Val Gln Glu Ile Leu Gly Leu Ala
        275                 280                 285

Val Phe Trp Leu Trp Phe Pro Leu Leu Leu Ser Cys Leu Pro Asn Trp
    290                 295                 300

Gly Glu Arg Ile Met Phe Leu Leu Ala Ser Tyr Ser Val Thr Gly Ile
305                 310                 315                 320

Gln His Val Gln Phe Ser Leu Asn His Phe Ser Ser Asp Val Tyr Val
                325                 330                 335

Gly Pro Pro Val Gly Asn Asp Trp Phe Lys Lys Gln Thr Ala Gly Thr
            340                 345                 350

Leu Asn Ile Ser Cys Pro Ala Trp Met Asp Trp Phe His Gly Gly Leu
        355                 360                 365

Gln Phe Gln Val Glu His His Leu Phe Pro Arg Met Pro Arg Gly Gln
    370                 375                 380
```

```
Phe Arg Lys Ile Ser Pro Phe Val Arg Asp Leu Cys Lys Lys His Asn
385                 390                 395                 400

Leu Thr Tyr Asn Ile Ala Ser Phe Thr Lys Ala Asn Val Leu Thr Leu
            405                 410                 415

Glu Thr Leu Arg Asn Thr Ala Ile Glu Ala Arg Asp Leu Ser Asn Pro
        420                 425                 430

Ile Pro Lys Asn Met Val Trp Glu Ala Val Lys Asn Val Gly
        435                 440                 445

<210> SEQ ID NO 5
<211> LENGTH: 462
<212> TYPE: PRT
<213> ORGANISM: Primula juliae

<400> SEQUENCE: 5

Met Glu Asn Thr Phe Ser Pro Pro Thr Asn Thr Asn Ser Asn Pro
1               5                   10                  15

Met Thr Lys Thr Ile Tyr Ile Thr Ser Ser Glu Leu Glu Lys His Asn
                20                  25                  30

Lys Pro Gly Asp Leu Trp Ile Ser Ile His Gly Gln Val Tyr Asp Val
            35                  40                  45

Ser Ser Trp Ala Ala Leu His Pro Gly Gly Ile Ala Pro Leu Leu Ala
    50                  55                  60

Leu Ala Gly His Asp Val Thr Asp Ala Phe Leu Ala Tyr His Pro Pro
65                  70                  75                  80

Ser Thr Ser Arg Leu Leu Pro Pro Phe Ser Thr Asn Leu Leu Leu Glu
                85                  90                  95

Lys His Ser Val Ser Glu Thr Ser Ser Asp Tyr Arg Lys Leu Leu Asp
            100                 105                 110

Ser Phe His Lys Met Gly Met Phe Arg Ala Arg Gly His Thr Ala Tyr
        115                 120                 125

Ala Thr Phe Val Ile Met Ile Leu Met Leu Val Ser Ser Val Thr Gly
    130                 135                 140

Val Leu Cys Ser Glu Asn Pro Trp Val His Leu Val Cys Gly Ala Ala
145                 150                 155                 160

Met Gly Phe Ala Trp Ile Gln Cys Gly Trp Ile Gly His Asp Ser Gly
                165                 170                 175

His Tyr Arg Ile Met Thr Asp Arg Lys Trp Asn Arg Phe Ala Gln Ile
            180                 185                 190

Leu Ser Ser Asn Cys Leu Gln Gly Ile Ser Ile Gly Trp Trp Lys Trp
        195                 200                 205

Asn His Asn Ala His His Ile Ala Cys Asn Ser Leu Glu Tyr Asp Pro
    210                 215                 220

Asp Leu Gln Tyr Ile Pro Leu Leu Val Val Ser Pro Lys Phe Phe Asn
225                 230                 235                 240

Ser Leu Thr Ser Arg Phe Tyr Asp Lys Lys Leu Asn Phe Asp Gly Val
                245                 250                 255

Ser Arg Phe Leu Val Gln Tyr Gln His Trp Ser Phe Tyr Pro Val Met
            260                 265                 270

Cys Val Ala Arg Leu Asn Met Leu Ala Gln Ser Phe Ile Leu Leu Phe
        275                 280                 285

Ser Arg Arg Glu Val Ala Asn Arg Val Gln Glu Ile Leu Gly Leu Ala
    290                 295                 300

Val Phe Trp Leu Trp Phe Pro Leu Leu Leu Ser Cys Leu Pro Asn Trp
305                 310                 315                 320
```

```
Gly Glu Arg Ile Met Phe Leu Leu Ala Ser Tyr Ser Val Thr Gly Ile
            325                 330                 335

Gln His Val Gln Phe Ser Leu Asn His Phe Ser Ser Asp Val Tyr Val
        340                 345                 350

Gly Pro Pro Val Gly Asn Asp Trp Phe Lys Lys Gln Thr Ala Gly Thr
    355                 360                 365

Leu Asn Ile Ser Cys Pro Ala Trp Met Asp Trp Phe His Gly Gly Leu
370                 375                 380

Gln Phe Gln Val Glu His His Leu Phe Pro Arg Met Pro Arg Gly Gln
385                 390                 395                 400

Phe Arg Lys Ile Ser Pro Phe Val Arg Asp Leu Cys Lys Lys His Asn
            405                 410                 415

Leu Thr Tyr Asn Ile Ala Ser Phe Thr Lys Ala Asn Val Leu Thr Leu
        420                 425                 430

Glu Thr Leu Arg Asn Thr Ala Ile Glu Ala Arg Asp Leu Ser Asn Pro
    435                 440                 445

Ile Pro Lys Asn Met Val Trp Glu Ala Val Lys Asn Val Gly
450                 455                 460

<210> SEQ ID NO 6
<211> LENGTH: 24
<212> TYPE: DNA
<213> ORGANISM: Artificial
<220> FEATURE:
<223> OTHER INFORMATION: Primer

<400> SEQUENCE: 6
atmagyatyg gttggtggaa rtgg                                           24

<210> SEQ ID NO 7
<211> LENGTH: 23
<212> TYPE: DNA
<213> ORGANISM: Artificial
<220> FEATURE:
<223> OTHER INFORMATION: Primer

<400> SEQUENCE: 7
aatccaccrt graaccartc cat                                            23

<210> SEQ ID NO 8
<211> LENGTH: 27
<212> TYPE: DNA
<213> ORGANISM: Artificial
<220> FEATURE:
<223> OTHER INFORMATION: Primer

<400> SEQUENCE: 8
cacacatgac cggataaaac gaccagt                                        27

<210> SEQ ID NO 9
<211> LENGTH: 27
<212> TYPE: DNA
<213> ORGANISM: Artificial
<220> FEATURE:
<223> OTHER INFORMATION: Primer

<400> SEQUENCE: 9
gggaatgtac tggaggtcag ggtcgta                                        27

<210> SEQ ID NO 10
<211> LENGTH: 27
<212> TYPE: DNA
```

<210> SEQ ID NO 10
<211> LENGTH: 27
<212> TYPE: DNA
<213> ORGANISM: Artificial
<220> FEATURE:
<223> OTHER INFORMATION: Primer

<400> SEQUENCE: 10
cgtgcagttc agcttgaacc atttctc                                       27

<210> SEQ ID NO 11
<211> LENGTH: 27
<212> TYPE: DNA
<213> ORGANISM: Artificial
<220> FEATURE:
<223> OTHER INFORMATION: Primer

<400> SEQUENCE: 11
tgcagggaca ctcaacatat cgtgccc                                       27

<210> SEQ ID NO 12
<211> LENGTH: 27
<212> TYPE: DNA
<213> ORGANISM: Artificial
<220> FEATURE:
<223> OTHER INFORMATION: Primer

<400> SEQUENCE: 12
gtaggttggt ggagaaggga gggagga                                       27

<210> SEQ ID NO 13
<211> LENGTH: 27
<212> TYPE: DNA
<213> ORGANISM: Artificial
<220> FEATURE:
<223> OTHER INFORMATION: Primer

<400> SEQUENCE: 13
ggaaggggga tggtaagcga ggaaagc                                       27

<210> SEQ ID NO 14
<211> LENGTH: 33
<212> TYPE: DNA
<213> ORGANISM: Artificial
<220> FEATURE:
<223> OTHER INFORMATION: Primer

<400> SEQUENCE: 14
gtcgacatgg aaaacacatt ttcaccacca cct                                33

<210> SEQ ID NO 15
<211> LENGTH: 33
<212> TYPE: DNA
<213> ORGANISM: Artificial
<220> FEATURE:
<223> OTHER INFORMATION: Primer

<400> SEQUENCE: 15
gtcgacatga ctaagaccat ttacataacc agc                                33

<210> SEQ ID NO 16
<211> LENGTH: 34
<212> TYPE: DNA
<213> ORGANISM: Artificial
<220> FEATURE:
<223> OTHER INFORMATION: Primer

<400> SEQUENCE: 16
cctgcaggtc acccgacatt tttaacagcc tccc                               34

<210> SEQ ID NO 17
<211> LENGTH: 1290
<212> TYPE: DNA
<213> ORGANISM: Neurospora crassa

<400> SEQUENCE: 17

| | | |
|---|---|---|
| atggctgtca ctactaggtc acacaaagcc gccgctgcca ccgaacctga agttgtgtct | 60 |
| acaggagtgg atgcagtcag cgctgccgca ccaagcagta gtagctcctc atcctcccaa | 120 |
| aagtcagctg agcctatcga atatccagac atcaagacaa ttcgtgacgc tataccagac | 180 |
| cactgcttta gacctcgcgt ttggatatcc atggcgtact ttattcgcga tttttgcaatg | 240 |
| gctttcggcc tcggatactt ggcatggcaa tacatccctt tgattgcaag taccccattg | 300 |
| agatacggag cttgggcttt gtacggttac ctccagggac tcgtctgtac tggaatttgg | 360 |
| atcttggctc acgaatgcgg tcacggagcc ttttctagac acacctggtt caacaacgtt | 420 |
| atgggttgga ttggtcactc tttcctacta gtcccatatt ttagctggaa attttcccat | 480 |
| caccgtcatc ataggttcac cggacatatg gaaaaagata tggcgttcgt tccagccacg | 540 |
| gaggcggaca gaaatcagag aaaactagct aatctctata tggacaaaga gactgcggag | 600 |
| atgttcgagg atgttcctat tgtgcagttg gttaaactaa ttgctcacca actcgccggt | 660 |
| tggcagatgt atctcttgtt caacgttagt gccggaaaag ctccaaaaca gtgggaaacc | 720 |
| ggcaaaggtg gaatgggatg gctccgcgtg agccatttcg aaccaagttc agccgttttc | 780 |
| agaaacagcg aagcaattta catagctcta agcgatctcg gacttatgat tatgggatac | 840 |
| attctctacc aggcagccca agttgttgga tgcaaatgg ttggtctctt gtattttcaa | 900 |
| cagtacttct gggttcacca ttggctcgtt gccatcactt accttcatca cacacacgaa | 960 |
| gaagttcacc actttgatgc agattcttgg acatttgtta agggtgccct cgctaccgtg | 1020 |
| gacagagact tcggtttcat cggcaagcac ctcttccata acatcattga ccatcatgtt | 1080 |
| gttcatcacc tcttcccaag aatccctttc tactacgctg aagaagctac caattcaata | 1140 |
| agacctatgc tcggacctct ttaccacaga gatgaccgtt ctttcatggg gcaactctgg | 1200 |
| tacaacttca cacactgcaa atgggttgtc cctgatcctc aagtgccagg tgctctaatc | 1260 |
| tgggctcaca ccgttcagag tactcagtaa | 1290 |

<210> SEQ ID NO 18
<211> LENGTH: 1209
<212> TYPE: DNA
<213> ORGANISM: Aspergillus nidulans

<400> SEQUENCE: 18

| | | |
|---|---|---|
| atggccgcaa ccgcgaccac tctcgctgaa atagaaaaga agaaggaaga gattacacta | 60 |
| cagacaatca agaatgccat accaaagcac tgttttaacc gtagtttgct tatttcaagt | 120 |
| gcctacgtcg tcagagacct cctctacgca tcagttttgt tctattttgc acttcatatt | 180 |
| gatacgctct tctcatccca gctccttagg atcttggcat ggacagctta cggtttcatg | 240 |
| caaggctgcg tggaacgggt atatggata ttggcacatg aatgcggaca cggagctttt | 300 |
| agcccttacc aaacctggaa cgacgttgtt gggtggaccc ttcattctct tctcatggtc | 360 |
| ccttacttct cttggaaaat aacccacgca aggcaccaca gatatacgaa caataccgag | 420 |
| agggacacag ccttcgttcc ctggaccgag aaggaatacg acaccagacc tcgttacttc | 480 |
| cctgcatggt tcgagatgtt tgaagacaca ccagtgtata acttgatttc attgctcgcc | 540 |
| catcagatcg ccggctggca aatgtacctc tgcttctacg tctcagccgg agccaaaagt | 600 |

| | |
|---|---|
| aagcctgttc cacaaggcaa gcagtccgga tggtttggag gtcaacaatc tgcatcacac | 660 |
| tttgacccag gaagctctct atggaccgaa aaccagcgcc atctaatcgc aatctccgac | 720 |
| cttggactcc ttctcgtggc cgccgcgaat tggtacttgg ctcaacaagt tggtgttcta | 780 |
| agaatggtgc tcatttacgt cgtcccctac ttttgggtcc accactggct agtcgccatc | 840 |
| acgtacctcc accacactca cccatccata ccacactaca ccgactctac ctggacattc | 900 |
| actaaaggag cactctcaac agtggatcgt gacttcggat ttataggaag cacttctttt | 960 |
| caccacatca ttgatcacca cgtcgttcat cacttgttca ataggatacc attctatcac | 1020 |
| gcagaggaag ctactaacgc aataatacca gttctcggtg atatgtacca tagagaagaa | 1080 |
| accggattcc tctggagtct tatggaaact tataaaaact gtcgctttgt tggcgtggag | 1140 |
| aacgatgtgg gtaaggaggg agttctccat tgggttttcg aagaaaagaa aggcgctaaa | 1200 |
| gctgaatag | 1209 |

<210> SEQ ID NO 19
<211> LENGTH: 1290
<212> TYPE: DNA
<213> ORGANISM: Neurospora crassa

<400> SEQUENCE: 19

| | |
|---|---|
| atgacggtca ccacccgcag ccacaaggcc gcggccgcca ccgagcccga ggttgtcagc | 60 |
| accggcgttg acgccgtctc tgctgctgct ccctcctcct cctcctcctc ttccagccaa | 120 |
| aagtcggccg agcccatcga ataccccgac atcaagacca tccgcgacgc catccccgac | 180 |
| cactgcttcc gcccgcgcgt ctggatctcc atggcctact tcatccgcga cttcgccatg | 240 |
| gcctttggcc tcggctacct cgcctggcag tacatccccc tgatcgcctc caccccgctc | 300 |
| cgctacggcg cctgggctct gtacggctac ctccagggtc tcgtctgcac gggcatctgg | 360 |
| attctggcgc acgagtgcgg ccacggcgcc ttctcgaggc acacgtggtt caacaacgtc | 420 |
| atggggtgga ttggccactc cttcctcttg gtcccttact tcagctggaa gttcagccac | 480 |
| catcgccacc atcgcttcac cggccacatg gagaaggaca tggcgtttgt gcctgccacc | 540 |
| gaggctgatc gcaaccagag gaagctggcc aacttgtaca tggacaagga gacggccgag | 600 |
| atgtttgagg atgtgcccat tgtccagctc gtcaagctca tcgcccacca gctggccggc | 660 |
| tggcagatgt acctcctctt caacgtctcc gccggtaagg gcagcaagca gtgggagact | 720 |
| ggcaagggcg gcatgggctg gttgagggtt agccactttg agccttcctc tgctgtgttc | 780 |
| cgcaactccg aggccatcta cattgccctg tccgatcttg gtctcatgat catgggctat | 840 |
| atcctctacc aggccgcgca ggttgttggc tggcagatgg taggtctgct gtacttccag | 900 |
| cagtacttct gggttcacca ttggttggtc gccatcactt acctccacca cacccacgag | 960 |
| gaagtccacc actttgacgc cgactcgtgg accttcgtca agggcgctct cgccaccgtc | 1020 |
| gaccgcgatt ttggcttcat tggcaagcac ctcttccaca acattatcga ccaccacgtc | 1080 |
| gtccaccact tgttccctcg catccccttc tactacgccg aagaagccac caactcgatc | 1140 |
| cgccccatgc tcggccccct ctaccaccgc gacgaccgct ccttcatggg ccagctgtgg | 1200 |
| tacaacttca cccactgcaa gtgggtcgtt ccggaccccc aggtccccgg cgcgcttatt | 1260 |
| tgggcgcaca ccgttcagag cacccagtaa | 1290 |

<210> SEQ ID NO 20
<211> LENGTH: 1290
<212> TYPE: DNA
<213> ORGANISM: Neurospora crassa

<400> SEQUENCE: 20

```
atggcggtca ccaccgcag ccacaaggcc gcggccgcca ccgagcccga ggttgtcagc      60
accggcgttg acgccgtctc tgctgctgct ccctcctcct cctcctcctc ttccagccaa    120
aagtcggccg agcccatcga ataccccgac atcaagacca ccgcgacgc catcccgac     180
cactgcttcc gcccgcgcgt ctggatctcc atggcctact tcatccgcga cttcgccatg    240
gcctttggcc tcggctacct cgcctggcag tacatccccc tgatcgcctc caccccgctc    300
cgctacggcg cctgggctct gtacggctac ctccagggtc tcgtctgcac gggcatctgg    360
attctggcgc acgagtgcgg ccacggcgcc ttctcgaggc acacgtggtt caacaacgtc    420
atggggtgga ttggccactc cttcctcttg gtcccttact tcagctggaa gttcagccac    480
catcgccacc atcgcttcac cggccacatg gagaaggaca tggcgtttgt gcctgccacc    540
gaggctgatc gcaaccagag gaagctggcc aacttgtaca tggacaagga cggccgag     600
atgtttgagg atgtgcccat tgtccagctc gtcaagctca tcgcccacca gctgccggc    660
tggcagatgt acctcctctt caacgtctcc gccggtaagg gcagcaagca gtgggagact    720
ggcaagggcg gcatgggctg gttgagggtt agccactttg agccttcctc tgctgtgttc    780
cgcaactccg aggccatcta cattgccctg tccgatcttg gtctcatgat catgggctac    840
atcctctacc aggccgcgca ggttgttggc tggcagatgg tgggtctgct gtacttccag    900
cagtacttct gggttcacca ttggttggtc gccatcactt acctccacca cacccacgag    960
gaagtccacc actttgacgc cgactcgtgg accttcgtca agggcgctct cgccaccgtc   1020
gaccgcgatt ttggcttcat tggcaagcac ctcttccaca acattatcga ccaccacgtc   1080
gtccaccact tgttccctcg catccccttc tactacgccg aagaagccac caactcgatc   1140
cgccccatgc tcggcccct ctaccaccgc gacgaccgct ccttcatggg ccagctgtgg   1200
tacaacttca cccactgcaa gtgggtcgtt ccggaccccc aggtccccgg cgcgcttatt   1260
tgggcgcaca ccgttcagag cacccagtaa                                    1290
```

<210> SEQ ID NO 21
<211> LENGTH: 1341
<212> TYPE: DNA
<213> ORGANISM: Primula alpicola

<400> SEQUENCE: 21

```
atggccaaca ctagttacat ttccagctca gacctcaaaa ctcataataa ggctgacgac     60
ctttggatat ccattcacgg ccaagtgtac gatgtctccg cctgggccac ccaccacccc   120
ggaggtgcct ctctcctcct cgccttgca ggcaatgatg tcactgatgc cttcctcgcc    180
taccaccctc cctccacctg ccacctcctc cctcctcttt ctaccaacat cctcctcgaa    240
aactactccg tctcccacat ctcctccaat taccgcaacc tcctcaatca tttccacaag    300
ctcggcctat tccgtaccag ggcccacacc gctttcacta cattcttcat catgatactt    360
atgttctta ttagtgtaac cggaatattt tgcagtgata gtttatgggt ccatttggcg    420
tgcggtggct tgatggggtt tgcatggatt caatgcggat ggatagcgca cgactctggg    480
cattaccgga taacatcaag taggaaatgg aatagattcg ctcagatcct taccggaaat    540
tgcctccagg ggttgagtat tgggtggtgg aagtggaacc ataacgccca ccacatcgct    600
tgcaatagcc tagactacga tccggacctc cagtatattc ctttattggt cgtgtccccg    660
aagttttca actccatcac ttctcgtttt tatgataaga agctgaactt cgatggtgtg    720
tcgaggtttt tagtcagcta ccaacactgg acgttttatc cggtcatgtg tgttgctagg    780
```

```
tttaacatga ttgcacagtc ggttatacat ctcttctcga atagaaacgt gactgatagg    840
gtcctagaga ttttcggact aggggtgttc tgggtttggt attcgctcct actttcgtgc    900
cttcctgatt ggggtgagcg aataatgttt gtgattgcgt gctatttcgt tactgggata    960
caacacgtac agttcagtgt aaaccatttt tcttcggacg tatacatggg ccctccagta   1020
ggtaacgatt ggtttaaaaa acagacttcg gggacactga acatatcgtg cccacccctgg  1080 atggattggt tccacggtgg gttgcagttt caagtggagc accacttgtt cccgcggatg   1140
ccgaggggtc aattcaggaa gatctctcct tttgtaaagg atctgtgtaa taaacacaat   1200
ctgccttaca atatcgcgtc ttttaccatg gcaaacgtgt tgacgcttag gaccctaaga   1260
aatacggcca tcgaggctcg ggacctttct aatccgattc caagaatat ggtctgggaa    1320 gctgttaaca ctctggggtg a                                             1341
```

<210> SEQ ID NO 22
<211> LENGTH: 446
<212> TYPE: PRT
<213> ORGANISM: Primula alpicola

<400> SEQUENCE: 22

```
Met Ala Asn Thr Ser Tyr Ile Ser Ser Ser Asp Leu Lys Thr His Asn
1               5                   10                  15

Lys Ala Asp Asp Leu Trp Ile Ser Ile His Gly Gln Val Tyr Asp Val
            20                  25                  30

Ser Ala Trp Ala Thr His His Pro Gly Gly Ala Ser Leu Leu Leu Ala
        35                  40                  45

Leu Ala Gly Asn Asp Val Thr Asp Ala Phe Leu Ala Tyr His Pro Pro
    50                  55                  60

Ser Thr Cys His Leu Leu Pro Pro Leu Ser Thr Asn Ile Leu Leu Glu
65                  70                  75                  80

Asn Tyr Ser Val Ser His Ile Ser Ser Asn Tyr Arg Asn Leu Leu Asn
                85                  90                  95

His Phe His Lys Leu Gly Leu Phe Arg Thr Arg Ala His Thr Ala Phe
            100                 105                 110

Thr Thr Phe Phe Ile Met Ile Leu Met Phe Phe Ile Ser Val Thr Gly
        115                 120                 125

Ile Phe Cys Ser Asp Ser Leu Trp Val His Leu Ala Cys Gly Gly Leu
    130                 135                 140

Met Gly Phe Ala Trp Ile Gln Cys Gly Trp Ile Ala His Asp Ser Gly
145                 150                 155                 160

His Tyr Arg Ile Thr Ser Ser Arg Lys Trp Asn Arg Phe Ala Gln Ile
                165                 170                 175

Leu Thr Gly Asn Cys Leu Gln Gly Leu Ser Ile Gly Trp Trp Lys Trp
            180                 185                 190

Asn His Asn Ala His His Ile Ala Cys Asn Ser Leu Asp Tyr Asp Pro
        195                 200                 205

Asp Leu Gln Tyr Ile Pro Leu Leu Val Val Ser Pro Lys Phe Phe Asn
    210                 215                 220

Ser Ile Thr Ser Arg Phe Tyr Asp Lys Lys Leu Asn Phe Asp Gly Val
225                 230                 235                 240

Ser Arg Phe Leu Val Ser Tyr Gln His Trp Thr Phe Tyr Pro Val Met
                245                 250                 255

Cys Val Ala Arg Phe Asn Met Ile Ala Gln Ser Val Ile His Leu Phe
            260                 265                 270

Ser Asn Arg Asn Val Thr Asp Arg Val Leu Glu Ile Phe Gly Leu Gly
```

```
                275                 280                 285
Val Phe Trp Val Trp Tyr Ser Leu Leu Leu Ser Cys Leu Pro Asp Trp
        290                 295                 300

Gly Glu Arg Ile Met Phe Val Ile Ala Cys Tyr Phe Val Thr Gly Ile
305                 310                 315                 320

Gln His Val Gln Phe Ser Val Asn His Phe Ser Ser Asp Val Tyr Met
                325                 330                 335

Gly Pro Pro Val Gly Asn Asp Trp Phe Lys Lys Gln Thr Ser Gly Thr
            340                 345                 350

Leu Asn Ile Ser Cys Pro Pro Trp Met Asp Trp Phe His Gly Gly Leu
        355                 360                 365

Gln Phe Gln Val Glu His His Leu Phe Pro Arg Met Pro Arg Gly Gln
    370                 375                 380

Phe Arg Lys Ile Ser Pro Phe Val Lys Asp Leu Cys Asn Lys His Asn
385                 390                 395                 400

Leu Pro Tyr Asn Ile Ala Ser Phe Thr Met Ala Asn Val Leu Thr Leu
                405                 410                 415

Arg Thr Leu Arg Asn Thr Ala Ile Glu Ala Arg Asp Leu Ser Asn Pro
            420                 425                 430

Ile Pro Lys Asn Met Val Trp Glu Ala Val Asn Thr Leu Gly
        435                 440                 445

<210> SEQ ID NO 23
<211> LENGTH: 1551
<212> TYPE: DNA
<213> ORGANISM: Primula alpicola

<400> SEQUENCE: 23
atggctaaca aatctcaaac aggttacata accagctcag acctgaaagg tcacaataag      60
gcaggtgatc tatggatatc aatccacggg caggtctacg acgtgtcctc gtgggccagc    120
cttcacccgg ggggcagtgc cccctcctg  gccctcgcag acacgacgt  gaccgacgct    180 ttcctcgctt accatccccc ttccaccgcc cgcctcctcc ctcccctctc cgctaacctc    240
cttctgcaac accattccgt ctcccccacc tcctccgatt accgctccct cctcaacaac    300
tttcataaac ttggtctgtt ccgcgccagg ggccacaccg cttacgcaac cttcgtcttc    360
atgatagcga tgtttgtaat gagcgtaacc ggagtgcttt ttagcgacga tgcgtggatc    420
catctggctt gcgccggagc aatggggatt gcctggatcc agtgcggatg gataggtcgg    480
tagactaatt tattagtaca tatttaatat ttaaaatacc atattcttaa atcttattta    540
aattttggta tgtatcaata tagcttaaaa caaaagtaa  aaataagtag aatgtatact    600
taaaatagat attaactatg agttttgat  aattaagatt caaattatgt actaaatgat    660
catttttcct ggataggtca cgactctggg cattaccgga tgatgtctga caggaaatgg    720
aaccggtttg cgcaaatcct gagcgcaaac tgcctccagg ggattagcat cgggtggtgg    780
aagtggaacc acaacgcaca ccacatcgct tgcaatagcc tggagtacga ccccgacctc    840
cagtatatcc ctttgctcgt tgtctccccc aagttttca  actcccttac ttctcgtttc    900
tacaacaaga aactgaactt cgacggtgtg gcgaggttct tggtttgcta ccagcactgg    960
acgttttatc cggtcatgtg tgtcgctagg ctgaacatga tcgtgcagtc gtttataacg   1020
ctttttttga ataggaggt  ggcgcatagg gcgcaagaga ttttgggact tgctgtgttt   1080 tgggttttggt ttccgctttt actttcttgc ttacctaatt ggggtgagag gataatgttt   1140
ctgcttgtga gctattccgt tacggggata caacacgtgc agttcagctt gaaccatttt   1200
```

```
tcttcggacg tctacgtggg tccgccagta ggtaacgact ggttcaagaa acagactgca    1260
gggacactta acatatcgtg cccagcgtgg atggattggt tccatggtgg gttgcaattt    1320
caggtcgagc accacttgtt cccgcggatg cctaggagtc agtttaggaa gatttctcct    1380
tttgtgaggg atttgtgtaa gaaacacaat ttgccttaca acatcgcgtc ttttactaaa    1440
gcgaatgtgt taacgcttaa gacgctgaga aatacggccg ttgaggctcg ggacctctct    1500
aatccgatcc caaagaatat ggtgtgggag gctgttaaaa ctctcgggtg a             1551
```

<210> SEQ ID NO 24
<211> LENGTH: 449
<212> TYPE: PRT
<213> ORGANISM: Primula alpicola

<400> SEQUENCE: 24

```
Met Ala Asn Lys Ser Gln Thr Gly Tyr Ile Thr Ser Ser Asp Leu Lys
1               5                   10                  15

Gly His Asn Lys Ala Gly Asp Leu Trp Ile Ser Ile His Gly Gln Val
            20                  25                  30

Tyr Asp Val Ser Ser Trp Ala Ser Leu His Pro Gly Gly Ser Ala Pro
        35                  40                  45

Leu Leu Ala Leu Ala Gly His Asp Val Thr Asp Ala Phe Leu Ala Tyr
    50                  55                  60

His Pro Pro Ser Thr Ala Arg Leu Leu Pro Pro Leu Ser Ala Asn Leu
65                  70                  75                  80

Leu Leu Gln His His Ser Val Ser Pro Thr Ser Ser Asp Tyr Arg Ser
                85                  90                  95

Leu Leu Asn Asn Phe His Lys Leu Gly Leu Phe Arg Ala Arg Gly His
            100                 105                 110

Thr Ala Tyr Ala Thr Phe Val Phe Met Ile Ala Met Phe Val Met Ser
        115                 120                 125

Val Thr Gly Val Leu Phe Ser Asp Asp Ala Trp Ile His Leu Ala Cys
    130                 135                 140

Ala Gly Ala Met Gly Ile Ala Trp Ile Gln Cys Gly Trp Ile Gly His
145                 150                 155                 160

Asp Ser Gly His Tyr Arg Met Met Ser Asp Arg Lys Trp Asn Arg Phe
                165                 170                 175

Ala Gln Ile Leu Ser Ala Asn Cys Leu Gln Gly Ile Ser Ile Gly Trp
            180                 185                 190

Trp Lys Trp Asn His Asn Ala His His Ile Ala Cys Asn Ser Leu Glu
        195                 200                 205

Tyr Asp Pro Asp Leu Gln Tyr Ile Pro Leu Leu Val Val Ser Pro Lys
    210                 215                 220

Phe Phe Asn Ser Leu Thr Ser Arg Phe Tyr Asn Lys Lys Leu Asn Phe
225                 230                 235                 240

Asp Gly Val Ala Arg Phe Leu Val Cys Tyr Gln His Trp Thr Phe Tyr
                245                 250                 255

Pro Val Met Cys Val Ala Arg Leu Asn Met Ile Val Gln Ser Phe Ile
            260                 265                 270

Thr Leu Phe Leu Asn Arg Glu Val Ala His Arg Ala Gln Glu Ile Leu
        275                 280                 285

Gly Leu Ala Val Phe Trp Val Trp Phe Pro Leu Leu Leu Ser Cys Leu
    290                 295                 300

Pro Asn Trp Gly Glu Arg Ile Met Phe Leu Leu Val Ser Tyr Ser Val
305                 310                 315                 320
```

```
            Thr Gly Ile Gln His Val Gln Phe Ser Leu Asn His Phe Ser Ser Asp
                        325                 330                 335
            Val Tyr Val Gly Pro Pro Val Gly Asn Asp Trp Phe Lys Lys Gln Thr
                        340                 345                 350
            Ala Gly Thr Leu Asn Ile Ser Cys Pro Ala Trp Met Asp Trp Phe His
                        355                 360                 365
            Gly Gly Leu Gln Phe Gln Val Glu His His Leu Phe Pro Arg Met Pro
                        370                 375                 380
            Arg Ser Gln Phe Arg Lys Ile Ser Pro Phe Val Arg Asp Leu Cys Lys
            385                 390                 395                 400
            Lys His Asn Leu Pro Tyr Asn Ile Ala Ser Phe Thr Lys Ala Asn Val
                                405                 410                 415
            Leu Thr Leu Lys Thr Leu Arg Asn Thr Ala Val Glu Ala Arg Asp Leu
                        420                 425                 430
            Ser Asn Pro Ile Pro Lys Asn Met Val Trp Glu Ala Val Lys Thr Leu
                        435                 440                 445
            Gly

<210> SEQ ID NO 25
<211> LENGTH: 1526
<212> TYPE: DNA
<213> ORGANISM: Primula waltonii

<400> SEQUENCE: 25
atggctaaca aatctcaaac aggttacata accagctcag acctgaaaag ccacaataag    60
gcaggtgatc tatggatatc aatccacggg caggtctacg acgtgtcctc gtgggccagt   120
cttcacccgg gggctctgc cccccttctg ccctcgcag acacgacgt taccgacgct   180 ttcctcgctt accatcctcc ttccaccgcc cgcctcctcc ctccctctc cgctaacctc    240 cttctacaac accactccgt ctcccccaca tcctccgatt accgatccct cctcaacaac    300
tttcacaaac ttggcctgtt ccgctccagg ggccacaccg cttacgccac cttcgtcttc    360
atgataacga tgtttgtaat gagcgtaacc ggagtgctct tcagcgacga tgcgtgggtc    420
catctggctt gcggcggagc aatggggatt gcctggatcc agtgcggatg gataggtcgg    480
tagagtaatt tattagtaca tatttaaaat accatattct taaatcttat ttaaattttg    540
gtatgtatca atcttttat gtactaatat atacttaaaa tagatattaa ctatgagttt    600
ttgataatta agtttcaaat tatgtactaa atgatcaatt ttcctggata ggtcacgact    660
ctgggcatta ccgatgatg tctgacagga aatggaaccg gttcgcgcaa atcctgagcg    720
caaactgcct ccaggggatt agcatcgggt ggtggaagtg gaaccacaac gcgcaccaca    780
tcgcttgcaa tagcctggaa tacgaccccg acctccagta tatccctttg ctcgtcgtct    840
cccccaaatt tttcaactcc cttacttctc gtttctacaa caagaaactg aacttcgacg    900
gtgtgtcgag gttcttggtt tgctaccagc actggacgtt ttatccggtc atgtgtgtcg    960
ctaggctgaa catgctcgtg cagtcgttta taacgctttt ttcgaatagg aggtggcgc   1020 ataggcgcca agagattttg ggacttgctg tgttttgggt ttggtttccg ctttagttt   1080 cttgcttacc taattggggt gagaggataa tgtttctgct tgtgagctat tccgttacgg   1140
ggatacaaca cgtgcagttc agcttgaacc attttttcttc ggacgtctac gtgggtccgc   1200
cagtaggtaa cgactggttc aagaaacaga ctgcaggac actgaacata tcgtgcccgg   1260
cgtggatgga ttggttccat ggtgggttgc aatttcaggt ggagcaccac ttgttcccgc   1320
ggatgcctag gagtcagttt aggaagattt ctcctttgt gagggatttg tgtaagaaac   1380
```

```
acaatttgcc ttacaacatc gcgtctttta ctaaagcgaa tgtgttgacg cttaagacgc   1440
tgagaaatac ggccgttgag gctcgggacc tctctaatcc gatcccaaag aacatggtgt   1500
gggaggctgt taaaactctc gggtga                                        1526
```

<210> SEQ ID NO 26
<211> LENGTH: 449
<212> TYPE: PRT
<213> ORGANISM: Primula waltonii

<400> SEQUENCE: 26

```
Met Ala Asn Lys Ser Gln Thr Gly Tyr Ile Thr Ser Ser Asp Leu Lys
1               5                   10                  15

Ser His Asn Lys Ala Gly Asp Leu Trp Ile Ser Ile His Gly Gln Val
            20                  25                  30

Tyr Asp Val Ser Ser Trp Ala Ser Leu His Pro Gly Gly Ser Ala Pro
        35                  40                  45

Leu Leu Ala Leu Ala Gly His Asp Val Thr Asp Ala Phe Leu Ala Tyr
    50                  55                  60

His Pro Pro Ser Thr Ala Arg Leu Leu Pro Leu Ser Ala Asn Leu
65                  70                  75                  80

Leu Leu Gln His His Ser Val Ser Pro Thr Ser Ser Asp Tyr Arg Ser
                85                  90                  95

Leu Leu Asn Asn Phe His Lys Leu Gly Leu Phe Arg Ser Arg Gly His
            100                 105                 110

Thr Ala Tyr Ala Thr Phe Val Phe Met Ile Thr Met Phe Val Met Ser
        115                 120                 125

Val Thr Gly Val Leu Phe Ser Asp Asp Ala Trp Val His Leu Ala Cys
    130                 135                 140

Gly Gly Ala Met Gly Ile Ala Trp Ile Gln Cys Gly Trp Ile Gly His
145                 150                 155                 160

Asp Ser Gly His Tyr Arg Met Met Ser Asp Arg Lys Trp Asn Arg Phe
                165                 170                 175

Ala Gln Ile Leu Ser Ala Asn Cys Leu Gln Gly Ile Ser Ile Gly Trp
            180                 185                 190

Trp Lys Trp Asn His Asn Ala His His Ile Ala Cys Asn Ser Leu Glu
        195                 200                 205

Tyr Asp Pro Asp Leu Gln Tyr Ile Pro Leu Leu Val Val Ser Pro Lys
    210                 215                 220

Phe Phe Asn Ser Leu Thr Ser Arg Phe Tyr Asn Lys Lys Leu Asn Phe
225                 230                 235                 240

Asp Gly Val Ser Arg Phe Leu Val Cys Tyr Gln His Trp Thr Phe Tyr
                245                 250                 255

Pro Val Met Cys Val Ala Arg Leu Asn Met Leu Val Gln Ser Phe Ile
            260                 265                 270

Thr Leu Phe Ser Asn Arg Glu Val Ala His Arg Ala Gln Glu Ile Leu
        275                 280                 285

Gly Leu Ala Val Phe Trp Val Trp Phe Pro Leu Leu Val Ser Cys Leu
    290                 295                 300

Pro Asn Trp Gly Glu Arg Ile Met Phe Leu Leu Val Ser Tyr Ser Val
305                 310                 315                 320

Thr Gly Ile Gln His Val Gln Phe Ser Leu Asn His Phe Ser Ser Asp
                325                 330                 335

Val Tyr Val Gly Pro Pro Val Gly Asn Asp Trp Phe Lys Lys Gln Thr
            340                 345                 350
```

```
Ala Gly Thr Leu Asn Ile Ser Cys Pro Ala Trp Met Asp Trp Phe His
        355                 360                 365

Gly Gly Leu Gln Phe Gln Val Glu His His Leu Phe Pro Arg Met Pro
        370                 375                 380

Arg Ser Gln Phe Arg Lys Ile Ser Pro Phe Val Arg Asp Leu Cys Lys
385                 390                 395                 400

Lys His Asn Leu Pro Tyr Asn Ile Ala Ser Phe Thr Lys Ala Asn Val
                405                 410                 415

Leu Thr Leu Lys Thr Leu Arg Asn Thr Ala Val Glu Ala Arg Asp Leu
            420                 425                 430

Ser Asn Pro Ile Pro Lys Asn Met Val Trp Glu Ala Val Lys Thr Leu
        435                 440                 445

Gly

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
cacacatgac cggataaaac gtccagt                                           27

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
agggatatac tggaggtcgg ggtcgta                                           27

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
gagctattcc gttacgggga tacaaca                                           27

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
tgcagggaca cttaacatat cgtgccc                                           27

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 31
gtgaaagttg ttgaggaggg atcggta                                      27

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
gtggaaggag gatggtaagc gaggaaa                                      27

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
gtcgacatgg ctaacaaatc tcaaacaggt tac                               33

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
cctgcaggtc acccgagagt tttaacagcc tcc                               33

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
cacacattac cggataaaac gtccagt                                      27

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
aggaatatac tggaggtctg ggtcgta                                      27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
```
atttttcttc ggacgtatac atgggcc                                              27

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
ttcggggaca ctgaacatat cgtgccc                                              27

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39
gtcgacatgg ccaacactag ttacatttcc agct                                      34

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
gatatcaccc cagagtgtta acagcttccc ag                                        32

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41
tggaggtctg ggtcgtaatc                                                      20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42
cttcggacgt atacatgggc                                                      20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 43
tcgtaatcca ggctattgca                                                      20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic Primer

<400> SEQUENCE: 44
ttttcttcgg acgtccatgt                                              20

<210> SEQ ID NO 45
<211> LENGTH: 1365
<212> TYPE: DNA
<213> ORGANISM: Primula farinosa

<400> SEQUENCE: 45
atgtccaaca catatccacc aaatcccaaa actagtcatt acatttccag ctcagacctc    60
aaaacccata taaacctga agacctttgg atatccattc acggccacgt gtacgatgtc   120
tccgcctggg cccccacca cctcggaggt gcctctctcc tcctcgccct cgcaggcaat   180
gatgtcaccg acaccttcct cgcctaccac cctccctcca cctgccgcct tctccctcct   240
ttctctacca acatcctcct cgaaaactac tccgtctccc acacctcctc tgactaccgc   300
aacctcctca atcatttcca caagctcggc ctattccgta caaaggccca tacgactttc   360
actactttct tcatcatgat acttatgttc tttctcagtg taaccggaat atttgcagt    420 gatagttttt gggtccattt ggcgtgcggt ggcttgatgg ggttcgcatg gatccaatgt   480
ggatggatag cgcacgactc tgggcattac cggataacat caagcaggaa atggaataga   540
ttcgctcaga tccttatcgg aaattgcctc caggggttga gtattgggtg gtggaagtgg   600
aaccataacg ctcaccacat cgcttgcaat agcctagatt acgacccgga tctccagtat   660
attcctttat tggtagtttc ttcaaagttt ttcaactcca tcacttctgg tttctatgat   720
aagaagctga acttcgacgg tgtgtcgagg ttcttagtta gctaccaaca ctggacgttt   780
tatccggtaa tgtgtgttgc taggtttaac atggttgcac agtcggttat acatgttttc   840
tcaaatagaa aggtgcccaa tagggttcta gaggttttcg gactaggcgt gttctgggtt   900
tggtattcgc tcctactttc gtgccttcct gattggggcg agcgaataat gtttgtgatt   960
gcatgctact tgttacggg gatacaacac gtacagttca gtgtaaacca tttttcttcg   1020
gacgtataca tgggccctcc cgtaggtaac gattggttta aaaaacagac tgcagggaca   1080
ctgaacatat cgtgcccgcc ctggatggat tggttccacg gtgggttgca gtttcaaatc   1140
gagcaccact tgttcccacg gatgccgagg ggtcaattta ggaagatctc tccttttgta   1200
aaggatttgt gtaataaaca caatctgcct tacaatatcg catcttttac tatggctaac   1260
gtgttgacgc ttaggaccct gagaaatacg gccattgagg cttgggacct ttctaatccg   1320
atcccaaaga atatggtctg ggaagctgtt aacactctgg ggtga              1365

<210> SEQ ID NO 46
<211> LENGTH: 454
<212> TYPE: PRT
<213> ORGANISM: Primula farinosa

<400> SEQUENCE: 46

Met Ser Asn Thr Tyr Pro Pro Asn Pro Lys Thr Ser His Tyr Ile Ser
1               5                   10                  15

Ser Ser Asp Leu Lys Thr His Asn Lys Pro Glu Asp Leu Trp Ile Ser

```
                    20                  25                  30
Ile His Gly His Val Tyr Asp Val Ser Ala Trp Ala Pro His His Leu
             35                  40                  45
Gly Gly Ala Ser Leu Leu Leu Ala Leu Ala Gly Asn Asp Val Thr Asp
 50                  55                  60
Thr Phe Leu Ala Tyr His Pro Pro Ser Thr Cys Arg Leu Leu Pro Pro
 65                  70                  75                  80
Phe Ser Thr Asn Ile Leu Leu Glu Asn Tyr Ser Val Ser His Thr Ser
                 85                  90                  95
Ser Asp Tyr Arg Asn Leu Leu Asn His Phe His Lys Leu Gly Leu Phe
             100                 105                 110
Arg Thr Lys Ala His Thr Thr Phe Thr Thr Phe Phe Ile Met Ile Leu
         115                 120                 125
Met Phe Phe Leu Ser Val Thr Gly Ile Phe Cys Ser Asp Ser Phe Trp
     130                 135                 140
Val His Leu Ala Cys Gly Gly Leu Met Gly Phe Ala Trp Ile Gln Cys
145                 150                 155                 160
Gly Trp Ile Ala His Asp Ser Gly His Tyr Arg Ile Thr Ser Ser Arg
                 165                 170                 175
Lys Trp Asn Arg Phe Ala Gln Ile Leu Ile Gly Asn Cys Leu Gln Gly
             180                 185                 190
Leu Ser Ile Gly Trp Trp Lys Trp Asn His Asn Ala His His Ile Ala
         195                 200                 205
Cys Asn Ser Leu Asp Tyr Asp Pro Asp Leu Gln Tyr Ile Pro Leu Leu
     210                 215                 220
Val Val Ser Ser Lys Phe Phe Asn Ser Ile Thr Ser Gly Phe Tyr Asp
225                 230                 235                 240
Lys Lys Leu Asn Phe Asp Gly Val Ser Arg Phe Leu Val Ser Tyr Gln
                 245                 250                 255
His Trp Thr Phe Tyr Pro Val Met Cys Val Ala Arg Phe Asn Met Val
             260                 265                 270
Ala Gln Ser Val Ile His Val Phe Ser Asn Arg Lys Val Pro Asn Arg
         275                 280                 285
Val Leu Glu Val Phe Gly Leu Gly Val Phe Trp Val Trp Tyr Ser Leu
     290                 295                 300
Leu Leu Ser Cys Leu Pro Asp Trp Gly Glu Arg Ile Met Phe Val Ile
305                 310                 315                 320
Ala Cys Tyr Phe Val Thr Gly Ile Gln His Val Gln Phe Ser Val Asn
                 325                 330                 335
His Phe Ser Ser Asp Val Tyr Met Gly Pro Pro Val Gly Asn Asp Trp
             340                 345                 350
Phe Lys Lys Gln Thr Ala Gly Thr Leu Asn Ile Ser Cys Pro Pro Trp
         355                 360                 365
Met Asp Trp Phe His Gly Gly Leu Gln Phe Gln Ile Glu His His Leu
     370                 375                 380
Phe Pro Arg Met Pro Arg Gly Gln Phe Arg Lys Ile Ser Pro Phe Val
385                 390                 395                 400
Lys Asp Leu Cys Asn Lys His Asn Leu Pro Tyr Asn Ile Ala Ser Phe
                 405                 410                 415
Thr Met Ala Asn Val Leu Thr Leu Arg Thr Leu Arg Asn Thr Ala Ile
             420                 425                 430
Glu Ala Trp Asp Leu Ser Asn Pro Ile Pro Lys Asn Met Val Trp Glu
         435                 440                 445
```

Ala Val Asn Thr Leu Gly
    450

<210> SEQ ID NO 47
<211> LENGTH: 1559
<212> TYPE: DNA
<213> ORGANISM: Primula florindae

<400> SEQUENCE: 47

```
atggctaaca aatctcaaac aggttacata accagctcag acctgaaagg ccacaataag      60
gcaggtgatc tatggatatc aatccacggt caggtctacg acgtgtcctc gtgggccagc     120
cttcacccgg ggggcagtgc cccctcctg gccctcgcag acacgacgt gaccgacgct      180
ttcctcgctt accatccccc ttccaccgcc cgccttctcc ctcccctctc cgctaacctc     240
cttctacaac accactccgt ctcccccacc tcctctgatt accgctccct cctcaacaac     300
tttcataaac ttggcctgtt ccgcaccagg ggccacaccg cttacgcaac cttcgtcttc     360
atgatagcga tgtttgtaat gagcgtgacc ggagtgcttt tagcgacga tgcgtgggtc      420
catctggctt gcgccggagc aatggggatt gcctggatcc aatgcggatg gataggtcgg     480
tagactaatc tattagtaca taaaaacata tttaatattt aaaataccat attcttaaat     540
cttatttaaa ttttggtatg tatcaatatg ggttaaaaca aaagtaaaa ataagtagaa      600
tgtatactta aaatagatat taactatgag tttttgataa ttaagattca aattatgtac     660
taaatgatca tttttcctgg ataggtcacg actctgggca ttaccggatg atgtctgaca     720
ggaaatggaa ccggtttgcg caaatcctga gcgcaaactg cctccagggg attagcatcg     780
ggtggtggaa gtggaaccac aacgcgcacc acatcgcttg caatagcctg gattacgacc     840
ccgacctcca gtatatccct tgctcgtcg tctcccccaa gttttcaac tcccttactt      900
ctcgtttcta caacaagaaa ctgaacttcg acggtgtgtc gaggttcttg gtttgctacc     960
agcactggac gttttatccg gtcatgtgtg tcgctaggct gaacatgctc gtgcagtcgt    1020
ttataacgct ttttcgaat agggaggtgg cgcatagggc gcaagagatt ttgggacttg    1080
ctgtgtttg ggtttggttt ccgcttttac tttcttgctt acctaattgg ggtgagagga    1140
taatgtttct gcttgtgagc tattccatta cggggataca acacgtgcag tttagcttga    1200
accattttc ttcggacgtc tatgtgggtc cgccagtagg taacgactgg ttcaagaaac    1260
agactgcagg gacacttaac atatcgtgcc cggcgtggat ggattggttc catggtgggt    1320
tgcagtttca ggtcgagcac cacttgttcc cgcggatgcc taggagtcag tttaggaaga    1380
tttctccttt tgtgagggat ttgtgtaaga aacacaattt gccttacaac atcgcgtctt    1440
ttactaaagc gaatgtgttg acgcttaaga cgctgagaaa tacagccgtt gaggctcggg    1500
acctctctaa tccgatccca aagaatatgg tgtgggaggc tgttaaaact ctcgggtga    1559
```

<210> SEQ ID NO 48
<211> LENGTH: 449
<212> TYPE: PRT
<213> ORGANISM: Primula florindae

<400> SEQUENCE: 48

Met Ala Asn Lys Ser Gln Thr Gly Tyr Ile Thr Ser Ser Asp Leu Lys
1               5                   10                  15

Gly His Asn Lys Ala Gly Asp Leu Trp Ile Ser Ile His Gly Gln Val
            20                  25                  30

Tyr Asp Val Ser Ser Trp Ala Ser Leu His Pro Gly Gly Ser Ala Pro
        35                  40                  45

-continued

```
Leu Leu Ala Leu Ala Gly His Asp Val Thr Asp Ala Phe Leu Ala Tyr
 50                  55                  60
His Pro Pro Ser Thr Ala Arg Leu Leu Pro Pro Leu Ser Ala Asn Leu
 65                  70                  75                  80
Leu Leu Gln His His Ser Val Ser Pro Thr Ser Asp Tyr Arg Ser
                 85                  90                  95
Leu Leu Asn Asn Phe His Lys Leu Gly Leu Phe Arg Thr Arg Gly His
                100                 105                 110
Thr Ala Tyr Ala Thr Phe Val Phe Met Ile Ala Met Phe Val Met Ser
                115                 120                 125
Val Thr Gly Val Leu Phe Ser Asp Asp Ala Trp Val His Leu Ala Cys
130                 135                 140
Ala Gly Ala Met Gly Ile Ala Trp Ile Gln Cys Gly Trp Ile Gly His
145                 150                 155                 160
Asp Ser Gly His Tyr Arg Met Met Ser Asp Arg Lys Trp Asn Arg Phe
                165                 170                 175
Ala Gln Ile Leu Ser Ala Asn Cys Leu Gln Gly Ile Ser Ile Gly Trp
                180                 185                 190
Trp Lys Trp Asn His Asn Ala His His Ile Ala Cys Asn Ser Leu Asp
                195                 200                 205
Tyr Asp Pro Asp Leu Gln Tyr Ile Pro Leu Leu Val Val Ser Pro Lys
                210                 215                 220
Phe Phe Asn Ser Leu Thr Ser Arg Phe Tyr Asn Lys Lys Leu Asn Phe
225                 230                 235                 240
Asp Gly Val Ser Arg Phe Leu Val Cys Tyr Gln His Trp Thr Phe Tyr
                245                 250                 255
Pro Val Met Cys Val Ala Arg Leu Asn Met Leu Val Gln Ser Phe Ile
                260                 265                 270
Thr Leu Phe Ser Asn Arg Glu Val Ala His Arg Ala Gln Glu Ile Leu
                275                 280                 285
Gly Leu Ala Val Phe Trp Val Trp Phe Pro Leu Leu Leu Ser Cys Leu
                290                 295                 300
Pro Asn Trp Gly Glu Arg Ile Met Phe Leu Leu Val Ser Tyr Ser Ile
305                 310                 315                 320
Thr Gly Ile Gln His Val Gln Phe Ser Leu Asn His Phe Ser Ser Asp
                325                 330                 335
Val Tyr Val Gly Pro Pro Val Gly Asn Asp Trp Phe Lys Lys Gln Thr
                340                 345                 350
Ala Gly Thr Leu Asn Ile Ser Cys Pro Ala Trp Met Asp Trp Phe His
                355                 360                 365
Gly Gly Leu Gln Phe Gln Val Glu His His Leu Phe Pro Arg Met Pro
                370                 375                 380
Arg Ser Gln Phe Arg Lys Ile Ser Pro Phe Val Arg Asp Leu Cys Lys
385                 390                 395                 400
Lys His Asn Leu Pro Tyr Asn Ile Ala Ser Phe Thr Lys Ala Asn Val
                405                 410                 415
Leu Thr Leu Lys Thr Leu Arg Asn Thr Ala Val Glu Ala Arg Asp Leu
                420                 425                 430
Ser Asn Pro Ile Pro Lys Asn Met Val Trp Glu Ala Val Lys Thr Leu
                435                 440                 445
Gly

<210> SEQ ID NO 49
<211> LENGTH: 38
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 49
gacgattttt gagtgagagt taatttgagt caataata                                 38

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 50
cgacatcata gacaatcatc aagacaccgt                                          30

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 51
ataccccctc aaaacacccc caaat                                               25

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 52
ctcaatatca cccgagagtt ttaacagcct                                          30

<210> SEQ ID NO 53
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 53
gtcgacaaca atgtccaaca catatccacc aaatc                                    35

<210> SEQ ID NO 54
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 54
cctgcaggtc accccagagt gttaacagct tc                                       32

<210> SEQ ID NO 55
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      Primer

<400> SEQUENCE: 55
gtcgacatgg ctaacaaatc tcaaac                                              26

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 56
cctgcaggtc acccgagagt                                                     20

<210> SEQ ID NO 57
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 57
gtaatgccca gagtcgtgac ctatccatcc gcactggatc c                             41

<210> SEQ ID NO 58
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 58
gatccagtgc ggatggatag gtcacgactc tgggcattac cg                            42

<210> SEQ ID NO 59
<211> LENGTH: 448
<212> TYPE: PRT
<213> ORGANISM: Borago officinalis

<400> SEQUENCE: 59

Met Ala Ala Gln Ile Lys Lys Tyr Ile Thr Ser Asp Glu Leu Lys Asn
1               5                   10                  15

His Asp Lys Pro Gly Asp Leu Trp Ile Ser Ile Gln Gly Lys Ala Tyr
            20                  25                  30

Asp Val Ser Asp Trp Val Lys Asp His Pro Gly Gly Ser Phe Pro Leu
        35                  40                  45

Lys Ser Leu Ala Gly Gln Glu Val Thr Asp Ala Phe Val Ala Phe His
    50                  55                  60

Pro Ala Ser Thr Trp Lys Asn Leu Asp Lys Phe Phe Thr Gly Tyr Tyr
65                  70                  75                  80

Leu Lys Asp Tyr Ser Val Ser Glu Val Ser Lys Asp Tyr Arg Lys Leu
                85                  90                  95

Val Phe Glu Phe Ser Lys Met Gly Leu Tyr Asp Lys Lys Gly His Ile
            100                 105                 110

Met Phe Ala Thr Leu Cys Phe Ile Ala Met Leu Phe Ala Met Ser Val
        115                 120                 125

Tyr Gly Val Leu Phe Cys Glu Gly Val Leu Val His Leu Phe Ser Gly
```

```
             130                 135                 140
Cys Leu Met Gly Phe Leu Trp Ile Gln Ser Gly Trp Ile Gly His Asp
145                 150                 155                 160

Ala Gly His Tyr Met Val Val Ser Asp Ser Arg Leu Asn Lys Phe Met
                165                 170                 175

Gly Ile Phe Ala Ala Asn Cys Leu Ser Gly Ile Ser Ile Gly Trp Trp
                180                 185                 190

Lys Trp Asn His Asn Ala His Ile Ala Cys Asn Ser Leu Glu Tyr
                195                 200                 205

Asp Pro Asp Leu Gln Tyr Ile Pro Phe Leu Val Val Ser Ser Lys Phe
210                 215                 220

Phe Gly Ser Leu Thr Ser His Phe Tyr Glu Lys Arg Leu Thr Phe Asp
225                 230                 235                 240

Ser Leu Ser Arg Phe Phe Val Ser Tyr Gln His Trp Thr Phe Tyr Pro
                245                 250                 255

Ile Met Cys Ala Ala Arg Leu Asn Met Tyr Val Gln Ser Leu Ile Met
                260                 265                 270

Leu Leu Thr Lys Arg Asn Val Ser Tyr Arg Ala His Glu Leu Leu Gly
                275                 280                 285

Cys Leu Val Phe Ser Ile Trp Tyr Pro Leu Leu Val Ser Cys Leu Pro
                290                 295                 300

Asn Trp Gly Glu Arg Ile Met Phe Val Ile Ala Ser Leu Ser Val Thr
305                 310                 315                 320

Gly Met Gln Gln Val Gln Phe Ser Leu Asn His Phe Ser Ser Val
                325                 330                 335

Tyr Val Gly Lys Pro Lys Gly Asn Asn Trp Phe Glu Lys Gln Thr Asp
                340                 345                 350

Gly Thr Leu Asp Ile Ser Cys Pro Pro Trp Met Asp Trp Phe His Gly
                355                 360                 365

Gly Leu Gln Phe Gln Ile Glu His His Leu Phe Pro Lys Met Pro Arg
                370                 375                 380

Cys Asn Leu Arg Lys Ile Ser Pro Tyr Val Ile Glu Leu Cys Lys Lys
385                 390                 395                 400

His Asn Leu Pro Tyr Asn Tyr Ala Ser Phe Ser Lys Ala Asn Glu Met
                405                 410                 415

Thr Leu Arg Thr Leu Arg Asn Thr Ala Leu Gln Ala Arg Asp Ile Thr
                420                 425                 430

Lys Pro Leu Pro Lys Asn Leu Val Trp Glu Ala Leu His Thr His Gly
                435                 440                 445

<210> SEQ ID NO 60
<211> LENGTH: 448
<212> TYPE: PRT
<213> ORGANISM: Echium gentianoides

<400> SEQUENCE: 60

Met Ala Asn Ala Ile Lys Lys Tyr Ile Thr Ala Glu Glu Leu Lys Lys
1               5                   10                  15

His Asp Lys Glu Gly Asp Leu Trp Ile Ser Ile Gln Gly Lys Val Tyr
                20                  25                  30

Asp Val Ser Asp Trp Leu Lys Asp His Pro Gly Gly Lys Phe Pro Leu
                35                  40                  45

Leu Ser Leu Ala Gly Gln Glu Val Thr Asp Ala Phe Val Ala Phe His
                50                  55                  60

Ser Gly Ser Thr Trp Lys Phe Leu Asp Ser Phe Phe Thr Gly Tyr Tyr
```

```
            65                  70                  75                  80
        Leu Lys Asp Tyr Ser Val Ser Glu Val Ser Lys Asp Tyr Arg Lys Leu
                            85                  90                  95

Val Phe Glu Phe Asn Lys Met Gly Leu Phe Asp Lys Lys Gly His Ile
                        100                 105                 110

Val Leu Val Thr Val Leu Phe Ile Ala Met Met Phe Ala Met Ser Val
                        115                 120                 125

Tyr Gly Val Leu Phe Cys Glu Gly Val Leu Val His Leu Leu Ala Gly
                        130                 135                 140

Gly Leu Met Gly Phe Val Trp Ile Gln Ser Gly Trp Ile Gly His Asp
        145                 150                 155                 160

Ala Gly His Tyr Ile Val Met Pro Asn Pro Arg Leu Asn Lys Leu Met
                        165                 170                 175

Gly Ile Val Ala Gly Asn Cys Leu Ser Gly Ile Ser Ile Gly Trp Trp
                        180                 185                 190

Lys Trp Asn His Asn Ala His His Ile Ala Cys Asn Ser Leu Asp Tyr
                        195                 200                 205

Asp Pro Asp Leu Gln Tyr Ile Pro Phe Leu Val Val Ser Ser Lys Leu
                        210                 215                 220

Phe Ser Ser Leu Thr Ser His Phe Tyr Glu Lys Lys Leu Thr Phe Asp
        225                 230                 235                 240

Ser Leu Ser Arg Phe Phe Val Ser His Gln His Trp Thr Phe Tyr Pro
                        245                 250                 255

Val Met Cys Ser Ala Arg Val Asn Met Phe Val Gln Ser Leu Ile Met
                        260                 265                 270

Leu Leu Thr Lys Arg Asn Val Phe Tyr Arg Ser Gln Glu Leu Leu Gly
                        275                 280                 285

Leu Val Val Phe Trp Ile Trp Tyr Pro Leu Leu Val Ser Cys Leu Pro
                        290                 295                 300

Asn Trp Gly Glu Arg Ile Met Phe Val Val Ala Ser Leu Ser Val Thr
        305                 310                 315                 320

Gly Met Gln Gln Val Gln Phe Ser Leu Asn His Phe Ser Ala Ser Val
                        325                 330                 335

Tyr Val Gly Gln Pro Lys Gly Asn Asp Trp Phe Glu Lys Gln Thr Cys
                        340                 345                 350

Gly Thr Leu Asp Ile Ser Cys Pro Ser Trp Met Asp Trp Phe His Gly
                        355                 360                 365

Gly Leu Gln Phe Gln Val Glu His His Leu Phe Pro Lys Leu Pro Arg
                        370                 375                 380

Cys His Leu Arg Lys Ile Ser Pro Phe Val Met Glu Leu Cys Lys Lys
        385                 390                 395                 400

His Asn Leu Ser Tyr Asn Cys Ala Ser Phe Ser Glu Ala Asn Glu Met
                        405                 410                 415

Thr Leu Arg Thr Leu Arg Asp Thr Ala Leu Gln Ala Arg Asp Leu Thr
                        420                 425                 430

Lys Pro Leu Pro Lys Asn Leu Val Trp Glu Ala Leu Asn Thr His Gly
                        435                 440                 445
```